(12) United States Patent
Voss

(10) Patent No.: US 9,149,276 B2
(45) Date of Patent: Oct. 6, 2015

(54) CLIP AND DEPLOYMENT APPARATUS FOR TISSUE CLOSURE

(75) Inventor: Laveille Kao Voss, Belmont, CA (US)

(73) Assignee: ABBOTT CARDIOVASCULAR SYSTEMS, INC., Santa Clara, CA (US)

( * ) Notice: Subject to any disclaimer, the term of this patent is extended or adjusted under 35 U.S.C. 154(b) by 123 days.

(21) Appl. No.: 13/052,634

(22) Filed: Mar. 21, 2011

(65) Prior Publication Data

US 2012/0245603 A1   Sep. 27, 2012

(51) Int. Cl.
| | |
|---|---|
| *A61B 17/10* | (2006.01) |
| *A61B 17/08* | (2006.01) |
| *A61B 17/128* | (2006.01) |
| *A61B 17/00* | (2006.01) |

(52) U.S. Cl.
CPC ............ *A61B 17/10* (2013.01); *A61B 17/0057* (2013.01); *A61B 17/08* (2013.01); *A61B 17/128* (2013.01); *A61B 17/1285* (2013.01); *A61B 2017/00584* (2013.01); *A61B 2017/00659* (2013.01); *A61B 2017/00986* (2013.01)

(58) Field of Classification Search
CPC ............. A61B 17/128; A61B 17/1285; A61B 17/0057; A61B 17/10; A61B 17/08; A61B 17/083; A61B 2017/00584; A61B 2017/081
USPC ......... 606/142, 143, 151, 157, 158, 140, 141, 606/120, 149, 215, 216, 213; 604/104–109; 132/273, 278; 24/30.5 S, 30.5 R, 545; 600/127

See application file for complete search history.

(56) References Cited

U.S. PATENT DOCUMENTS

| | | | |
|---|---|---|---|
| 287,046 A | 10/1883 | Norton | |
| 438,400 A | 10/1890 | Brennen | |
| 556,082 A | 3/1896 | Boeddinghaus | |
| 1,088,393 A | 2/1914 | Backus | |
| 1,242,139 A * | 10/1917 | Callahan | ..................... 24/30.5 S |
| 1,331,401 A | 2/1920 | Summers | |
| 1,480,935 A * | 1/1924 | Gleason | ........................ 132/278 |
| 1,596,004 A | 8/1926 | De Bengoa | |

(Continued)

FOREIGN PATENT DOCUMENTS

| | | |
|---|---|---|
| AU | 2003297432 | 7/2004 |
| CA | 2 339 060 | 2/2000 |

(Continued)

OTHER PUBLICATIONS

U.S. Appl. No. 09/610,128, filed Jul. 5, 2000, Kerievsky.

(Continued)

*Primary Examiner* — Julian W Woo
*Assistant Examiner* — Christopher L Templeton
(74) *Attorney, Agent, or Firm* — Workman Nydegger; Randy Shen

(57) ABSTRACT

A tissue engaging device and a corresponding deployment apparatus. The tissue engaging device has a generally annular-shaped body disposed about a central axis. The body has a plurality of inwardly protruding members separated by corresponding intermember spaces. The body is movable between a first position where the body is substantially convex before engagement with the tissue and a second position where the body is substantially concave when the body is engaged with the tissue. The tissue engaging device may be bioabsorbable. The deployment apparatus has a sheath and a tissue eversion apparatus for everting the tissue and positioning the everted tissue within the tissue engaging device.

20 Claims, 13 Drawing Sheets

(56) References Cited

U.S. PATENT DOCUMENTS

| | | |
|---|---|---|
| 1,647,958 A | 11/1927 | Ciarlante |
| 1,880,569 A | 10/1932 | Weis |
| 2,087,074 A | 7/1937 | Tucker |
| 2,108,206 A | 2/1938 | Meeker |
| 2,210,061 A | 8/1940 | Caminez |
| 2,254,620 A | 9/1941 | Miller |
| 2,316,297 A | 4/1943 | Southerland et al. |
| 2,371,978 A | 3/1945 | Perham |
| 2,453,227 A | 11/1948 | James |
| 2,583,625 A | 1/1952 | Bergan |
| 2,610,631 A | 9/1952 | Calicchio |
| 2,684,070 A | 7/1954 | Kelsey |
| 2,755,699 A | 7/1956 | Forster |
| 2,910,067 A | 10/1959 | White |
| 2,944,311 A | 7/1960 | Schneckenberger |
| 2,951,482 A | 9/1960 | Sullivan |
| 2,969,887 A | 1/1961 | Darmstadt et al. |
| 3,015,403 A | 1/1962 | Fuller |
| 3,113,379 A | 12/1963 | Frank |
| 3,120,230 A | 2/1964 | Skold |
| 3,142,878 A | 8/1964 | Santora |
| 3,209,754 A | 10/1965 | Brown |
| 3,348,595 A * | 10/1967 | Stevens, Jr. .................... 206/525 |
| 3,357,070 A * | 12/1967 | Soloan ............................ 24/562 |
| 3,482,428 A | 12/1969 | Kapitanov et al. |
| 3,494,533 A | 2/1970 | Green et al. |
| 3,510,923 A | 5/1970 | Blake |
| 3,523,351 A | 8/1970 | Filia |
| 3,586,002 A | 6/1971 | Wood |
| 3,604,425 A | 9/1971 | Le Roy |
| 3,618,447 A | 11/1971 | Goins |
| 3,677,243 A | 7/1972 | Nerz |
| 3,682,180 A * | 8/1972 | McFarlane .................... 604/174 |
| 3,757,629 A | 9/1973 | Schneider |
| 3,760,810 A | 9/1973 | Van Hoorn |
| 3,805,337 A | 4/1974 | Branstetter |
| 3,814,104 A | 6/1974 | Irnich et al. |
| 3,823,719 A | 7/1974 | Cummings |
| 3,828,791 A | 8/1974 | Santos |
| 3,856,016 A | 12/1974 | Davis |
| 3,856,018 A | 12/1974 | Perisse et al. |
| 3,874,388 A | 4/1975 | King et al. |
| 3,908,662 A | 9/1975 | Razgulov et al. |
| 3,926,194 A | 12/1975 | Greenberg et al. |
| 3,939,820 A | 2/1976 | Grayzel |
| 3,944,114 A | 3/1976 | Coppens |
| 3,960,147 A | 6/1976 | Murray |
| 3,985,138 A | 10/1976 | Jarvik |
| 4,007,743 A | 2/1977 | Blake |
| 4,011,872 A | 3/1977 | Komiya |
| 4,014,492 A | 3/1977 | Rothfuss |
| 4,018,228 A | 4/1977 | Goosen |
| 4,018,229 A | 4/1977 | Komiya |
| 4,047,533 A | 9/1977 | Perciaccante et al. |
| 4,064,881 A | 12/1977 | Meredith |
| 4,112,944 A | 9/1978 | Williams |
| 4,153,321 A | 5/1979 | Pombrol |
| 4,162,673 A | 7/1979 | Patel |
| 4,169,476 A | 10/1979 | Hiltebrandt |
| 4,189,808 A * | 2/1980 | Brown ........................ 24/30.5 R |
| 4,192,315 A | 3/1980 | Hilzinger et al. |
| 4,201,215 A | 5/1980 | Crossett et al. |
| 4,204,541 A | 5/1980 | Kapitanov |
| 4,207,870 A | 6/1980 | Eldridge |
| 4,214,587 A | 7/1980 | Sakura, Jr. |
| 4,215,699 A | 8/1980 | Patel |
| 4,217,902 A | 8/1980 | March |
| 4,267,995 A * | 5/1981 | McMillan .................... 248/74.1 |
| 4,273,129 A | 6/1981 | Boebel |
| 4,274,415 A | 6/1981 | Kanamoto et al. |
| 4,278,091 A | 7/1981 | Borzone |
| 4,317,445 A | 3/1982 | Robinson |
| 4,317,451 A | 3/1982 | Cerwin et al. |
| 4,318,401 A | 3/1982 | Zimmerman |
| 4,327,485 A | 5/1982 | Rix |
| 4,345,606 A | 8/1982 | Littleford |
| 4,359,052 A | 11/1982 | Staub |
| 4,368,736 A | 1/1983 | Kaster |
| 4,396,139 A | 8/1983 | Hall et al. |
| 4,407,286 A | 10/1983 | Noiles et al. |
| 4,411,654 A | 10/1983 | Boarini et al. |
| 4,412,832 A | 11/1983 | Kling et al. |
| 4,428,376 A | 1/1984 | Mericle |
| 4,440,170 A | 4/1984 | Golden et al. |
| 4,449,531 A | 5/1984 | Cerwin et al. |
| 4,475,544 A | 10/1984 | Reis |
| 4,480,356 A | 11/1984 | Martin |
| 4,485,816 A | 12/1984 | Krumme |
| 4,501,276 A | 2/1985 | Lombardi |
| RE31,855 E | 3/1985 | Osborne |
| 4,505,273 A | 3/1985 | Braun et al. |
| 4,505,274 A | 3/1985 | Speelman |
| 4,523,591 A | 6/1985 | Kaplan et al. |
| 4,523,695 A | 6/1985 | Braun et al. |
| 4,525,157 A | 6/1985 | Vaillancourt |
| 4,526,174 A | 7/1985 | Froehlich |
| 4,586,503 A | 5/1986 | Kirsch et al. |
| 4,592,498 A | 6/1986 | Braun et al. |
| 4,596,559 A | 6/1986 | Fleischhacker |
| 4,607,638 A | 8/1986 | Crainich |
| 4,610,251 A | 9/1986 | Kumar |
| 4,610,252 A | 9/1986 | Catalano |
| 4,635,634 A | 1/1987 | Santos |
| 4,651,737 A | 3/1987 | Deniega |
| 4,664,305 A | 5/1987 | Blake, III et al. |
| 4,665,906 A | 5/1987 | Jervis |
| 4,687,469 A | 8/1987 | Osypka |
| 4,693,249 A | 9/1987 | Schenck et al. |
| 4,697,312 A * | 10/1987 | Freyer ........................ 24/30.5 S |
| 4,719,917 A | 1/1988 | Barrows et al. |
| 4,724,840 A | 2/1988 | McVay et al. |
| 4,738,658 A | 4/1988 | Magro et al. |
| 4,744,364 A | 5/1988 | Kensey |
| 4,747,407 A | 5/1988 | Liu et al. |
| 4,759,364 A | 7/1988 | Boebel |
| 4,771,782 A | 9/1988 | Millar |
| 4,772,266 A | 9/1988 | Groshong |
| 4,777,950 A | 10/1988 | Kees, Jr. |
| 4,789,090 A | 12/1988 | Blake, III |
| 4,830,002 A | 5/1989 | Semm |
| 4,832,688 A | 5/1989 | Sagae et al. |
| 4,836,204 A | 6/1989 | Landymore et al. |
| 4,852,568 A | 8/1989 | Kensey |
| 4,860,746 A | 8/1989 | Yoon |
| 4,865,026 A | 9/1989 | Barrett |
| 4,874,122 A | 10/1989 | Froelich et al. |
| 4,878,915 A | 11/1989 | Brantigan |
| 4,885,003 A | 12/1989 | Hillstead |
| 4,886,067 A | 12/1989 | Palermo |
| 4,887,601 A | 12/1989 | Richards |
| 4,890,612 A | 1/1990 | Kensey |
| 4,902,508 A | 2/1990 | Badylak et al. |
| 4,917,087 A | 4/1990 | Walsh et al. |
| 4,917,089 A | 4/1990 | Sideris |
| 4,929,240 A | 5/1990 | Kirsch et al. |
| 4,934,364 A | 6/1990 | Green |
| 4,950,258 A | 8/1990 | Kawai et al. |
| 4,957,499 A | 9/1990 | Lipatov et al. |
| 4,961,729 A | 10/1990 | Vaillancourt |
| 4,967,949 A | 11/1990 | Sandhaus |
| 4,976,721 A | 12/1990 | Blasnik et al. |
| 4,983,176 A | 1/1991 | Cushman et al. |
| 4,997,436 A | 3/1991 | Oberlander |
| 4,997,439 A | 3/1991 | Chen |
| 5,002,562 A | 3/1991 | Oberlander |
| 5,007,921 A | 4/1991 | Brown |
| 5,015,247 A | 5/1991 | Michelson |
| 5,021,059 A | 6/1991 | Kensey et al. |
| 5,026,390 A | 6/1991 | Brown |
| 5,030,226 A | 7/1991 | Green et al. |
| 5,032,127 A | 7/1991 | Frazee et al. |
| 5,035,692 A | 7/1991 | Lyon et al. |
| 5,041,129 A | 8/1991 | Hayhurst et al. |
| 5,047,047 A | 9/1991 | Yoon |

(56) References Cited

U.S. PATENT DOCUMENTS

| | | |
|---|---|---|
| 5,053,008 A | 10/1991 | Bajaj |
| 5,059,201 A | 10/1991 | Asnis |
| 5,061,274 A | 10/1991 | Kensey |
| 5,078,731 A | 1/1992 | Hayhurst |
| 5,092,941 A | 3/1992 | Miura |
| 5,100,418 A | 3/1992 | Yoon et al. |
| 5,100,422 A | 3/1992 | Berguer et al. |
| 5,108,420 A | 4/1992 | Marks |
| 5,108,421 A | 4/1992 | Fowler |
| 5,114,032 A | 5/1992 | Laidlaw |
| 5,114,065 A | 5/1992 | Storace |
| 5,116,349 A | 5/1992 | Aranyi |
| 5,122,122 A | 6/1992 | Allgood |
| 5,122,156 A | 6/1992 | Granger et al. |
| 5,131,379 A | 7/1992 | Sewell, Jr. |
| 5,133,360 A | 7/1992 | Spears |
| 5,141,520 A | 8/1992 | Goble et al. |
| 5,147,381 A | 9/1992 | Heimerl et al. |
| 5,156,609 A | 10/1992 | Nakao et al. |
| 5,163,343 A | 11/1992 | Gish |
| 5,167,634 A | 12/1992 | Corrigan, Jr. et al. |
| 5,167,643 A | 12/1992 | Lynn |
| 5,171,249 A | 12/1992 | Stefanchik et al. |
| 5,171,250 A | 12/1992 | Yoon |
| 5,176,648 A | 1/1993 | Holmes et al. |
| 5,176,691 A | 1/1993 | Pierce |
| 5,192,287 A | 3/1993 | Fournier et al. |
| 5,192,288 A | 3/1993 | Thompson et al. |
| 5,192,300 A | 3/1993 | Fowler |
| 5,192,301 A | 3/1993 | Kamiya et al. |
| 5,192,302 A | 3/1993 | Kensey et al. |
| 5,192,602 A | 3/1993 | Spencer et al. |
| 5,193,533 A | 3/1993 | Body et al. |
| 5,197,971 A | 3/1993 | Bonutti |
| 5,207,697 A | 5/1993 | Carusillo et al. |
| 5,209,756 A | 5/1993 | Seedhorm et al. |
| 5,217,024 A | 6/1993 | Dorsey et al. |
| 5,217,471 A | 6/1993 | Burkhart |
| 5,222,974 A | 6/1993 | Kensey et al. |
| 5,226,908 A | 7/1993 | Yoon |
| 5,236,435 A | 8/1993 | Sewell, Jr. |
| 5,237,996 A | 8/1993 | Waldman et al. |
| 5,242,456 A | 9/1993 | Nash et al. |
| 5,242,457 A | 9/1993 | Akopov et al. |
| 5,242,459 A | 9/1993 | Buelna |
| 5,243,857 A | 9/1993 | Velez |
| 5,246,156 A | 9/1993 | Rothfuss et al. |
| 5,246,443 A | 9/1993 | Mai |
| 5,250,058 A | 10/1993 | Miller et al. |
| 5,254,105 A | 10/1993 | Haaga |
| 5,255,679 A | 10/1993 | Imran |
| 5,269,792 A | 12/1993 | Kovac et al. |
| 5,275,616 A | 1/1994 | Fowler |
| 5,281,422 A | 1/1994 | Badylak et al. |
| 5,282,808 A | 2/1994 | Kovac et al. |
| 5,282,827 A | 2/1994 | Kensey et al. |
| 5,289,963 A | 3/1994 | McGarry et al. |
| 5,290,243 A | 3/1994 | Chodorow et al. |
| 5,290,284 A | 3/1994 | Adair |
| 5,290,310 A | 3/1994 | Makower et al. |
| 5,292,309 A | 3/1994 | Van Tassel et al. |
| 5,292,332 A | 3/1994 | Lee |
| 5,300,078 A | 4/1994 | Buelna |
| 5,304,183 A | 4/1994 | Gourlay et al. |
| 5,304,184 A | 4/1994 | Hathaway et al. |
| 5,304,204 A | 4/1994 | Bregen |
| 5,306,254 A | 4/1994 | Nash et al. |
| 5,309,927 A | 5/1994 | Welch |
| 5,318,542 A | 6/1994 | Hirsch et al. |
| 5,320,639 A | 6/1994 | Rudnick |
| 5,327,908 A | 7/1994 | Gerry |
| 5,330,445 A | 7/1994 | Haaga |
| 5,330,503 A | 7/1994 | Yoon |
| 5,334,216 A | 8/1994 | Vidal et al. |
| 5,334,217 A | 8/1994 | Das |
| 5,335,680 A | 8/1994 | Moore |
| 5,336,231 A | 8/1994 | Adair |
| 5,340,360 A | 8/1994 | Stefanchik |
| 5,342,393 A | 8/1994 | Stack |
| 5,344,439 A | 9/1994 | Otten |
| 5,350,399 A | 9/1994 | Erlebacher et al. |
| 5,352,229 A | 10/1994 | Goble et al. |
| 5,354,279 A | 10/1994 | Hofling |
| 5,364,406 A | 11/1994 | Sewell, Jr. |
| 5,364,408 A | 11/1994 | Gordon |
| 5,366,458 A | 11/1994 | Korthoff et al. |
| 5,366,479 A | 11/1994 | McGarry et al. |
| 5,383,896 A | 1/1995 | Gershony et al. |
| 5,383,897 A | 1/1995 | Wholey |
| 5,383,905 A | 1/1995 | Golds et al. |
| RE34,866 E | 2/1995 | Kensey et al. |
| 5,392,978 A | 2/1995 | Velez et al. |
| 5,395,030 A | 3/1995 | Kuramoto et al. |
| 5,403,330 A | 4/1995 | Tuason |
| 5,403,331 A | 4/1995 | Chesterfield et al. |
| 5,404,621 A * | 4/1995 | Heinke ..................... 24/30.5 R |
| 5,411,520 A | 5/1995 | Nash et al. |
| 5,413,571 A | 5/1995 | Katsaros et al. |
| 5,413,584 A | 5/1995 | Schulze |
| 5,416,584 A | 5/1995 | Kay |
| 5,417,699 A | 5/1995 | Klein et al. |
| 5,419,765 A | 5/1995 | Weldon et al. |
| 5,419,777 A | 5/1995 | Hofling |
| 5,421,832 A | 6/1995 | Lefebvre |
| 5,423,857 A | 6/1995 | Rosenman et al. |
| 5,425,489 A | 6/1995 | Shichman et al. |
| 5,425,740 A | 6/1995 | Hutchinson, Jr. |
| 5,431,639 A | 7/1995 | Shaw |
| 5,431,667 A | 7/1995 | Thompson et al. |
| 5,433,721 A | 7/1995 | Hooven et al. |
| 5,437,631 A | 8/1995 | Janzen |
| 5,439,479 A | 8/1995 | Shichman et al. |
| 5,443,477 A | 8/1995 | Marin et al. |
| 5,443,481 A | 8/1995 | Lee |
| 5,445,167 A | 8/1995 | Yoon et al. |
| 5,449,359 A | 9/1995 | Groiso |
| 5,451,235 A | 9/1995 | Lock et al. |
| 5,456,400 A | 10/1995 | Shichman et al. |
| 5,462,561 A | 10/1995 | Voda |
| 5,464,413 A | 11/1995 | Siska, Jr. et al. |
| 5,466,241 A | 11/1995 | Leroy et al. |
| 5,470,010 A | 11/1995 | Rothfuss et al. |
| 5,471,982 A | 12/1995 | Edwards et al. |
| 5,474,557 A | 12/1995 | Mai |
| 5,474,569 A | 12/1995 | Zinreich et al. |
| 5,476,505 A | 12/1995 | Limon |
| 5,478,352 A | 12/1995 | Fowler |
| 5,478,353 A | 12/1995 | Yoon |
| 5,478,354 A | 12/1995 | Tovey et al. |
| 5,486,186 A | 1/1996 | Yoon |
| 5,486,195 A | 1/1996 | Myers et al. |
| 5,489,288 A | 2/1996 | Buelna |
| 5,492,119 A | 2/1996 | Abrams |
| 5,497,933 A | 3/1996 | DeFonzo et al. |
| 5,507,744 A | 4/1996 | Tay et al. |
| 5,507,755 A | 4/1996 | Gresl et al. |
| 5,522,840 A | 6/1996 | Krajicek |
| 5,527,322 A | 6/1996 | Klein et al. |
| 5,536,251 A | 7/1996 | Evard et al. |
| 5,536,267 A | 7/1996 | Edwards et al. |
| 5,540,712 A | 7/1996 | Kleshinski et al. |
| 5,540,716 A | 7/1996 | Hlavacek |
| 5,544,802 A | 8/1996 | Crainich |
| 5,547,474 A | 8/1996 | Kloeckl et al. |
| 5,560,532 A | 10/1996 | DeFonzo et al. |
| 5,562,684 A | 10/1996 | Kammerer |
| 5,571,120 A | 11/1996 | Yoon |
| 5,573,540 A | 11/1996 | Yoon |
| 5,573,784 A | 11/1996 | Badylak et al. |
| 5,575,771 A | 11/1996 | Walinsky |
| 5,582,616 A | 12/1996 | Bolduc et al. |
| 5,584,879 A | 12/1996 | Reimold et al. |
| 5,591,205 A | 1/1997 | Fowler |
| 5,593,412 A | 1/1997 | Martinez et al. |

(56) References Cited

U.S. PATENT DOCUMENTS

| | | | |
|---|---|---|---|
| 5,601,602 A | 2/1997 | Fowler |
| 5,609,597 A | 3/1997 | Lehrer |
| 5,613,974 A | 3/1997 | Andreas et al. |
| 5,613,975 A | 3/1997 | Christy |
| 5,618,291 A | 4/1997 | Thompson et al. |
| 5,620,452 A | 4/1997 | Yoon |
| 5,620,461 A | 4/1997 | Muijs Van De Moer et al. |
| 5,626,614 A | 5/1997 | Hart |
| 5,634,936 A | 6/1997 | Linden et al. |
| 5,643,318 A | 7/1997 | Tsukernik et al. |
| 5,645,565 A | 7/1997 | Rudd et al. |
| 5,645,566 A | 7/1997 | Brenneman et al. |
| 5,645,567 A | 7/1997 | Crainich |
| 5,647,372 A | 7/1997 | Tovey et al. |
| 5,649,959 A | 7/1997 | Hannam et al. |
| D383,539 S | 9/1997 | Croley |
| 5,669,935 A * | 9/1997 | Rosenman et al. ............ 606/232 |
| 5,672,174 A | 9/1997 | Gough et al. |
| 5,674,231 A | 10/1997 | Green et al. |
| 5,676,689 A | 10/1997 | Kensey et al. |
| 5,676,974 A | 10/1997 | Valdes et al. |
| 5,681,280 A | 10/1997 | Rusk et al. |
| 5,681,334 A | 10/1997 | Evans et al. |
| 5,683,405 A | 11/1997 | Yacoubian et al. |
| 5,690,674 A | 11/1997 | Diaz |
| 5,693,061 A | 12/1997 | Pierce et al. |
| 5,695,504 A | 12/1997 | Gifford, III et al. |
| 5,695,505 A | 12/1997 | Yoon |
| 5,695,524 A | 12/1997 | Kelley et al. |
| 5,700,273 A | 12/1997 | Buelna et al. |
| 5,709,224 A | 1/1998 | Behl et al. |
| 5,713,899 A | 2/1998 | Marnay et al. |
| 5,715,987 A | 2/1998 | Kelley et al. |
| 5,716,375 A | 2/1998 | Fowler |
| 5,720,755 A | 2/1998 | Dakov |
| 5,725,498 A | 3/1998 | Janzen et al. |
| 5,725,552 A | 3/1998 | Kotula et al. |
| 5,725,554 A | 3/1998 | Simon et al. |
| 5,728,110 A | 3/1998 | Vidal et al. |
| 5,728,114 A | 3/1998 | Evans et al. |
| 5,728,116 A | 3/1998 | Rosenman |
| 5,728,122 A | 3/1998 | Leschinsky et al. |
| 5,728,132 A | 3/1998 | Van Tassel et al. |
| 5,728,133 A | 3/1998 | Kontos |
| 5,728,143 A | 3/1998 | Gough et al. |
| 5,732,872 A | 3/1998 | Bolduc et al. |
| 5,735,736 A * | 4/1998 | Volk .............................. 452/176 |
| 5,735,873 A | 4/1998 | MacLean |
| 5,749,826 A | 5/1998 | Faulkner |
| 5,749,898 A | 5/1998 | Schulze et al. |
| 5,752,966 A | 5/1998 | Chang |
| 5,755,726 A | 5/1998 | Pratt et al. |
| 5,755,778 A | 5/1998 | Kleshinski |
| 5,759,189 A | 6/1998 | Ferragamo et al. |
| 5,766,217 A | 6/1998 | Christy |
| 5,766,246 A | 6/1998 | Mulhauser et al. |
| 5,769,870 A | 6/1998 | Salahieh et al. |
| 5,776,147 A | 7/1998 | Dolendo |
| 5,779,707 A | 7/1998 | Bertholet et al. |
| 5,780,807 A | 7/1998 | Saunders |
| 5,782,844 A | 7/1998 | Yoon et al. |
| 5,782,860 A | 7/1998 | Epstein et al. |
| 5,782,861 A | 7/1998 | Cragg et al. |
| 5,792,151 A | 8/1998 | Heck et al. |
| 5,795,958 A | 8/1998 | Rao et al. |
| 5,797,928 A | 8/1998 | Kogasaka |
| 5,797,929 A | 8/1998 | Andreas et al. |
| 5,797,931 A | 8/1998 | Bito et al. |
| 5,797,933 A | 8/1998 | Snow et al. |
| 5,797,958 A | 8/1998 | Yoon |
| 5,797,960 A | 8/1998 | Stevens et al. |
| 5,810,776 A | 9/1998 | Bacich et al. |
| 5,810,845 A | 9/1998 | Yoon |
| 5,810,846 A | 9/1998 | Virnich et al. |
| 5,810,851 A | 9/1998 | Yoon |
| 5,814,052 A | 9/1998 | Nakao et al. |
| 5,817,113 A | 10/1998 | Gifford, III et al. |
| 5,820,631 A | 10/1998 | Nobles |
| 5,827,298 A | 10/1998 | Hart et al. |
| 5,830,125 A | 11/1998 | Scribner et al. |
| 5,830,221 A | 11/1998 | Stein et al. |
| 5,833,698 A | 11/1998 | Hinchliffe et al. |
| 5,843,167 A | 12/1998 | Dwyer et al. |
| 5,845,657 A * | 12/1998 | Carberry et al. ............... 132/273 |
| 5,853,421 A | 12/1998 | Leschinsky et al. |
| 5,853,422 A | 12/1998 | Huebsch et al. |
| 5,855,312 A | 1/1999 | Toledano |
| 5,855,576 A | 1/1999 | LeVeen et al. |
| 5,858,082 A | 1/1999 | Cruz et al. |
| 5,860,991 A | 1/1999 | Klein et al. |
| 5,861,003 A | 1/1999 | Latson et al. |
| 5,861,005 A | 1/1999 | Kontos |
| 5,861,043 A | 1/1999 | Carn |
| 5,865,791 A | 2/1999 | Whayne et al. |
| 5,868,755 A | 2/1999 | Kanner et al. |
| 5,868,762 A | 2/1999 | Cragg et al. |
| 5,868,763 A | 2/1999 | Spence et al. |
| 5,871,474 A | 2/1999 | Hermann et al. |
| 5,871,501 A | 2/1999 | Leschinsky et al. |
| 5,871,525 A | 2/1999 | Edwards et al. |
| 5,873,876 A | 2/1999 | Christy |
| 5,873,891 A | 2/1999 | Sohn |
| 5,879,366 A | 3/1999 | Shaw et al. |
| 5,891,088 A | 4/1999 | Thompson et al. |
| 5,897,487 A | 4/1999 | Ouchi |
| 5,902,310 A | 5/1999 | Foerster et al. |
| 5,904,697 A | 5/1999 | Gifford, III et al. |
| 5,906,620 A | 5/1999 | Nakao et al. |
| 5,906,631 A | 5/1999 | Imran |
| 5,907,893 A | 6/1999 | Zadno-Azizi et al. |
| 5,910,155 A | 6/1999 | Ratcliff et al. |
| 5,919,207 A | 7/1999 | Taheri |
| 5,922,009 A | 7/1999 | Epstein et al. |
| 5,928,231 A | 7/1999 | Klein et al. |
| 5,928,251 A | 7/1999 | Aranyi et al. |
| 5,935,147 A | 8/1999 | Kensey et al. |
| 5,938,667 A | 8/1999 | Peyser et al. |
| 5,941,890 A | 8/1999 | Voegele et al. |
| 5,944,728 A | 8/1999 | Bates |
| 5,947,999 A | 9/1999 | Groiso |
| 5,948,001 A | 9/1999 | Larsen |
| 5,951,518 A | 9/1999 | Licata et al. |
| 5,951,547 A | 9/1999 | Gough et al. |
| 5,951,575 A | 9/1999 | Bolduc et al. |
| 5,951,576 A | 9/1999 | Wakabayashi |
| 5,951,589 A | 9/1999 | Epstein et al. |
| 5,957,900 A | 9/1999 | Ouchi |
| 5,957,936 A | 9/1999 | Yoon et al. |
| 5,957,938 A | 9/1999 | Zhu et al. |
| 5,957,940 A | 9/1999 | Tanner et al. |
| 5,964,782 A | 10/1999 | Lafontaine et al. |
| 5,972,009 A | 10/1999 | Fortier et al. |
| 5,972,034 A | 10/1999 | Hofmann et al. |
| 5,976,161 A | 11/1999 | Kirsch et al. |
| 5,976,174 A | 11/1999 | Ruiz |
| 5,980,517 A | 11/1999 | Gough |
| 5,984,934 A | 11/1999 | Ashby et al. |
| 5,984,948 A | 11/1999 | Hasson |
| 5,984,949 A | 11/1999 | Levin |
| 5,984,950 A | 11/1999 | Cragg et al. |
| 5,993,466 A | 11/1999 | Yoon |
| 5,993,468 A | 11/1999 | Rygaard |
| 5,993,476 A | 11/1999 | Groiso |
| 6,001,110 A | 12/1999 | Adams |
| 6,004,341 A | 12/1999 | Zhu et al. |
| 6,007,563 A | 12/1999 | Nash et al. |
| 6,009,877 A | 1/2000 | Edwards |
| 6,010,517 A | 1/2000 | Baccaro |
| 6,013,084 A | 1/2000 | Ken et al. |
| 6,015,815 A | 1/2000 | Mollison |
| 6,019,779 A | 2/2000 | Thorud et al. |
| 6,022,372 A | 2/2000 | Kontos |
| 6,024,747 A | 2/2000 | Kontos |
| 6,024,750 A | 2/2000 | Mastri |

(56) References Cited

U.S. PATENT DOCUMENTS

| | | |
|---|---|---|
| 6,024,756 A | 2/2000 | Huebsch et al. |
| 6,030,364 A | 2/2000 | Durgin et al. |
| 6,030,413 A | 2/2000 | Lazarus |
| 6,033,427 A | 3/2000 | Lee |
| 6,036,703 A | 3/2000 | Evans et al. |
| 6,036,720 A | 3/2000 | Abrams et al. |
| 6,045,570 A | 4/2000 | Epstein et al. |
| 6,048,358 A | 4/2000 | Barak |
| 6,056,744 A | 5/2000 | Edwards |
| 6,056,768 A | 5/2000 | Cates et al. |
| 6,056,769 A | 5/2000 | Epstein et al. |
| 6,056,770 A | 5/2000 | Epstein et al. |
| 6,059,719 A | 5/2000 | Yamamoto et al. |
| 6,059,800 A | 5/2000 | Hart et al. |
| 6,059,825 A | 5/2000 | Hobbs et al. |
| 6,063,085 A | 5/2000 | Tay et al. |
| 6,063,114 A | 5/2000 | Nash et al. |
| 6,068,603 A | 5/2000 | Suzuki |
| 6,071,300 A | 6/2000 | Brenneman et al. |
| 6,077,281 A | 6/2000 | Das |
| 6,077,291 A | 6/2000 | Das |
| 6,080,182 A | 6/2000 | Shaw et al. |
| 6,080,183 A | 6/2000 | Tsugita et al. |
| 6,083,242 A | 7/2000 | Cook |
| 6,090,130 A | 7/2000 | Nash et al. |
| 6,095,155 A * | 8/2000 | Criscuolo ................. 132/278 |
| 6,102,271 A | 8/2000 | Longo et al. |
| 6,110,184 A | 8/2000 | Weadock |
| 6,113,610 A | 9/2000 | Poncet |
| 6,113,612 A | 9/2000 | Swanson et al. |
| 6,117,125 A | 9/2000 | Rothbarth et al. |
| 6,117,148 A | 9/2000 | Ravo |
| 6,117,157 A | 9/2000 | Tekulve |
| 6,117,159 A | 9/2000 | Huebsch et al. |
| 6,120,513 A * | 9/2000 | Bailey et al. ................ 606/141 |
| 6,120,524 A | 9/2000 | Taheri |
| 6,126,675 A | 10/2000 | Shchervinsky et al. |
| 6,136,010 A | 10/2000 | Modesitt et al. |
| 6,143,004 A | 11/2000 | Davis et al. |
| 6,146,385 A | 11/2000 | Torrie et al. |
| 6,149,660 A | 11/2000 | Laufer et al. |
| 6,149,667 A | 11/2000 | Hovland et al. |
| 6,152,144 A | 11/2000 | Lesh et al. |
| 6,152,936 A | 11/2000 | Christy et al. |
| 6,152,937 A | 11/2000 | Peterson et al. |
| 6,161,263 A * | 12/2000 | Anderson ................. 24/545 |
| 6,165,204 A | 12/2000 | Levinson et al. |
| 6,171,277 B1 | 1/2001 | Ponzi |
| 6,171,329 B1 | 1/2001 | Shaw et al. |
| 6,174,322 B1 | 1/2001 | Schneidt |
| 6,178,355 B1 | 1/2001 | Williams et al. |
| 6,179,849 B1 | 1/2001 | Yencho et al. |
| 6,179,860 B1 | 1/2001 | Fulton, III et al. |
| 6,193,708 B1 | 2/2001 | Ken et al. |
| 6,193,734 B1 | 2/2001 | Bolduc et al. |
| 6,197,042 B1 | 3/2001 | Ginn et al. |
| 6,198,974 B1 | 3/2001 | Webster, Jr. |
| 6,200,329 B1 | 3/2001 | Fung et al. |
| 6,200,330 B1 | 3/2001 | Benderev et al. |
| 6,206,895 B1 | 3/2001 | Levinson |
| 6,206,913 B1 | 3/2001 | Yencho et al. |
| 6,206,931 B1 | 3/2001 | Cook et al. |
| 6,210,407 B1 | 4/2001 | Webster |
| 6,220,248 B1 | 4/2001 | Voegele et al. |
| 6,221,084 B1 | 4/2001 | Fleenor |
| 6,221,102 B1 | 4/2001 | Baker et al. |
| 6,231,561 B1 | 5/2001 | Frazier et al. |
| 6,245,079 B1 | 6/2001 | Nobles et al. |
| 6,248,124 B1 | 6/2001 | Pedros et al. |
| 6,254,617 B1 | 7/2001 | Spence et al. |
| 6,254,642 B1 | 7/2001 | Taylor |
| 6,258,115 B1 | 7/2001 | Dubrul |
| 6,267,773 B1 | 7/2001 | Gadberry et al. |
| 6,273,903 B1 | 8/2001 | Wilk |
| 6,277,140 B2 | 8/2001 | Ginn et al. |
| 6,280,460 B1 | 8/2001 | Bolduc et al. |
| 6,287,322 B1 | 9/2001 | Zhu et al. |
| 6,296,657 B1 | 10/2001 | Brucker |
| 6,302,898 B1 | 10/2001 | Edwards et al. |
| 6,305,891 B1 | 10/2001 | Burlingame |
| 6,306,081 B1 | 10/2001 | Ishikawa et al. |
| 6,309,416 B1 | 10/2001 | Swanson et al. |
| 6,315,782 B1 | 11/2001 | Chu et al. |
| 6,319,258 B1 | 11/2001 | McAllen, III et al. |
| 6,322,580 B1 | 11/2001 | Kanner |
| 6,328,727 B1 | 12/2001 | Frazier et al. |
| 6,329,386 B1 | 12/2001 | Mollison |
| 6,334,865 B1 | 1/2002 | Redmond et al. |
| 6,348,064 B1 | 2/2002 | Kanner |
| 6,355,052 B1 | 3/2002 | Neuss et al. |
| 6,358,258 B1 | 3/2002 | Arcia et al. |
| 6,375,671 B1 | 4/2002 | Kobayashi et al. |
| D457,958 S | 5/2002 | Dycus |
| 6,383,208 B1 | 5/2002 | Sancoff et al. |
| 6,391,048 B1 | 5/2002 | Ginn et al. |
| 6,395,015 B1 | 5/2002 | Borst et al. |
| 6,397,110 B1 | 5/2002 | Kuzma |
| 6,398,752 B1 | 6/2002 | Sweezer et al. |
| 6,402,765 B1 | 6/2002 | Monassevitch et al. |
| 6,409,739 B1 | 6/2002 | Nobles et al. |
| 6,419,669 B1 | 7/2002 | Frazier et al. |
| 6,421,899 B1 | 7/2002 | Zitnay |
| 6,423,054 B1 | 7/2002 | Ouchi |
| 6,425,911 B1 | 7/2002 | Akerfeldt et al. |
| 6,428,472 B1 | 8/2002 | Haas |
| 6,428,548 B1 | 8/2002 | Durgin et al. |
| 6,443,158 B1 | 9/2002 | Lafontaine et al. |
| 6,443,963 B1 | 9/2002 | Baldwin et al. |
| 6,447,540 B1 | 9/2002 | Fontaine et al. |
| 6,450,391 B1 | 9/2002 | Kayan et al. |
| 6,458,130 B1 | 10/2002 | Frazier et al. |
| 6,461,364 B1 | 10/2002 | Ginn et al. |
| 6,461,366 B1 | 10/2002 | Seguin |
| 6,482,224 B1 | 11/2002 | Michler et al. |
| 6,488,692 B1 | 12/2002 | Spence et al. |
| 6,500,115 B2 | 12/2002 | Krattiger et al. |
| 6,506,209 B2 | 1/2003 | Ouchi |
| 6,506,210 B1 | 1/2003 | Kanner |
| 6,508,828 B1 | 1/2003 | Akerfeldt et al. |
| 6,514,280 B1 | 2/2003 | Gilson |
| 6,517,498 B1 | 2/2003 | Burbank et al. |
| 6,517,555 B1 | 2/2003 | Caro |
| 6,517,569 B2 | 2/2003 | Mikus et al. |
| 6,527,737 B2 | 3/2003 | Kaneshige |
| 6,533,762 B2 | 3/2003 | Kanner et al. |
| 6,533,812 B2 | 3/2003 | Swanson et al. |
| 6,537,288 B2 | 3/2003 | Vargas et al. |
| 6,547,806 B1 | 4/2003 | Ding |
| 6,551,319 B2 | 4/2003 | Lieberman |
| 6,558,349 B1 | 5/2003 | Kirkman |
| 6,569,159 B1 | 5/2003 | Edwards et al. |
| 6,569,173 B1 | 5/2003 | Blatter et al. |
| 6,569,185 B2 | 5/2003 | Ungs |
| 6,572,629 B2 | 6/2003 | Kalloo et al. |
| 6,578,585 B1 * | 6/2003 | Stachowski et al. .......... 132/273 |
| 6,582,452 B2 | 6/2003 | Coleman et al. |
| 6,582,482 B2 | 6/2003 | Gillman et al. |
| 6,596,012 B2 | 7/2003 | Akerfeldt et al. |
| 6,599,303 B1 | 7/2003 | Peterson et al. |
| 6,599,311 B1 | 7/2003 | Biggs et al. |
| 6,602,263 B1 | 8/2003 | Swanson et al. |
| 6,610,072 B1 | 8/2003 | Christy et al. |
| 6,613,059 B2 | 9/2003 | Schaller et al. |
| 6,613,060 B2 * | 9/2003 | Adams et al. ................ 606/157 |
| 6,616,686 B2 | 9/2003 | Coleman et al. |
| 6,620,165 B2 | 9/2003 | Wellisz |
| 6,623,509 B2 | 9/2003 | Ginn |
| 6,623,510 B2 | 9/2003 | Carley et al. |
| 6,626,918 B1 | 9/2003 | Ginn et al. |
| 6,626,919 B1 | 9/2003 | Swanstrom |
| 6,626,920 B2 | 9/2003 | Whayne |
| 6,632,197 B2 | 10/2003 | Lyon |
| 6,632,238 B2 | 10/2003 | Ginn et al. |
| 6,634,537 B2 | 10/2003 | Chen |

(56) References Cited

U.S. PATENT DOCUMENTS

| | | |
|---|---|---|
| 6,645,205 B2 | 11/2003 | Ginn |
| 6,645,225 B1 | 11/2003 | Atkinson |
| 6,652,538 B2 | 11/2003 | Kayan et al. |
| 6,652,556 B1 | 11/2003 | VanTassel et al. |
| 6,663,633 B1 | 12/2003 | Pierson, III |
| 6,663,655 B2 | 12/2003 | Ginn et al. |
| 6,669,714 B2 | 12/2003 | Coleman et al. |
| 6,673,083 B1 | 1/2004 | Kayan et al. |
| 6,676,671 B2 | 1/2004 | Robertson et al. |
| 6,676,685 B2 * | 1/2004 | Pedros et al. ............... 606/213 |
| 6,679,904 B2 | 1/2004 | Gleeson et al. |
| 6,685,707 B2 | 2/2004 | Roman et al. |
| 6,689,051 B2 | 2/2004 | Nakada et al. |
| 6,689,147 B1 | 2/2004 | Koster, Jr. |
| 6,695,867 B2 * | 2/2004 | Ginn et al. ................ 606/213 |
| 6,699,256 B1 | 3/2004 | Logan et al. |
| 6,702,826 B2 | 3/2004 | Liddicoat et al. |
| 6,712,836 B1 | 3/2004 | Berg et al. |
| 6,712,837 B2 | 3/2004 | Akerfeldt et al. |
| 6,719,777 B2 | 4/2004 | Ginn et al. |
| 6,726,704 B1 | 4/2004 | Loshakove et al. |
| 6,736,822 B2 * | 5/2004 | McClellan et al. .......... 606/139 |
| 6,743,195 B2 | 6/2004 | Zucker |
| 6,743,243 B1 | 6/2004 | Roy et al. |
| 6,743,259 B2 | 6/2004 | Ginn |
| 6,745,079 B2 | 6/2004 | King |
| 6,746,457 B2 | 6/2004 | Dana et al. |
| 6,746,472 B2 | 6/2004 | Frazier et al. |
| 6,749,621 B2 * | 6/2004 | Pantages et al. ............. 606/213 |
| 6,749,622 B2 | 6/2004 | McGuckin, Jr. et al. |
| 6,752,813 B2 | 6/2004 | Goldfarb et al. |
| 6,755,842 B2 | 6/2004 | Kanner et al. |
| 6,767,356 B2 | 7/2004 | Kanner et al. |
| 6,776,785 B1 | 8/2004 | Yencho et al. |
| 6,780,197 B2 | 8/2004 | Roe et al. |
| 6,786,915 B2 | 9/2004 | Akerfeldt et al. |
| 6,790,218 B2 | 9/2004 | Jayaraman |
| 6,790,220 B2 | 9/2004 | Morris et al. |
| 6,837,893 B2 | 1/2005 | Miller |
| 6,837,906 B2 | 1/2005 | Ginn |
| 6,846,319 B2 | 1/2005 | Ginn et al. |
| 6,849,078 B2 * | 2/2005 | Durgin et al. ............... 606/142 |
| 6,860,895 B1 | 3/2005 | Akerfeldt et al. |
| 6,890,343 B2 | 5/2005 | Ginn et al. |
| 6,896,687 B2 | 5/2005 | Dakov |
| 6,896,692 B2 | 5/2005 | Ginn et al. |
| 6,904,647 B2 * | 6/2005 | Byers, Jr. .................... 24/30.5 R |
| 6,913,607 B2 | 7/2005 | Ainsworth et al. |
| 6,926,723 B1 | 8/2005 | Mulhauser et al. |
| 6,926,731 B2 | 8/2005 | Coleman et al. |
| 6,929,634 B2 | 8/2005 | Dorros et al. |
| 6,942,641 B2 | 9/2005 | Seddon |
| 6,942,674 B2 * | 9/2005 | Belef et al. .................. 606/142 |
| 6,942,691 B1 | 9/2005 | Chuter |
| 6,964,668 B2 | 11/2005 | Modesitt et al. |
| 6,969,397 B2 | 11/2005 | Ginn |
| 6,984,238 B2 * | 1/2006 | Gifford et al. ............... 606/155 |
| 6,989,003 B2 | 1/2006 | Wing et al. |
| 6,989,016 B2 | 1/2006 | Tallarida et al. |
| 7,001,398 B2 | 2/2006 | Carley et al. |
| 7,001,400 B1 | 2/2006 | Modesitt et al. |
| 7,008,435 B2 | 3/2006 | Cummins |
| 7,008,439 B1 | 3/2006 | Janzen et al. |
| 7,025,776 B1 | 4/2006 | Houser et al. |
| 7,033,379 B2 | 4/2006 | Peterson |
| 7,048,747 B2 | 5/2006 | Arcia et al. |
| 7,060,084 B1 | 6/2006 | Loshakove et al. |
| 7,063,661 B2 | 6/2006 | Okada |
| 7,063,711 B1 | 6/2006 | Loshakove et al. |
| 7,074,232 B2 | 7/2006 | Kanner et al. |
| 7,076,305 B2 | 7/2006 | Imran et al. |
| 7,083,635 B2 | 8/2006 | Ginn |
| 7,087,064 B1 | 8/2006 | Hyde |
| 7,108,709 B2 | 9/2006 | Cummins |
| 7,111,768 B2 | 9/2006 | Cummins et al. |
| 7,112,225 B2 | 9/2006 | Ginn |
| 7,122,002 B2 | 10/2006 | Okada |
| 7,144,411 B2 | 12/2006 | Ginn et al. |
| 7,147,646 B2 | 12/2006 | Dana et al. |
| 7,163,551 B2 | 1/2007 | Anthony et al. |
| 7,169,158 B2 | 1/2007 | Sniffin et al. |
| 7,169,164 B2 | 1/2007 | Borillo et al. |
| 7,211,101 B2 | 5/2007 | Carley et |
| 7,229,452 B2 | 6/2007 | Kayan |
| 7,261,716 B2 | 8/2007 | Strobel et al. |
| 7,270,672 B1 | 9/2007 | Singer |
| 7,306,614 B2 | 12/2007 | Weller et al. |
| 7,311,720 B2 | 12/2007 | Mueller et al. |
| 7,316,704 B2 | 1/2008 | Bagaoisan et al. |
| 7,316,706 B2 | 1/2008 | Bloom et al. |
| 7,322,995 B2 | 1/2008 | Buckman et al. |
| 7,326,230 B2 | 2/2008 | Ravikumar |
| 7,331,979 B2 | 2/2008 | Khosravi et al. |
| 7,335,220 B2 | 2/2008 | Khosravi et al. |
| 7,338,514 B2 | 3/2008 | Wahr et al. |
| D566,272 S | 4/2008 | Walburg et al. |
| 7,361,178 B2 | 4/2008 | Hearn et al. |
| 7,361,183 B2 | 4/2008 | Ginn |
| 7,361,185 B2 | 4/2008 | O'Malley et al. |
| 7,393,363 B2 | 7/2008 | Ginn |
| 7,396,359 B1 | 7/2008 | Derowe et al. |
| 7,431,727 B2 | 10/2008 | Cole et al. |
| 7,431,729 B2 | 10/2008 | Chanduszko |
| 7,465,286 B2 | 12/2008 | Patterson et al. |
| 7,507,200 B2 | 3/2009 | Okada |
| 7,533,790 B1 | 5/2009 | Knodel et al. |
| 7,582,103 B2 | 9/2009 | Young et al. |
| 7,582,104 B2 | 9/2009 | Corcoran et al. |
| 7,597,706 B2 | 10/2009 | Kanner et al. |
| 7,618,427 B2 | 11/2009 | Ortiz et al. |
| 7,622,628 B2 | 11/2009 | Bergin et al. |
| 7,645,285 B2 * | 1/2010 | Cosgrove et al. ............ 606/151 |
| 7,648,493 B2 | 1/2010 | Forsberg et al. |
| D611,144 S | 3/2010 | Reynolds |
| 7,678,135 B2 | 3/2010 | Maahs et al. |
| 7,727,249 B2 | 6/2010 | Rahmani |
| 7,731,655 B2 | 6/2010 | Smith et al. |
| 7,749,249 B2 | 7/2010 | Gelbart et al. |
| 7,780,696 B2 | 8/2010 | Daniel et al. |
| 7,799,042 B2 * | 9/2010 | Williamson et al. .......... 606/157 |
| 7,806,904 B2 | 10/2010 | Carley et al. |
| 7,819,895 B2 | 10/2010 | Ginn et al. |
| 7,841,502 B2 | 11/2010 | Walberg et al. |
| 7,842,068 B2 | 11/2010 | Ginn |
| 7,850,709 B2 | 12/2010 | Cummins et al. |
| 7,850,797 B2 | 12/2010 | Carley et al. |
| 7,854,810 B2 | 12/2010 | Carley et al. |
| 7,857,828 B2 | 12/2010 | Jabba et al. |
| 7,867,249 B2 | 1/2011 | Palermo et al. |
| 7,879,071 B2 | 2/2011 | Carley et al. |
| 7,887,555 B2 | 2/2011 | Carley et al. |
| 7,887,563 B2 | 2/2011 | Cummins et al. |
| 7,901,428 B2 | 3/2011 | Ginn et al. |
| 7,905,900 B2 | 3/2011 | Palermo |
| 7,918,873 B2 | 4/2011 | Cummins et al. |
| 7,931,669 B2 | 4/2011 | Ginn et al. |
| 7,931,671 B2 | 4/2011 | Tenerz |
| 7,967,842 B2 | 6/2011 | Bakos |
| 8,007,504 B2 | 8/2011 | Zenati et al. |
| 8,007,512 B2 | 8/2011 | Ginn et al. |
| 8,083,768 B2 | 12/2011 | Ginn et al. |
| 8,103,327 B2 | 1/2012 | Harlev et al. |
| 8,105,352 B2 | 1/2012 | Egnelöv |
| 8,128,644 B2 | 3/2012 | Carley et al. |
| 8,182,497 B2 | 5/2012 | Carley et al. |
| 8,192,459 B2 | 6/2012 | Cummins et al. |
| 8,202,283 B2 | 6/2012 | Carley et al. |
| 8,202,293 B2 | 6/2012 | Ellingwood et al. |
| 8,202,294 B2 | 6/2012 | Jabba et al. |
| 8,226,666 B2 * | 7/2012 | Zarbatany et al. ............ 606/139 |
| 8,226,681 B2 | 7/2012 | Clark et al. |
| 8,236,026 B2 | 8/2012 | Carley et al. |
| 8,257,390 B2 | 9/2012 | Carley et al. |
| 8,303,624 B2 | 11/2012 | Fortson |

(56) References Cited

U.S. PATENT DOCUMENTS

| | | | |
|---|---|---|---|
| 8,323,312 B2 | 12/2012 | Clark | |
| 8,398,656 B2 | 3/2013 | Palermo et al. | |
| 8,398,676 B2 | 3/2013 | Roorda et al. | |
| 8,469,969 B2 | 6/2013 | Kear et al. | |
| 8,469,995 B2 | 6/2013 | Cummins et al. | |
| 8,480,687 B2 | 7/2013 | Ducharme et al. | |
| 8,486,092 B2 | 7/2013 | Carley et al. | |
| 8,486,108 B2 | 7/2013 | Carley et al. | |
| 2001/0007077 A1 | 7/2001 | Ginn et al. | |
| 2001/0031972 A1 | 10/2001 | Robertson et al. | |
| 2001/0031973 A1 | 10/2001 | Nobles et al. | |
| 2001/0044639 A1 | 11/2001 | Levinson | |
| 2001/0046518 A1 | 11/2001 | Sawhney | |
| 2001/0047180 A1 | 11/2001 | Grudem et al. | |
| 2001/0053909 A1* | 12/2001 | Nakada et al. | 606/47 |
| 2002/0022822 A1 | 2/2002 | Cragg et al. | |
| 2002/0026215 A1 | 2/2002 | Redmond et al. | |
| 2002/0026216 A1 | 2/2002 | Grimes | |
| 2002/0029050 A1 | 3/2002 | Gifford, III et al. | |
| 2002/0038127 A1 | 3/2002 | Blatter et al. | |
| 2002/0042622 A1 | 4/2002 | Vargas et al. | |
| 2002/0049427 A1 | 4/2002 | Wiener et al. | |
| 2002/0058960 A1 | 5/2002 | Hudson et al. | |
| 2002/0062104 A1 | 5/2002 | Ashby et al. | |
| 2002/0077657 A1 | 6/2002 | Ginn et al. | |
| 2002/0082641 A1 | 6/2002 | Ginn et al. | |
| 2002/0095181 A1 | 7/2002 | Beyar | |
| 2002/0099389 A1 | 7/2002 | Michler et al. | |
| 2002/0106409 A1 | 8/2002 | Sawhney et al. | |
| 2002/0107542 A1 | 8/2002 | Kanner et al. | |
| 2002/0151921 A1 | 10/2002 | Kanner et al. | |
| 2002/0151963 A1 | 10/2002 | Brown et al. | |
| 2002/0183786 A1 | 12/2002 | Girton | |
| 2002/0183787 A1 | 12/2002 | Wahr et al. | |
| 2002/0188275 A1 | 12/2002 | McGuckin, Jr. | |
| 2002/0198562 A1 | 12/2002 | Akerfeldt et al. | |
| 2002/0198589 A1 | 12/2002 | Leong | |
| 2003/0004543 A1 | 1/2003 | Gleeson et al. | |
| 2003/0009180 A1 | 1/2003 | Hinchliffe et al. | |
| 2003/0018358 A1 | 1/2003 | Saadat | |
| 2003/0023248 A1 | 1/2003 | Parodi | |
| 2003/0032981 A1 | 2/2003 | Kanner et al. | |
| 2003/0033006 A1 | 2/2003 | Phillips et al. | |
| 2003/0045893 A1 | 3/2003 | Ginn | |
| 2003/0055455 A1 | 3/2003 | Yang et al. | |
| 2003/0060846 A1 | 3/2003 | Egnelov et al. | |
| 2003/0065358 A1 | 4/2003 | Frecker et al. | |
| 2003/0083679 A1 | 5/2003 | Grudem et al. | |
| 2003/0093096 A1 | 5/2003 | McGuckin et al. | |
| 2003/0093108 A1 | 5/2003 | Avellanet et al. | |
| 2003/0097140 A1 | 5/2003 | Kanner | |
| 2003/0109890 A1 | 6/2003 | Kanner et al. | |
| 2003/0125766 A1 | 7/2003 | Ding | |
| 2003/0139819 A1 | 7/2003 | Beer et al. | |
| 2003/0144695 A1 | 7/2003 | McGuckin, Jr. et al. | |
| 2003/0158577 A1 | 8/2003 | Pantages et al. | |
| 2003/0158578 A1 | 8/2003 | Pantages et al. | |
| 2003/0187457 A1 | 10/2003 | Weber | |
| 2003/0195504 A1 | 10/2003 | Tallarida et al. | |
| 2003/0208211 A1 | 11/2003 | Kortenbach | |
| 2003/0233095 A1 | 12/2003 | Urbanski et al. | |
| 2004/0009205 A1 | 1/2004 | Sawhney | |
| 2004/0044350 A1 | 3/2004 | Martin et al. | |
| 2004/0049224 A1 | 3/2004 | Buehlmann et al. | |
| 2004/0059376 A1 | 3/2004 | Breuniger | |
| 2004/0068273 A1 | 4/2004 | Fariss et al. | |
| 2004/0078053 A1 | 4/2004 | Berg et al. | |
| 2004/0082906 A1 | 4/2004 | Tallarida et al. | |
| 2004/0087985 A1 | 5/2004 | Loshakove et al. | |
| 2004/0092962 A1 | 5/2004 | Thornton et al. | |
| 2004/0092964 A1 | 5/2004 | Modesitt et al. | |
| 2004/0092968 A1 | 5/2004 | Caro et al. | |
| 2004/0092973 A1 | 5/2004 | Chanduszko et al. | |
| 2004/0093024 A1 | 5/2004 | Lousararian et al. | |
| 2004/0093027 A1 | 5/2004 | Fabisiak et al. | |
| 2004/0097978 A1 | 5/2004 | Modesitt et al. | |
| 2004/0098044 A1 | 5/2004 | Van de Moer et al. | |
| 2004/0106980 A1 | 6/2004 | Solovay et al. | |
| 2004/0116943 A1 | 6/2004 | Brandt et al. | |
| 2004/0122349 A1 | 6/2004 | Lafontaine et al. | |
| 2004/0127940 A1 | 7/2004 | Ginn et al. | |
| 2004/0143290 A1 | 7/2004 | Brightbill | |
| 2004/0143291 A1 | 7/2004 | Corcoran et al. | |
| 2004/0158127 A1 | 8/2004 | Okada | |
| 2004/0158287 A1 | 8/2004 | Cragg et al. | |
| 2004/0158309 A1 | 8/2004 | Wachter et al. | |
| 2004/0167511 A1 | 8/2004 | Buehlmann et al. | |
| 2004/0167570 A1 | 8/2004 | Pantages | |
| 2004/0191277 A1 | 9/2004 | Sawhney et al. | |
| 2004/0215232 A1 | 10/2004 | Belhe et al. | |
| 2004/0225194 A1 | 11/2004 | Smith et al. | |
| 2004/0236354 A1 | 11/2004 | Seguin | |
| 2004/0243216 A1 | 12/2004 | Gregorich | |
| 2004/0249412 A1 | 12/2004 | Snow et al. | |
| 2004/0254591 A1 | 12/2004 | Kanner et al. | |
| 2004/0267193 A1 | 12/2004 | Bagaoisan et al. | |
| 2004/0267308 A1 | 12/2004 | Bagaoisan et al. | |
| 2004/0267312 A1 | 12/2004 | Kanner et al. | |
| 2005/0010248 A1 | 1/2005 | Lafontaine | |
| 2005/0033359 A1 | 2/2005 | Dycus | |
| 2005/0038460 A1 | 2/2005 | Jayaraman | |
| 2005/0038500 A1 | 2/2005 | Boylan et al. | |
| 2005/0059982 A1 | 3/2005 | Zung et al. | |
| 2005/0075654 A1 | 4/2005 | Kelleher | |
| 2005/0075665 A1 | 4/2005 | Brenzel et al. | |
| 2005/0085851 A1 | 4/2005 | Fiehler et al. | |
| 2005/0085854 A1 | 4/2005 | Ginn | |
| 2005/0085855 A1 | 4/2005 | Forsberg | |
| 2005/0090859 A1 | 4/2005 | Ravlkumar | |
| 2005/0119695 A1 | 6/2005 | Carley et al. | |
| 2005/0121042 A1 | 6/2005 | Belhe et al. | |
| 2005/0149065 A1 | 7/2005 | Modesitt | |
| 2005/0149117 A1 | 7/2005 | Khosravi et al. | |
| 2005/0152949 A1 | 7/2005 | Hotchkiss et al. | |
| 2005/0154401 A1 | 7/2005 | Weldon et al. | |
| 2005/0165357 A1 | 7/2005 | McGuckin et al. | |
| 2005/0169974 A1 | 8/2005 | Tenerz et al. | |
| 2005/0177189 A1 | 8/2005 | Ginn et al. | |
| 2005/0187564 A1 | 8/2005 | Jayaraman | |
| 2005/0203552 A1 | 9/2005 | Laufer et al. | |
| 2005/0216057 A1 | 9/2005 | Coleman et al. | |
| 2005/0222614 A1 | 10/2005 | Ginn et al. | |
| 2005/0228443 A1 | 10/2005 | Yassinzadeh | |
| 2005/0234396 A1 | 10/2005 | Forsberg et al. | |
| 2005/0245876 A1 | 11/2005 | Khosravi et al. | |
| 2005/0256532 A1 | 11/2005 | Nayak et al. | |
| 2005/0261708 A1 | 11/2005 | Pasricha et al. | |
| 2005/0267528 A1 | 12/2005 | Ginn et al. | |
| 2005/0273136 A1 | 12/2005 | Belef et al. | |
| 2005/0273137 A1 | 12/2005 | Ginn | |
| 2005/0274768 A1 | 12/2005 | Cummins et al. | |
| 2005/0283188 A1 | 12/2005 | Loshakove et al. | |
| 2006/0030867 A1 | 2/2006 | Zadno | |
| 2006/0034930 A1 | 2/2006 | Khosravi et al. | |
| 2006/0047313 A1 | 3/2006 | Khanna et al. | |
| 2006/0058844 A1* | 3/2006 | White et al. | 606/232 |
| 2006/0064115 A1 | 3/2006 | Allen et al. | |
| 2006/0089635 A1 | 4/2006 | Young et al. | |
| 2006/0095029 A1 | 5/2006 | Young et al. | |
| 2006/0100664 A1 | 5/2006 | Pai et al. | |
| 2006/0106420 A1 | 5/2006 | Dolan et al. | |
| 2006/0142784 A1 | 6/2006 | Kontos | |
| 2006/0190014 A1 | 8/2006 | Ginn et al. | |
| 2006/0190036 A1 | 8/2006 | Wendel et al. | |
| 2006/0190037 A1 | 8/2006 | Ginn et al. | |
| 2006/0195123 A1 | 8/2006 | Ginn et al. | |
| 2006/0195124 A1 | 8/2006 | Ginn et al. | |
| 2006/0206146 A1 | 9/2006 | Tenerz | |
| 2006/0253037 A1 | 11/2006 | Ginn et al. | |
| 2006/0253072 A1 | 11/2006 | Pai et al. | |
| 2006/0259049 A1 | 11/2006 | Harada et al. | |
| 2006/0287674 A1 | 12/2006 | Ginn et al. | |
| 2006/0293698 A1 | 12/2006 | Douk | |
| 2007/0005093 A1 | 1/2007 | Cox | |

(56) References Cited

U.S. PATENT DOCUMENTS

| | | |
|---|---|---|
| 2007/0010853 A1 | 1/2007 | Ginn et al. |
| 2007/0021778 A1 | 1/2007 | Carly |
| 2007/0027525 A1 | 2/2007 | Ben-Muvhar |
| 2007/0049967 A1 | 3/2007 | Sibbitt, Jr. et al. |
| 2007/0049968 A1* | 3/2007 | Sibbitt et al. .................. 606/213 |
| 2007/0049970 A1 | 3/2007 | Belef et al. |
| 2007/0060895 A1 | 3/2007 | Sibbitt, Jr. et al. |
| 2007/0060950 A1 | 3/2007 | Khosravi et al. |
| 2007/0060951 A1* | 3/2007 | Shannon ....................... 606/216 |
| 2007/0083230 A1 | 4/2007 | Javois |
| 2007/0083231 A1 | 4/2007 | Lee |
| 2007/0112304 A1 | 5/2007 | Voss |
| 2007/0112365 A1 | 5/2007 | Hilal et al. |
| 2007/0112385 A1 | 5/2007 | Conlon |
| 2007/0123816 A1 | 5/2007 | Zhu et al. |
| 2007/0123817 A1 | 5/2007 | Khosravi et al. |
| 2007/0123936 A1* | 5/2007 | Goldin et al. ................. 606/232 |
| 2007/0172430 A1 | 7/2007 | Brito et al. |
| 2007/0179527 A1 | 8/2007 | Eskuri et al. |
| 2007/0185530 A1 | 8/2007 | Chin-Chen et al. |
| 2007/0198058 A1 | 8/2007 | Gelbart et al. |
| 2007/0203506 A1 | 8/2007 | Sibbitt, Jr. et al. |
| 2007/0203507 A1 | 8/2007 | McLaughlin et al. |
| 2007/0213747 A1* | 9/2007 | Monassevitch et al. ...... 606/151 |
| 2007/0225755 A1 | 9/2007 | Preinitz et al. |
| 2007/0225756 A1 | 9/2007 | Preinitz et al. |
| 2007/0225757 A1 | 9/2007 | Preinitz et al. |
| 2007/0225758 A1 | 9/2007 | Preinitz et al. |
| 2007/0239209 A1 | 10/2007 | Fallman |
| 2007/0250080 A1 | 10/2007 | Jones et al. |
| 2007/0265658 A1 | 11/2007 | Nelson et al. |
| 2007/0270904 A1 | 11/2007 | Ginn |
| 2007/0275036 A1 | 11/2007 | Green, III et al. |
| 2007/0276488 A1 | 11/2007 | Wachter et al. |
| 2007/0282352 A1 | 12/2007 | Carley et al. |
| 2007/0282373 A1 | 12/2007 | Ashby et al. |
| 2008/0004636 A1* | 1/2008 | Walberg et al. ............... 606/142 |
| 2008/0004640 A1 | 1/2008 | Ellingwood |
| 2008/0009794 A1 | 1/2008 | Bagaoisan et al. |
| 2008/0033459 A1 | 2/2008 | Shafi et al. |
| 2008/0045979 A1 | 2/2008 | Ma |
| 2008/0058839 A1 | 3/2008 | Nobles et al. |
| 2008/0065151 A1 | 3/2008 | Ginn |
| 2008/0065152 A1* | 3/2008 | Carley .......................... 606/215 |
| 2008/0086075 A1 | 4/2008 | Isik et al. |
| 2008/0093414 A1 | 4/2008 | Bender et al. |
| 2008/0114378 A1 | 5/2008 | Matsushita |
| 2008/0114395 A1 | 5/2008 | Mathisen et al. |
| 2008/0177288 A1 | 7/2008 | Carlson |
| 2008/0210737 A1 | 9/2008 | Ginn et al. |
| 2008/0221616 A1 | 9/2008 | Ginn et al. |
| 2008/0243148 A1 | 10/2008 | Mikkaichi et al. |
| 2008/0243182 A1 | 10/2008 | Bates et al. |
| 2008/0269801 A1 | 10/2008 | Coleman et al. |
| 2008/0269802 A1 | 10/2008 | Coleman et al. |
| 2008/0272173 A1 | 11/2008 | Coleman et al. |
| 2008/0287967 A1 | 11/2008 | Andreas et al. |
| 2008/0287988 A1* | 11/2008 | Smith et al. ................... 606/216 |
| 2008/0300628 A1 | 12/2008 | Ellingwood |
| 2008/0312686 A1 | 12/2008 | Ellingwood |
| 2008/0312740 A1 | 12/2008 | Wachter et al. |
| 2009/0054912 A1 | 2/2009 | Heanue et al. |
| 2009/0088794 A1 | 4/2009 | LaFontaine |
| 2009/0105728 A1* | 4/2009 | Noda et al. ................... 606/139 |
| 2009/0112306 A1 | 4/2009 | Bonsignore et al. |
| 2009/0137900 A1 | 5/2009 | Bonner et al. |
| 2009/0157101 A1* | 6/2009 | Reyes et al. .................. 606/142 |
| 2009/0157102 A1 | 6/2009 | Reynolds et al. |
| 2009/0171388 A1 | 7/2009 | Dave et al. |
| 2009/0187215 A1 | 7/2009 | Mackiewicz et al. |
| 2009/0216267 A1 | 8/2009 | Willard et al. |
| 2009/0227938 A1 | 9/2009 | Fasching et al. |
| 2009/0230168 A1 | 9/2009 | Coleman et al. |
| 2009/0254119 A1 | 10/2009 | Sibbitt, Jr. et al. |
| 2009/0287244 A1 | 11/2009 | Kokish |
| 2009/0306681 A1* | 12/2009 | Del Nido et al. .............. 606/139 |
| 2009/0312789 A1 | 12/2009 | Kassab et al. |
| 2010/0042144 A1 | 2/2010 | Bennett |
| 2010/0114156 A1 | 5/2010 | Mehl |
| 2010/0130965 A1* | 5/2010 | Sibbitt et al. ....................... 606/2 |
| 2010/0168790 A1 | 7/2010 | Clark |
| 2010/0179567 A1 | 7/2010 | Voss et al. |
| 2010/0179571 A1 | 7/2010 | Voss |
| 2010/0179572 A1 | 7/2010 | Voss et al. |
| 2010/0179589 A1 | 7/2010 | Roorda et al. |
| 2010/0179590 A1 | 7/2010 | Fortson et al. |
| 2010/0185234 A1 | 7/2010 | Fortson et al. |
| 2010/0217132 A1 | 8/2010 | Ellingwood et al. |
| 2010/0234884 A1 | 9/2010 | Lafontaine et al. |
| 2010/0249828 A1 | 9/2010 | Mavani et al. |
| 2011/0054492 A1 | 3/2011 | Clark |
| 2011/0066163 A1* | 3/2011 | Cho et al. ...................... 606/142 |
| 2011/0066164 A1 | 3/2011 | Walberg et al. |
| 2011/0071565 A1 | 3/2011 | Ginn |
| 2011/0106148 A1 | 5/2011 | Ginn et al. |
| 2011/0137340 A1 | 6/2011 | Cummins |
| 2011/0144691 A1 | 6/2011 | Cummins |
| 2011/0166584 A1 | 7/2011 | Palermo et al. |
| 2011/0178548 A1 | 7/2011 | Tenerz |
| 2011/0218568 A1 | 9/2011 | Voss |
| 2011/0238089 A1 | 9/2011 | Reyes et al. |
| 2011/0270282 A1 | 11/2011 | Lemke |
| 2011/0288563 A1 | 11/2011 | Gianotti et al. |
| 2011/0313452 A1 | 12/2011 | Carley et al. |
| 2012/0029555 A1 | 2/2012 | Fortson et al. |
| 2012/0035630 A1 | 2/2012 | Roorda |
| 2012/0143216 A1 | 6/2012 | Voss |
| 2012/0209317 A1 | 8/2012 | Oepen |
| 2012/0245623 A1 | 9/2012 | Kariniemi et al. |
| 2012/0245626 A1 | 9/2012 | Ellingwood et al. |
| 2012/0255655 A1 | 10/2012 | Carley et al. |
| 2012/0296372 A1 | 11/2012 | Ziobro |
| 2012/0296374 A1 | 11/2012 | Ziobro et al. |
| 2013/0006274 A1 | 1/2013 | Walberg et al. |
| 2013/0138144 A1 | 5/2013 | Yibarren |

FOREIGN PATENT DOCUMENTS

| | | |
|---|---|---|
| DE | 197 11 288 | 10/1998 |
| DE | 29723736 U1 | 4/1999 |
| DE | 19859952 | 2/2000 |
| DE | 102006056283 | 6/2008 |
| EP | 0 386 361 | 9/1990 |
| EP | 0 534 696 | 3/1993 |
| EP | 0 621 032 | 10/1994 |
| EP | 0 756 851 | 2/1997 |
| EP | 0 774 237 | 5/1997 |
| EP | 0 858 776 | 8/1998 |
| EP | 0 941 697 | 9/1999 |
| EP | 1 867 287 | 12/2007 |
| FR | 2 443 238 | 7/1980 |
| FR | 2 715 290 | 7/1995 |
| FR | 2 722 975 | 2/1996 |
| FR | 2 768 324 | 3/1999 |
| FR | 2768324 | 3/1999 |
| GB | 1 358 466 | 7/1974 |
| GB | 2 075 144 | 11/1981 |
| GB | 2 397 240 | 7/2004 |
| IE | S2000/0722 | 10/2001 |
| IE | S2000/0724 | 10/2001 |
| IE | S2001/0547 | 7/2002 |
| IE | S2001/0815 | 7/2002 |
| IE | S2001/0748 | 8/2002 |
| IE | S2001/0749 | 8/2002 |
| IE | S2002/0452 | 12/2002 |
| IE | S2002/0664 | 2/2003 |
| IE | S2002/0665 | 2/2003 |
| IE | S2002/0451 | 7/2003 |
| IE | S2002/0552 | 7/2003 |
| IE | S2003/0424 | 12/2003 |
| IE | S2003/0490 | 1/2004 |
| IE | S2004/0368 | 11/2005 |
| IE | S2005/0342 | 11/2005 |
| JP | 58-181006 | 12/1983 |

(56) References Cited

FOREIGN PATENT DOCUMENTS

| | | |
|---|---|---|
| JP | 12 74750 | 11/1989 |
| JP | 11500642 | 8/1997 |
| JP | 2000014634 A | 1/2000 |
| JP | 2000102546 | 4/2000 |
| JP | 2005218868 A | 8/2005 |
| NL | 9302140 | 7/1995 |
| PL | 171425 | 4/1997 |
| RU | 2086192 | 8/1997 |
| SU | 495067 | 12/1975 |
| SU | 912155 | 3/1982 |
| SU | 1243708 | 7/1986 |
| SU | 1324650 | 7/1987 |
| SU | 1405828 | 6/1988 |
| SU | 1456109 | 2/1989 |
| SU | 1560133 | 4/1990 |
| WO | WO 96/24291 | 8/1996 |
| WO | WO 96/40356 | 12/1996 |
| WO | WO 97/07741 | 3/1997 |
| WO | WO 97/20505 | 6/1997 |
| WO | WO 97/27897 | 8/1997 |
| WO | WO 98/06346 | 2/1998 |
| WO | WO 98/06448 | 2/1998 |
| WO | WO 98/16161 | 4/1998 |
| WO | WO 98/17179 | 4/1998 |
| WO | WO 98/18389 | 5/1998 |
| WO | WO 98/24374 | 6/1998 |
| WO | WO 98/25508 | 6/1998 |
| WO | WO 98/58591 | 12/1998 |
| WO | WO 99/21491 | 5/1999 |
| WO | WO 99/40849 | 8/1999 |
| WO | WO 99/60941 | 12/1999 |
| WO | WO 99/62408 | 12/1999 |
| WO | WO 99/62415 | 12/1999 |
| WO | WO 00/06029 | 2/2000 |
| WO | WO 00/07505 | 2/2000 |
| WO | WO 00/07640 | 2/2000 |
| WO | WO 00/27311 | 5/2000 |
| WO | WO 00/27313 | 5/2000 |
| WO | WO 00/56223 | 9/2000 |
| WO | WO 00/56226 | 9/2000 |
| WO | WO 00/56227 | 9/2000 |
| WO | WO 00/56228 | 9/2000 |
| WO | WO 00/71032 | 11/2000 |
| WO | WO 01/21058 | 3/2001 |
| WO | WO 01/35832 | 5/2001 |
| WO | WO 01/47594 | 7/2001 |
| WO | WO 01/49186 | 7/2001 |
| WO | WO 01/91628 | 12/2001 |
| WO | WO 02/19915 | 3/2002 |
| WO | WO 02/19920 | 3/2002 |
| WO | WO 02/19922 | 3/2002 |
| WO | WO 02/19924 | 3/2002 |
| WO | WO 02/28286 | 4/2002 |
| WO | WO 02/38055 | 5/2002 |
| WO | WO 02/45593 | 6/2002 |
| WO | WO 02/45594 | 6/2002 |
| WO | WO 02/062234 | 8/2002 |
| WO | WO 02/098302 | 12/2002 |
| WO | WO 03/013363 | 2/2003 |
| WO | WO 03/013364 | 2/2003 |
| WO | WO 03/047434 | 6/2003 |
| WO | WO 03/071955 | 9/2003 |
| WO | WO 03/071956 | 9/2003 |
| WO | WO 03/071957 | 9/2003 |
| WO | WO 03/094748 | 11/2003 |
| WO | WO 03/101310 | 12/2003 |
| WO | WO 2004/004578 | 1/2004 |
| WO | WO 2004/012602 | 2/2004 |
| WO | WO 2004/060169 | 7/2004 |
| WO | WO 2004/069054 | 8/2004 |
| WO | WO 2005/000126 | 1/2005 |
| WO | WO 2005/006990 | 1/2005 |
| WO | WO 2005/041782 | 5/2005 |
| WO | WO 2005/063129 | 7/2005 |
| WO | WO 2005/082256 | 9/2005 |
| WO | WO 2005/092204 | 10/2005 |
| WO | WO 2005/110240 | 11/2005 |
| WO | WO 2005/112782 | 12/2005 |
| WO | WO 2005/115251 | 12/2005 |
| WO | WO 2005/115521 | 12/2005 |
| WO | WO 2006/000514 | 1/2006 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/083889 | 8/2006 |
| WO | WO 2006/115901 | 11/2006 |
| WO | WO 2006/115904 | 11/2006 |
| WO | WO 2006/118877 | 11/2006 |
| WO | WO 2007/005585 | 1/2007 |
| WO | WO 2007/025014 | 3/2007 |
| WO | WO 2007/025017 | 3/2007 |
| WO | WO 2007/025018 | 3/2007 |
| WO | WO 2007/025019 | 3/2007 |
| WO | WO 2007/081836 | 7/2007 |
| WO | WO 2007/088069 | 8/2007 |
| WO | WO 2008/031102 | 3/2008 |
| WO | WO 2008/036384 | 3/2008 |
| WO | WO 2008/074027 | 6/2008 |
| WO | WO 2008/150915 | 12/2008 |
| WO | WO 2009/079091 | 6/2009 |
| WO | WO 2010/031050 | 3/2010 |
| WO | WO 2010/062693 | 6/2010 |
| WO | WO 2010/081101 | 7/2010 |
| WO | WO 2010/081102 | 7/2010 |
| WO | WO 2010/081103 | 7/2010 |
| WO | WO 2010/081106 | 7/2010 |
| ZA | 200100527 | 1/2001 |
| ZA | 200100528 | 1/2001 |

OTHER PUBLICATIONS

U.S. Appl. No. 09/866,551, filed May 25, 2001, Ginn.
U.S. Appl. No. 12/113,092, filed Apr. 30, 2008, Ginn et al.
U.S. Appl. No. 13/017,636, filed Jan. 31, 2011, Carley et al.
U.S. Appl. No. 13/791,829, filed Mar. 8, 2013, Roorda et al.
U.S. Appl. No. 13/791,846, filed Mar. 8, 2013, Palermo.
U.S. Appl. No. 13/898,202, filed May 20, 2013, Walberg et al.
U.S. Appl. No. 60/693,531, filed Jun. 24, 2005, Carly.
U.S. Appl. No. 60/696,069, filed Jul. 1, 2005, Pantages et al.
U.S. Appl. No. 60/793,444, filed Apr. 20, 2006, Jones et al.
U.S. Appl. No. 60/946,026, filed Jun. 25, 2007, Ellingwood.
U.S. Appl. No. 60/946,030, filed Jun. 25, 2007, Voss et al.
U.S. Appl. No. 60/946,042, filed Jun. 25, 2007, Ellingwood et al.
U.S. Appl. No. 61/015,144, filed Dec. 19, 2007, Mackiewicz et al.
U.S. Appl. No. 61/109,822, filed Oct. 30, 2008, Mehl et al.
U.S. Appl. No. 61/139,995, filed Dec. 22, 2008, Clark.
U.S. Appl. No. 61/141,597, filed Dec. 30, 2008, Clark.
U.S. Appl. No. 61/143,748, filed Jan. 9, 2009, Mehl et al.
U.S. Appl. No. 61/143,751, filed Jan. 9, 2009, Voss et al.
U.S. Appl. No. 61/145,468, filed Jan. 16, 2009, Fortson, et al.
"Hand tool for forming telephone connections—comprises pliers with reciprocably driven ram crimping clip around conductors against anvil", Derwent-ACC-No. 1978-B8090A. (Jan. 10, 1978).
Database WPI; Section PQ, Week 200120; Derwent Publications Ltd., London GB; AN 2001-203165; XP002199926 & ZA 200 100 528 A (Anthony T), Feb. 28, 2001 abstract.
Deepak Mital et al, Renal Transplantation Without Sutures Using the Vascular Clipping System for Renal Artery and Vein Anastomosis—A New Technique, Transplantation Issue, Oct. 1996, pp. 1171-1173, vol. 62—No. 8, Section of Transplantation Surgery, Department of General Surgery, Rush-Presbyterian/St. Luke's Medical Center, Chigago, IL.
DL Wessel et al, Outpatient closure of the patent ductus arteriosus, Circulation, May 1988, pp. 1068-1071, vol. 77—No. 5, Department of Anesthesia, Children's Hospital, Boston, MA.
E Pikoulis et al, Arterial reconstruction with vascular clips is safe and quicker than sutured repair, Cardiovascular Surgery, Dec. 1998, pp. 573-578(6), vol. 6—No. 6, Department of Surgery, Uniformed Services University of the Health Sciences, Bethesda, MD.

(56) References Cited

OTHER PUBLICATIONS

G Gershony et al, Novel vascular sealing device for closure of percutaneous vascular access sites, Cathet. Cardiovasc. Diagn., Jan. 1998, pp. 82-88, vol. 45.

H De Swart et al, A new hemostatic puncture closure device for the immediate sealing of arterial puncture sites, American journal of cardiology, Aug. 1993, pp. 445-449, vol. 72—No. 5, Department of Cardiology, Academic Hospital Maastricht, The Netherlands.

Harrith M. Hasson M.D. , Laparoscopic Cannula Cone with Means for Cannula Stabilization and Wound Closure, The Journal of the American Association of Gynecologic Laparoscopists, May 1998, pp. 183-185, vol. 5—No. 2, Division of Obstetrics and Gynecology, University of Chicago, Chigago, IL.

J. Findlay et al, Carotid Arteriotomy Closure Using a Vascular Clip System, Neurosurgery, Mar. 1998, pp. 550-554, vol. 42—No. 3, Division of Neurosurgery, University of Alberta, Edmonton, Canada.

Jeremy L Gilbert Phd, Wound Closure Biomaterials and Devices, Shock., Mar. 1999, p. 226, vol. 11—No. 3, Institution Northwestern University (editorial review).

Jochen T. Cremer, MD, et al, Different approaches for minimally invasive closure of atrial septal defects, Ann. Thorac. Surg., Nov. 1998, pp. 1648-1652, vol. 67, a Division of Thoracic and Cardiovascular Surgery, Surgical Center, Hannover Medical School. Hannover, Germany.

K Narayanan et al, Simultaneous primary closure of four fasciotomy wounds in a single setting using the Sure-Closure device, Injury, Jul. 1996, pp. 449-451, vol. 27—No. 6, Department of Surgery, Mercy Hospital of Pittsburgh, PA.

Marshall A.C., Lock J.E., Structural and Compliant Anatomy of the Patent Foramen Ovale in Patients Undergoing Transcatheter Closure, Am Heart J Aug. 2000; 140(2); pp. 303-307.

MD Gonze et al, Complications associated with percutaneous closure devices, Conference: Annual Meeting of the Society for Clinical Vascular Surgery, The American journal of surgery, Mar. 1999, pp. 209-211, vol. 178, No. 3, Department of Surgery, Section of Vascular Surgery, Ochsner Medical Institutions, New Orleans, LA.

MD Hellinger et al, Effective peritoneal and fascial closure of abdominal trocar sites utilizing the Endo-Judge, J Laparoendosc Surg., Oct. 1996, pp. 329-332, vol. 6—No. 5, Orlando Regional Medical Center, FL.

Michael Gianturco, A Play on Catheterization, Forbes, Dec. 1996, p. 146, vol. 158—No. 15.

Inlet Medical Inc. Brochure, pp. 1-2, referencing OM Elashry et al, Comparative clinical study of port-closure techniques following laparoscopic surgery, Department of Surgery, Mallickrodt Institute of Radiography, J Am Coll Surg., Oct. 1996, pp. 335-344, vol. 183—No. 4.

P M N Werker, et al, Review of facilitated approaches to vascular anastomosis surgery, Conference: Utrecht MICBAG Workshop 2, The Annals of thoracic surgery, Apr. 1996, pp. S122-S127, vol. 63—No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.

Peter Rhee MD et al, Use of Titanium Vascular Staples in Trauma, Journal of Trauma-Injury Infection & Critical Care, Dec. 1998, pp. 1097-1099, vol. 45—No. 6, Institution from the Department of Surgery, Washington Hospital Center, Washington DC, and Uniformed Services University of the Health Sciences, Bethesda, Maryland.

ProstarXL—Percutaneous Vascular Surgical Device, www.Archive.org, Jun. 1998, Original Publisher: http://prostar.com, may also be found at http://web.archive.org/web/19980630040429/www.perclose.com/html/prstrxl.html.

SA Beyer-Enke et al, Immediate sealing of arterial puncture site following femoropopliteal angioplasty: A prospective randomized trial, Cardiovascular and Interventional Radiology 1996, Nov.-Dec. 996, pp. 406-410, vol. 19—No. 6, Gen Hosp North, Dept Dianost & Intervent Radiol, Nurnberg, Germany (Reprint).

Scott Hensley, Closing Wounds. New Devices seal arterial punctures in double time, Modern Healthcare (United States), Mar. 23, 2008, p. 48.

Sigmund Silber et al, A novel vascular device for closure of percutaneous arterial access sites, The American Journal of Cardiology, Apr. 1999, pp. 1248-1252, vol. 83—No. 8.

Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25.—No. 2, Supplement 1.

Stretch Comb by Scunci, retrieved via internet at www.scunci.com/productdetail by examiner on Oct. 9, 2007, publication date unavailable.

Swee Lian Tan, MD, PhD, FACS, Explanation of Infected Hemostatic Puncture Closure Devices—A Case Report, Vascular and Endovascular Surgery, 1999, pp. 507-510, vol. 33—No. 5, Parkland Medical Center, Derry, New Hampshire.

SY Nakada et al, Comparison of newer laparoscopic port closure techniques in the porcine model, J Endourol, Oct. 1995, pp. 397-401, vol. 9—No. 5, Department of Surgery/Urology, University of Wisconsin Medical School, Madison.

Taber's Cyclopedic Medical Dictionary, 18th Ed. 1997, pp. 747 and 1420.

Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42—No. 3, Institution Department of Plastic and Reconstructive Surgery, Albert Einstein College of Medicine and Montefiore Medical Center, Bronx, NY.

Tomoaki Hinohara, Percutaneous vascular surgery (Prostar® Plus and Techstar® for femoral artery site closure), Interventional Cardiology Newsletter, May-Jul. 1997, pp. 19-22, pp. 24-28, vol. 5—No. 3-4.

UT Aker et al, Immediate arterial hemostasis after cardiac catheterization: initial experience with a new puncture closure device, Cathet Cardiovasc Diagn, Mar. 1994, pp. 228-232, vol. 33—No. 3, Missouri Baptist Medical Center, St. Louis.

Wei Qu et al, An absorbable pinned-ring device for microvascular anastomosis of vein grafts: Experimental studies, Microsurgery 1999, Mar. 1999, pp. 128-134, vol. 19—No. 3, Department of Orthopaedic Surgery, Hiroshima University School of Medicine, Hiroshima, Japan.

William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25—No. 7.

U.S. Appl. No. 09/478,179, Nov. 6, 2000, Notice of Allowance.
U.S. Appl. No. 09/546,998, May 6, 2002, Notice of Allowance.
U.S. Appl. No. 09/610,238, Mar. 26, 2001, Notice of Allowance.
U.S. Appl. No. 09/610,238, Sep. 5, 2001, Office Action.
U.S. Appl. No. 09/610,238, Feb. 11, 2002, Notice of Allowance.
U.S. Appl. No. 09/680,837, Jul. 9, 2002, Office Action.
U.S. Appl. No. 09/680,837, Nov. 6, 2002, Office Action.
U.S. Appl. No. 09/680,837, Mar. 25, 2003, Office Action.
U.S. Appl. No. 09/680,837, Jun. 16, 2003, Notice of Allowance.
U.S. Appl. No. 09/732,178, Aug. 1, 2002, Office Action.
U.S. Appl. No. 09/732,178, Dec. 24, 2002, Office Action.
U.S. Appl. No. 09/732,178, Jun. 10, 2003, Office Action.
U.S. Appl. No. 09/732,178, Jul. 3, 2003, Office Action.
U.S. Appl. No. 09/732,178, Nov. 17, 2003, Notice of Allowance.
U.S. Appl. No. 09/732,835, Sep. 11, 2003, Office Action.
U.S. Appl. No. 09/732,835, Feb. 9, 2004, Office Action.
U.S. Appl. No. 09/732,835, Mar. 17, 2004, Notice of Allowance.
U.S. Appl. No. 09/764,813, Mar. 26, 2001, Office Action.
U.S. Appl. No. 09/764,813, Jun. 4, 2001, Notice of Allowance.
U.S. Appl. No. 09/933,299, Feb. 26, 2003, Office Action.
U.S. Appl. No. 09/933,299, Jun. 16, 2003, Notice of Allowance.
U.S. Appl. No. 09/948,813, Jan. 31, 2003, Notice of Allowance.
U.S. Appl. No. 09/949,398, Mar. 4, 2003, Office Action.
U.S. Appl. No. 09/949,398, Jul. 28, 2003, Notice of Allowance.
U.S. Appl. No. 09/949,438, Dec. 17, 2002, Office Action.
U.S. Appl. No. 09/949,438, Apr. 21, 2003, Notice of Allowance.

(56) References Cited

OTHER PUBLICATIONS

U.S. Appl. No. 10/006,400, Aug. 27, 2004, Office Action.
U.S. Appl. No. 10/006,400, Feb. 23, 2005, Office Action.
U.S. Appl. No. 10/006,400, Apr. 11, 2005, Office Action.
U.S. Appl. No. 10/006,400, Jul. 27, 2005, Office Action.
U.S. Appl. No. 10/006,400, Mar. 6, 2006, Office Action.
U.S. Appl. No. 10/006,400, May 24, 2006, Office Action.
U.S. Appl. No. 10/006,400, Oct. 26, 2006, Office Action.
U.S. Appl. No. 10/006,400, Apr. 19, 2007, Office Action.
U.S. Appl. No. 10/006,400, Apr. 2, 2008, Office Action.
U.S. Appl. No. 10/006,400, Jan. 2, 2009, Office Action.
U.S. Appl. No. 10/006,400, Jul. 9, 2009, Notice of Allowance.
U.S. Appl. No. 10/006,400, Jan. 13, 2010, Notice of Allowance.
U.S. Appl. No. 10/006,400, Apr. 27, 2010, Notice of Allowance.
U.S. Appl. No. 10/006,400, Aug. 2, 2010, Notice of Allowance.
U.S. Appl. No. 10/081,717, Sep. 29, 2003, Notice of Allowance.
U.S. Appl. No. 10/081,723, Sep. 29, 2004, Office Action.
U.S. Appl. No. 10/081,723, May 13, 2005, Notice of Allowance.
U.S. Appl. No. 10/081,725, Feb. 9, 2004, Notice of Allowance.
U.S. Appl. No. 10/081,725, Apr. 13, 2004, Office Action.
U.S. Appl. No. 10/081,726, Apr. 11, 2003, Notice of Allowance.
U.S. Appl. No. 10/081,726, Jun. 9, 2003, Notice of Allowance.
U.S. Appl. No. 10/147,774, Nov. 4, 2004, Office Action.
U.S. Appl. No. 10/147,774, May 4, 2005, Office Action.
U.S. Appl. No. 10/147,774, Oct. 18, 2005, Office Action.
U.S. Appl. No. 10/147,774, Apr. 18, 2007, Notice of Allowance.
U.S. Appl. No. 10/147,774, Sep. 27, 2007, Notice of Allowance.
U.S. Appl. No. 10/147,774, Feb. 4, 2008, Notice of Allowance.
U.S. Appl. No. 10/147,774, Jun. 30, 2008, Office Action.
U.S. Appl. No. 10/147,774, Mar. 18, 2009, Office Action.
U.S. Appl. No. 10/147,774, Oct. 26, 2009, Office Action.
U.S. Appl. No. 10/147,774, Jun. 8, 2010, Office Action.
U.S. Appl. No. 10/147,774, Dec. 2, 2010, Notice of Allowance.
U.S. Appl. No. 10/240,183, Jul. 27, 2004, Office Action.
U.S. Appl. No. 10/240,183, Dec. 17, 2004, Office Action.
U.S. Appl. No. 10/240,183, Mar. 9, 2005, Notice of Allowance.
U.S. Appl. No. 10/240,183, Aug. 11, 2006, Office Action.
U.S. Appl. No. 10/264,306, Feb. 9, 2005, Office Action.
U.S. Appl. No. 10/264,306, Oct. 4, 2005, Office Action.
U.S. Appl. No. 10/264,306, May 10, 2006, Notice of Allowance.
U.S. Appl. No. 10/264,306, Jul. 2, 2007, Notice of Allowance.
U.S. Appl. No. 10/264,306, Feb. 4, 2008, Notice of Allowance.
U.S. Appl. No. 10/264,306, Jun. 27, 2008, Office Action.
U.S. Appl. No. 10/264,306, Feb. 26, 2009, Office Action.
U.S. Appl. No. 10/264,306, Aug. 13, 2009, Office Action.
U.S. Appl. No. 10/264,306, Jan. 27, 2010, Office Action.
U.S. Appl. No. 10/264,306, Jun. 15, 2010, Office Action.
U.S. Appl. No. 10/264,306, Oct. 29, 2010, Notice of Allowance.
U.S. Appl. No. 10/335,075, Aug. 10, 2005, Office Action.
U.S. Appl. No. 10/335,075, Dec. 19, 2005, Office Action.
U.S. Appl. No. 10/335,075, Apr. 21, 2006, Office Action.
U.S. Appl. No. 10/335,075, Dec. 27, 2006, Notice of Allowance.
U.S. Appl. No. 10/356,214, Nov. 30, 2005, Office Action.
U.S. Appl. No. 10/356,214, Aug. 23, 2006, Office Action.
U.S. Appl. No. 10/356,214, Feb. 13, 2007, Office Action.
U.S. Appl. No. 10/356,214, Sep. 12, 2007, Office Action.
U.S. Appl. No. 10/356,214, Mar. 6, 2008, Office Action.
U.S. Appl. No. 10/356,214, Nov. 4, 2008, Office Action.
U.S. Appl. No. 10/356,214, Apr. 29, 2009, Office Action.
U.S. Appl. No. 10/356,214, Jan. 13, 2010, Notice of Allowance.
U.S. Appl. No. 10/356,214, May 13, 2010, Notice of Allowance.
U.S. Appl. No. 10/356,214, Sep. 3, 2010, Notice of Allowance.
U.S. Appl. No. 10/435,104, Jun. 10, 2004, Office Action.
U.S. Appl. No. 10/435,104, Sep. 21, 2004, Notice of Allowance.
U.S. Appl. No. 10/435,104, Jan. 3, 2006, Office Action.
U.S. Appl. No. 10/435,104, May 16, 2006, Office Action.
U.S. Appl. No. 10/435,104, Dec. 28, 2006, Notice of Allowance.
U.S. Appl. No. 10/435,104, Jul. 10, 2007, Notice of Allowance.
U.S. Appl. No. 10/435,104, Aug. 2, 2007, Notice of Allowance.
U.S. Appl. No. 10/435,104, Oct. 26, 2007, Notice of Allowance.
U.S. Appl. No. 10/435,104, Nov. 14, 2007, Notice of Allowance.
U.S. Appl. No. 10/435,104, Apr. 4, 2008, Notice of Allowance.
U.S. Appl. No. 10/435,104, Sep. 26, 2008, Notice of Allowance.
U.S. Appl. No. 10/435,104, Dec. 22, 2008, Notice of Allowance.
U.S. Appl. No. 10/435,104, Jul. 23, 2009, Notice of Allowance.
U.S. Appl. No. 10/435,104, Jan. 20, 2010, Notice of Allowance.
U.S. Appl. No. 10/435,104, Jun. 2, 2010, Office Action.
U.S. Appl. No. 10/435,104, Oct. 5, 2010, Notice of Allowance.
U.S. Appl. No. 10/455,768, Nov. 16, 2004, Office Action.
U.S. Appl. No. 10/455,768, Apr. 6, 2005, Notice of Allowance.
U.S. Appl. No. 10/486,067, Jan. 10, 2006, Office Action.
U.S. Appl. No. 10/486,067, Sep. 20, 2006, Notice of Allowance.
U.S. Appl. No. 10/486,070, Apr. 20, 2005, Office Action.
U.S. Appl. No. 10/486,070, Aug. 10, 2005, Office Action.
U.S. Appl. No. 10/486,070, Oct. 18, 2005, Notice of Allowance.
U.S. Appl. No. 10/517,004, Aug. 13, 2007, Office Action.
U.S. Appl. No. 10/517,004, Jan. 30, 2008, Office Action.
U.S. Appl. No. 10/517,004, Aug. 13, 2008, Notice of Allowance.
U.S. Appl. No. 10/517,004, Feb. 10, 2009, Notice of Allowance.
U.S. Appl. No. 10/517,004, Mar. 24, 2009, Notice of Allowance.
U.S. Appl. No. 10/517,004, Jun. 26, 2009, Notice of Allowance.
U.S. Appl. No. 10/517,004, Jan. 11, 2010, Notice of Allowance.
U.S. Appl. No. 10/517,004, Apr. 23, 2010, Notice of Allowance.
U.S. Appl. No. 10/517,004, Aug. 3, 2010, Notice of Allowance.
U.S. Appl. No. 10/519,778, Feb. 23, 2006, Office Action.
U.S. Appl. No. 10/519,778, May 31, 2006, Notice of Allowance.
U.S. Appl. No. 10/541,083, Oct. 16, 2007, Office Action.
U.S. Appl. No. 10/541,083, Oct. 31, 2007, Office Action.
U.S. Appl. No. 10/541,083, May 5, 2008, Office Action.
U.S. Appl. No. 10/541,083, Sep. 19, 2008, Notice of Allowance.
U.S. Appl. No. 10/541,083, Dec. 29, 2008, Notice of Allowance.
U.S. Appl. No. 10/541,083, Apr. 16, 2009, Notice of Allowance.
U.S. Appl. No. 10/541,083, Sep. 30, 2009, Notice of Allowance.
U.S. Appl. No. 10/541,083, Feb. 5, 2010, Notice of Allowance.
U.S. Appl. No. 10/541,083, May 10, 2010, Notice of Allowance.
U.S. Appl. No. 10/541,083, Aug. 17, 2010, Notice of Allowance.
U.S. Appl. No. 10/616,832, Jun. 30, 2006, Office Action.
U.S. Appl. No. 10/616,832, Oct. 20, 2006, Office Action.
U.S. Appl. No. 10/616,832, May 29, 2007, Office Action.
U.S. Appl. No. 10/616,832, Jan. 22, 2008, Office Action.
U.S. Appl. No. 10/616,832, Sep. 17, 2008, Office Action.
U.S. Appl. No. 10/616,832, Jul. 21, 2009, Office Action.
U.S. Appl. No. 10/616,832, Jan. 11, 2010, Notice of Allowance.
U.S. Appl. No. 10/616,832, May 12, 2010, Notice of Allowance.
U.S. Appl. No. 10/616,832, Sep. 20, 2010, Notice of Allowance.
U.S. Appl. No. 10/617,090, Mar. 22, 2005, Office Action.
U.S. Appl. No. 10/617,090, Jul. 6, 2005, Notice of Allowance.
U.S. Appl. No. 10/617,090, Oct. 5, 2005, Notice of Allowance.
U.S. Appl. No. 10/638,115, Sep. 22, 2006, Restriction Requirement.
U.S. Appl. No. 10/638,115, Jan. 31, 2007, Office Action.
U.S. Appl. No. 10/638,115, Sep. 18, 2007, Office Action.
U.S. Appl. No. 10/638,115, Feb. 7, 2008, Office Action.
U.S. Appl. No. 10/638,115, Oct. 29, 2008, Office Action.
U.S. Appl. No. 10/638,115, May 7, 2009, Notice of Allowance.
U.S. Appl. No. 10/638,115, Dec. 1, 2009, Notice of Allowance.
U.S. Appl. No. 10/638,115, Apr. 2, 2010, Notice of Allowance.
U.S. Appl. No. 10/638,115, Aug. 13, 2010, Notice of Allowance.
U.S. Appl. No. 10/667,144, Sep. 19, 2006, Office Action.
U.S. Appl. No. 10/667,144, May 2, 2007, Office Action.
U.S. Appl. No. 10/667,144, Nov. 19, 2007, Office Action.
U.S. Appl. No. 10/667,144, Dec. 5, 2007, Office Action.
U.S. Appl. No. 10/667,144, May 12, 2008, Office Action.
U.S. Appl. No. 10/667,144, Mar. 24, 2009, Office Action.
U.S. Appl. No. 10/667,144, Nov. 23, 2009, Office Action.
U.S. Appl. No. 10/667,144, Jun. 22, 2010, Office Action.
U.S. Appl. No. 10/667,144, Jun. 6, 2011, Office Action.
U.S. Appl. No. 10/667,144, Oct. 28, 2011, Notice of Allowance.
U.S. Appl. No. 10/669,313, Oct. 31, 2005, Office Action.
U.S. Appl. No. 10/669,313, Jan. 11, 2006, Notice of Allowance.
U.S. Appl. No. 10/669,313, Jun. 28, 2006, Notice of Allowance.
U.S. Appl. No. 10/682,459, Sep. 15, 2006, Office Action.
U.S. Appl. No. 10/682,459, Apr. 18, 2007, Office Action.
U.S. Appl. No. 10/682,459, Apr. 2, 2008, Office Action.

(56) References Cited

OTHER PUBLICATIONS

U.S. Appl. No. 10/682,459, Dec. 4, 2008, Office Action.
U.S. Appl. No. 10/682,459, Jun. 10, 2009, Office Action.
U.S. Appl. No. 10/682,459, Dec. 23, 2009, Office Action.
U.S. Appl. No. 10/682,459, Apr. 28, 2010, Office Action.
U.S. Appl. No. 10/682,459, Oct. 12, 2010, Office Action.
U.S. Appl. No. 10/682,459, Apr. 1, 2011, Notice of Allowance.
U.S. Appl. No. 10/786,444, Oct. 30, 2006, Office Action.
U.S. Appl. No. 10/786,444, Apr. 17, 2007, Office Action.
U.S. Appl. No. 10/786,444, Aug. 31, 2007, Office Action.
U.S. Appl. No. 10/786,444, Apr. 24, 2008, Office Action.
U.S. Appl. No. 10/786,444, Oct. 17, 2008, Office Action.
U.S. Appl. No. 10/786,444, Jun. 18, 2009, Office Action.
U.S. Appl. No. 10/786,444, Jan. 14, 2010, Office Action.
U.S. Appl. No. 10/786,444, Jul. 11, 2013, Notice of Allowance.
U.S. Appl. No. 10/787,073, Nov. 30, 2006, Office Action.
U.S. Appl. No. 10/787,073, Sep. 5, 2007, Office Action.
U.S. Appl. No. 10/787,073, Feb. 22, 2008, Office Action.
U.S. Appl. No. 10/787,073, Nov. 12, 2008, Office Action.
U.S. Appl. No. 10/787,073, Aug. 13, 2009, Office Action.
U.S. Appl. No. 10/787,073, Feb. 17, 2010, Notice of Allowance.
U.S. Appl. No. 10/787,073, Aug. 25, 2010, Notice of Allowance.
U.S. Appl. No. 10/908,721, Oct. 19, 2006, Office Action.
U.S. Appl. No. 10/908,721, Aug. 10, 2007, Office Action.
U.S. Appl. No. 10/908,721, Jan. 25, 2008, Office Action.
U.S. Appl. No. 10/908,721, Nov. 25, 2008, Office Action.
U.S. Appl. No. 10/908,721, Jun. 23, 2009, Office Action.
U.S. Appl. No. 10/908,721, Feb. 2, 2010, Office Action.
U.S. Appl. No. 11/048,503, Mar. 13, 2009, Office Action.
U.S. Appl. No. 11/048,503, Jun. 26, 2009, Office Action.
U.S. Appl. No. 11/048,503, Jan. 11, 2010, Notice of Allowance.
U.S. Appl. No. 11/048,503, Apr. 26, 2010, Notice of Allowance.
U.S. Appl. No. 11/048,503, Jul. 30, 2010, Notice of Allowance.
U.S. Appl. No. 11/113,549, Feb. 6, 2007, Office Action.
U.S. Appl. No. 11/113,549, May 30, 2007, Office Action.
U.S. Appl. No. 11/113,549, Nov. 9, 2007, Office Action.
U.S. Appl. No. 11/113,549, Apr. 16, 2008, Office Action.
U.S. Appl. No. 11/113,549, Jul. 21, 2009, Office Action.
U.S. Appl. No. 11/113,549, Jul. 6, 2010, Office Action.
U.S. Appl. No. 11/113,549, Jan. 4, 2011, Office Action.
U.S. Appl. No. 11/152,562, May 13, 2008, Office Action.
U.S. Appl. No. 11/152,562, Feb. 13, 2009, Office Action.
U.S. Appl. No. 11/152,562, Jul. 6, 2009, Office Action.
U.S. Appl. No. 11/152,562, Mar. 31, 2010, Office Action.
U.S. Appl. No. 11/152,562, Sep. 16, 2010, Notice of Allowance.
U.S. Appl. No. 11/198,811, Aug. 26, 2008, Office Action.
U.S. Appl. No. 11/198,811, Apr. 6, 2009, Office Action.
U.S. Appl. No. 11/198,811, Sep. 22, 2009, Office Action.
U.S. Appl. No. 11/198,811, Jun. 29, 2010, Notice of Allowance.
U.S. Appl. No. 11/344,793, Jan. 22, 2009, Office Action.
U.S. Appl. No. 11/344,868, Mar. 25, 2009, Office Action.
U.S. Appl. No. 11/344,891, Apr. 29, 2008, Office Action.
U.S. Appl. No. 11/344,891, Dec. 8, 2008, Office Action.
U.S. Appl. No. 11/344,891, Feb. 26, 2009, Office Action.
U.S. Appl. No. 11/344,891, Oct. 7, 2009, Office Action.
U.S. Appl. No. 11/344,891, May 7, 2010, Office Action.
U.S. Appl. No. 11/344,891, Jan. 22, 2013, Notice of Allowance.
U.S. Appl. No. 11/390,586, Jun. 24, 2009, Office Action.
U.S. Appl. No. 11/390,586, Jul. 6, 2010, Office Action.
U.S. Appl. No. 11/390,586, May 3, 2012, Notice of Allowance.
U.S. Appl. No. 11/396,141, May 22, 2009, Restriction Requirement.
U.S. Appl. No. 11/396,141, Aug. 26, 2009, Office Action.
U.S. Appl. No. 11/396,141, May 4, 2010, Office Action.
U.S. Appl. No. 11/396,141, Apr. 30, 2013, Office Action.
U.S. Appl. No. 11/396,731, Feb. 13, 2009, Office Action.
U.S. Appl. No. 11/396,731, May 22, 2009, Office Action.
U.S. Appl. No. 11/396,731, Jun. 29, 2010, Office Action.
U.S. Appl. No. 11/396,731, Mar. 22, 2011, Office Action.
U.S. Appl. No. 11/396,731, Sep. 1, 2011, Office Action.
U.S. Appl. No. 11/406,203, May 14, 2007, Office Action.
U.S. Appl. No. 11/406,203, Jan. 29, 2008, Notice of Allowance.
U.S. Appl. No. 11/406,203, May 23, 2008, Notice of Allowance.
U.S. Appl. No. 11/406,203, Sep. 22, 2008, Notice of Allowance.
U.S. Appl. No. 11/406,203, Mar. 3, 2009, Office Action.
U.S. Appl. No. 11/406,203, Sep. 16, 2009, Office Action.
U.S. Appl. No. 11/406,203, Jun. 18, 2010, Notice of Allowance.
U.S. Appl. No. 11/411,925, Jun. 6, 2007, Office Action.
U.S. Appl. No. 11/411,925, Feb. 5, 2008, Office Action.
U.S. Appl. No. 11/411,925, Jan. 12, 2009, Office Action.
U.S. Appl. No. 11/411,925, Sep. 10, 2009, Office Action.
U.S. Appl. No. 11/427,297, Jan. 30, 2009, Office Action.
U.S. Appl. No. 11/427,297, Sep. 15, 2009, Office Action.
U.S. Appl. No. 11/427,297, Sep. 15, 2010, Office Action.
U.S. Appl. No. 11/427,297, Mar. 21, 2011, Office Action.
U.S. Appl. No. 11/427,297, Jun. 26, 2012, Notice of Allowance.
U.S. Appl. No. 11/427,309, May 28, 2008, Restriction Requirement.
U.S. Appl. No. 11/427,309, Jan. 2, 2009, Office Action.
U.S. Appl. No. 11/427,309, Apr. 20, 2009, Office Action.
U.S. Appl. No. 11/427,309, Nov. 6, 2009, Office Action.
U.S. Appl. No. 11/427,309, Apr. 26, 2010, Office Action.
U.S. Appl. No. 11/427,309, Nov. 15, 2010, Office Action.
U.S. Appl. No. 11/427,309, Jun. 7, 2013, Notice of Allowance.
U.S. Appl. No. 11/455,993, Feb. 17, 2009, Office Action.
U.S. Appl. No. 11/455,993, Dec. 16, 2009, Office Action.
U.S. Appl. No. 11/532,325, Feb. 23, 2009, Office Action.
U.S. Appl. No. 11/532,325, Jun. 17, 2009, Office Action.
U.S. Appl. No. 11/532,325, Jan. 5, 2010, Office Action.
U.S. Appl. No. 11/532,325, Jul. 17, 2013, Office Action.
U.S. Appl. No. 11/532,576, Mar. 1, 2010, Restriction Requirement.
U.S. Appl. No. 11/532,576, Apr. 23, 2010, Office Action.
U.S. Appl. No. 11/532,576, Oct. 13, 2010, Notice of Allowance.
U.S. Appl. No. 11/674,930, Jan. 8, 2009, Office Action.
U.S. Appl. No. 11/674,930, Jun. 4, 2009, Office Action.
U.S. Appl. No. 11/674,930, Jan. 8, 2010, Office Action.
U.S. Appl. No. 11/675,462, Dec. 10, 2009, Office Action.
U.S. Appl. No. 11/675,462, Aug. 31, 2010, Office Action.
U.S. Appl. No. 11/675,462, Aug. 3, 2011, Office Action.
U.S. Appl. No. 11/675,462, Dec. 22, 2011, Notice of Allowance.
U.S. Appl. No. 11/744,089, Nov. 26, 2008, Office Action.
U.S. Appl. No. 11/744,089, Aug. 14, 2009, Office Action.
U.S. Appl. No. 11/744,089, Aug. 8, 2012, Office Action.
U.S. Appl. No. 11/744,089, Apr. 15, 2013, Office Action.
U.S. Appl. No. 11/757,108, Nov. 25, 2009, Restriction Requirement.
U.S. Appl. No. 11/767,818, Dec. 24, 2009, Restriction Requirement.
U.S. Appl. No. 11/767,818, Mar. 22, 2010, Office Action.
U.S. Appl. No. 11/767,818, Sep. 30, 2010, Office Action.
U.S. Appl. No. 11/767,818, Feb. 16, 2011, Office Action.
U.S. Appl. No. 11/767,818, Feb. 3, 2012, Notice of Allowance.
U.S. Appl. No. 11/852,190, Jun. 24, 2010, Restriction Requirement.
U.S. Appl. No. 11/852,190, Nov. 1, 2010, Office Action.
U.S. Appl. No. 11/852,190, Mar. 2, 2011, Office Action.
U.S. Appl. No. 11/852,190, Apr. 24, 2013, Office Action.
U.S. Appl. No. 11/958,281, Sep. 2, 2010, Restriction Requirement.
U.S. Appl. No. 11/958,281, Oct. 8, 2010, Office Action.
U.S. Appl. No. 11/958,281, Mar. 10, 2011, Office Action.
U.S. Appl. No. 11/958,295, Aug. 27, 2009, Office Action.
U.S. Appl. No. 11/958,295, May 25, 2010, Office Action.
U.S. Appl. No. 11/959,334, Aug. 19, 2009, Office Action.
U.S. Appl. No. 11/959,334, Jan. 12, 2010, Notice of Allowance.
U.S. Appl. No. 11/959,334, Apr. 14, 2010, Notice of Allowance.
U.S. Appl. No. 11/959,334, Jul. 23, 2010, Notice of Allowance.
U.S. Appl. No. 12/106,928, Jan. 23, 2009, Office Action.
U.S. Appl. No. 12/106,928, Oct. 5, 2009, Office Action.
U.S. Appl. No. 12/106,928, May 10, 2010, Office Action.
U.S. Appl. No. 12/106,928, Oct. 25, 2010, Office Action.
U.S. Appl. No. 12/106,928, Jun. 28, 2013, Office Action.
U.S. Appl. No. 12/106,937, Mar. 30, 2009, Office Action.
U.S. Appl. No. 12/106,937, Nov. 18, 2009, Office Action.
U.S. Appl. No. 12/106,937, Jun. 28, 2013, Office Action.
U.S. Appl. No. 12/113,851, Apr. 27, 2010, Restriction Requirement.
U.S. Appl. No. 12/113,851, Jun. 24, 2010, Office Action.
U.S. Appl. No. 12/113,851, Dec. 16, 2010, Office Action.
U.S. Appl. No. 12/113,851, Apr. 27, 2011, Office Action.

(56) References Cited

OTHER PUBLICATIONS

U.S. Appl. No. 12/113,851, Mar. 29, 2012, Office Action.
U.S. Appl. No. 12/114,031, Oct. 5, 2010, Restriction Requirement.
U.S. Appl. No. 12/114,031, Nov. 22, 2010, Office Action.
U.S. Appl. No. 12/114,031, May 11, 2011, Office Action.
U.S. Appl. No. 12/114,031, Aug. 2, 2011, Office Action.
U.S. Appl. No. 12/114,031, Mar. 6, 2012, Office Action.
U.S. Appl. No. 12/114,091, Oct. 27, 2010, Restriction Requirement.
U.S. Appl. No. 12/114,091, Dec. 17, 2010, Office Action.
U.S. Appl. No. 12/114,091, Jul. 7, 2011, Office Action.
U.S. Appl. No. 12/114,091, Apr. 5, 2012, Office Action.
U.S. Appl. No. 12/114,091, Nov. 8, 2012, Office Action.
U.S. Appl. No. 12/122,603, Mar. 3, 2011, Office Action.
U.S. Appl. No. 12/122,603, Apr. 22, 2011, Office Action.
U.S. Appl. No. 12/122,603, Sep. 23, 2011, Office Action.
U.S. Appl. No. 12/135,858, Jul. 13, 2011, Office Action.
U.S. Appl. No. 12/135,858, Feb. 16, 2012, Office Action.
U.S. Appl. No. 12/143,020, May 11, 2011, Restriction Requirement.
U.S. Appl. No. 12/143,020, Aug. 31, 2011, Office Action.
U.S. Appl. No. 12/143,020, Feb. 23, 2012, Notice of Allowance.
U.S. Appl. No. 12/338,977, Jan. 19, 2012, Office Action.
U.S. Appl. No. 12/338,977, Jul. 11, 2012, Office Action.
U.S. Appl. No. 12/338,977, Nov. 28, 2012, Office Action.
U.S. Appl. No. 12/338,977, Jun. 19, 2013, Office Action.
U.S. Appl. No. 12/393,877, Sep. 29, 2011, Office Action.
U.S. Appl. No. 12/393,877, Dec. 13, 2011, Office Action.
U.S. Appl. No. 12/393,877, May 21, 2012, Office Action.
U.S. Appl. No. 12/402,398, Mar. 9, 2010, Restriction Requirement.
U.S. Appl. No. 12/402,398, May 20, 2010, Office Action.
U.S. Appl. No. 12/402,398, Jan. 24, 2011, Office Action.
U.S. Appl. No. 12/402,398, Sep. 20, 2012, Office Action.
U.S. Appl. No. 12/402,398, Mar. 13, 2013, Notice of Allowance.
U.S. Appl. No. 12/403,256, Dec. 16, 2009, Restriction Requirement.
U.S. Appl. No. 12/403,256, Mar. 30, 2010, Office Action.
U.S. Appl. No. 12/403,256, Aug. 19, 2010, Notice of Allowance.
U.S. Appl. No. 12/403,277, Jul. 8, 2010, Restriction Requirement.
U.S. Appl. No. 12/403,277, Oct. 12, 2010, Office Action.
U.S. Appl. No. 12/403,277, Mar. 31, 2011, Office Action.
U.S. Appl. No. 12/403,277, Apr. 3, 2012, Office Action.
U.S. Appl. No. 12/403,277, Nov. 5, 2012, Office Action.
U.S. Appl. No. 12/481,377, Apr. 28, 2011, Restriction Requirement.
U.S. Appl. No. 12/481,377, Jun. 21, 2011, Office Action.
U.S. Appl. No. 12/481,377, Jan. 3, 2012, Office Action.
U.S. Appl. No. 12/481,377, Aug. 10, 2012, Notice of Allowance.
U.S. Appl. No. 12/548,274, Dec. 28, 2011, Restriction Requirement.
U.S. Appl. No. 12/548,274, Mar. 2, 2012, Office Action.
U.S. Appl. No. 12/548,274, Sep. 10, 2012, Office Action.
U.S. Appl. No. 12/608,769, Feb. 10, 2012, Office Action.
U.S. Appl. No. 12/608,769, Aug. 22, 2012, Office Action.
U.S. Appl. No. 12/608,769, Nov. 5, 2012, Notice of Allowance.
U.S. Appl. No. 12/608,773, Jun. 7, 2012, Restriction Requirement.
U.S. Appl. No. 12/608,773, Jul. 20, 2012, Office Action.
U.S. Appl. No. 12/608,773, Jan. 7, 2013, Office Action.
U.S. Appl. No. 12/642,319, Feb. 27, 2012, Restriction Requirement.
U.S. Appl. No. 12/642,319, Aug. 28, 2012, Office Action.
U.S. Appl. No. 12/684,400, Feb. 13, 2012, Restriction Requirement.
U.S. Appl. No. 12/684,400, May 9, 2012, Office Action.
U.S. Appl. No. 12/684,400, Oct. 16, 2012, Office Action.
U.S. Appl. No. 12/684,470, Dec. 20, 2011, Restriction Requirement.
U.S. Appl. No. 12/684,470, Mar. 23, 2012, Office Action.
U.S. Appl. No. 12/684,470, Aug. 30, 2012, Office Action.
U.S. Appl. No. 12/684,542, Jan. 30, 2012, Restriction Requirement.
U.S. Appl. No. 12/684,542, Apr. 16, 2012, Office Action.
U.S. Appl. No. 12/684,542, Sep. 13, 2012, Office Action.
U.S. Appl. No. 12/684,562, Dec. 28, 2011, Restriction Requirement.
U.S. Appl. No. 12/684,562, Feb. 16, 2012, Office Action.
U.S. Appl. No. 12/684,562, Aug. 21, 2012, Office Action.
U.S. Appl. No. 12/684,569, Dec. 20, 2011, Restriction Requirement.
U.S. Appl. No. 12/684,569, Jan. 27, 2012, Office Action.
U.S. Appl. No. 12/684,569, Jul. 30, 2012, Office Action.
U.S. Appl. No. 12/688,065, Mar. 13, 2012, Restriction Requirement.
U.S. Appl. No. 12/688,065, Apr. 26, 2012, Office Action.
U.S. Appl. No. 12/688,065, Oct. 12, 2012, Office Action.
U.S. Appl. No. 12/848,642, Sep. 20, 2012, Restriction Requirement.
U.S. Appl. No. 12/848,642, Nov. 9, 2012, Office Action.
U.S. Appl. No. 12/848,642, Apr. 26, 2013, Office Action.
U.S. Appl. No. 12/850,242, Aug. 6, 2012, Restriction Requirement.
U.S. Appl. No. 12/850,242, Oct. 17, 2012, Office Action.
U.S. Appl. No. 12/850,242, Apr. 18, 2013, Office Action.
U.S. Appl. No. 12/897,358, Aug. 22, 2011, Office Action.
U.S. Appl. No. 12/897,358, Jan. 12, 2012, Notice of Allowance.
U.S. Appl. No. 12/897,358, Mar. 5, 2012, Notice of Allowance.
U.S. Appl. No. 12/941,809, Dec. 13, 2011, Restriction Requirement.
U.S. Appl. No. 12/941,809, Jan. 30, 2012, Office Action.
U.S. Appl. No. 12/941,809, Jun. 1, 2012, Office Action.
U.S. Appl. No. 12/941,809, Jul. 3, 2013, Office Action.
U.S. Appl. No. 12/945,646, Jan. 20, 2011, Office Action.
U.S. Appl. No. 12/945,646, Jul. 6, 2011, Office Action.
U.S. Appl. No. 12/945,646, Oct. 26, 2011, Office Action.
U.S. Appl. No. 12/945,646, Feb. 21, 2012, Notice of Allowance.
U.S. Appl. No. 12/955,859, May 26, 2011, Restriction Requirement.
U.S. Appl. No. 12/955,859, Jul. 21, 2011, Office Action.
U.S. Appl. No. 12/955,859, Dec. 15, 2011, Office Action.
U.S. Appl. No. 12/955,859, Aug. 6, 2012, Office Action.
U.S. Appl. No. 12/955,859, May 16, 2013, Office Action.
U.S. Appl. No. 12/961,331, Dec. 4, 2012, Restriction Requirement.
U.S. Appl. No. 12/961,331, Feb. 1, 2013, Office Action.
U.S. Appl. No. 12/961,331, Jul. 3, 2013, Office Action.
U.S. Appl. No. 12/966,923, Feb. 3, 2012, Notice of Allowance.
U.S. Appl. No. 12/973,204, Mar. 7, 2012, Notice of Allowance.
U.S. Appl. No. 12/987,792, Mar. 13, 2012, Office Action.
U.S. Appl. No. 12/987,792, Sep. 17, 2012, Office Action.
U.S. Appl. No. 13/026,989, Sep. 16, 2011, Office Action.
U.S. Appl. No. 13/026,989, Jun. 8, 2012, Office Action.
U.S. Appl. No. 13/028,041, Jan. 4, 2013, Restriction Requirement.
U.S. Appl. No. 13/028,041, Feb. 26, 2013, Office Action.
U.S. Appl. No. 13/030,922, Dec. 18, 2012, Office Action.
U.S. Appl. No. 13/030,922, Jan. 31, 2013, Office Action.
U.S. Appl. No. 13/030,922, Jul. 18, 2013, Office Action.
U.S. Appl. No. 13/039,087, Jul. 17, 2012, Office Action.
U.S. Appl. No. 13/039,087, Nov. 6, 2012, Notice of Allowance.
U.S. Appl. No. 13/112,618, Mar. 29, 2013, Restriction Requirement.
U.S. Appl. No. 13/112,618, Jun. 7, 2013, Office Action.
U.S. Appl. No. 13/112,631, Mar. 29, 2013, Restriction Requirement.
U.S. Appl. No. 13/112,631, Jun. 26, 2013, Office Action.
U.S. Appl. No. 13/153,594, Jan. 29, 2013, Office Action.
U.S. Appl. No. 13/153,594, May 29, 2013, Office Action.
U.S. Appl. No. 13/308,227, Apr. 10, 2013, Office Action.
U.S. Appl. No. 13/488,233, Feb. 5, 2013, Notice of Allowance.
U.S. Appl. No. 13/490,143, Jan. 4, 2013, Restriction Requirement.
U.S. Appl. No. 13/490,143, Apr. 29, 2013, Notice of Allowance.
U.S. Appl. No. 13/525,839, Apr. 1, 2013, Office Action.
U.S. Appl. No. 13/525,839, Jul. 15, 2013, Notice of Allowance.
U.S. Appl. No. 13/615,547, Jan. 18, 2013, Office Action.
U.S. Appl. No. 13/615,547, Apr. 12, 2013, Notice of Allowance.
U.S. Appl. No. 13/615,547, Jul. 10, 2013, Issue Notification.
U.S. Appl. No. 13/791,829, May 29, 2013, Office Action.
U.S. Appl. No. 10/908,721, Jul. 18, 2013, Notice of Allowance.
U.S. Appl. No. 11/744,089, Aug. 8, 2013, Notice of Allowance.
U.S. Appl. No. 12/850,242, Aug. 6, 2013, Notice of Allowance.
U.S. Appl. No. 12/955,859, Aug. 1, 2013, Notice of Allowance.
U.S. Appl. No. 13/615,547, Aug. 7, 2013, Issue Notification.
U.S. Appl. No. 11/396,141, Aug. 21, 2013, Office Action.
U.S. Appl. No. 13/026,989, Aug. 23, 2013, Office Action.
U.S. Appl. No. 13/490,143, Aug. 21, 2013, Issue Notification.
U.S. Appl. No. 14/017,039, filed Sep. 3, 2013, Ellingwood et al.
U.S. Appl. No. 14/023,428, filed Sep. 10, 2013, Ellingwood.
U.S. Appl. No. 10/786,444, Oct. 23, 2013, Issue Notification.
U.S. Appl. No. 11/39,6141, Nov. 4, 2013, Notice of Allowance.
U.S. Appl. No. 11/411,925, Oct. 1, 2013, Office Action.
U.S. Appl. No. 11/508,662, Dec. 28, 2009, Office Action.
U.S. Appl. No. 11/508,662, Apr. 14, 2010, Office Action.
U.S. Appl. No. 11/508,662, Oct. 26, 2010, Office Action.

(56) References Cited

OTHER PUBLICATIONS

U.S. Appl. No. 12/688,065, Oct. 18, 2013, Office Action.
U.S. Appl. No. 12/961,331, Sep. 20, 2013, Advisory Action.
U.S. Appl. No. 13/111,403, Sep. 5, 2013, Office Action.
U.S. Appl. No. 13/153,594, Oct. 16, 2013, Notice of Allowance.
U.S. Appl. No. 13/308,227, Sep. 11, 2013, Office Action.
U.S. Appl. No. 13/525,839, Oct. 31, 2013, Issue Notification.
U.S. Appl. No. 13/791,829, Oct. 8, 2013, Notice of Allowance.
U.S. Appl. No. 60/711,279, filed Aug. 24, 2005, Sibbitt, Jr. et al.
U.S. Appl. No. 60/726,985, filed Oct. 14, 2005, Sibbitt Jr. et al.
U.S. Appl. No. 61/097,072, filed Sep. 15, 2008, Sibbitt Jr. et al.
U.S. Appl. No. 11/316,775, Apr. 16, 2008, Office Action.
U.S. Appl. No. 11/316,775, Aug. 6, 2008, Office Action.
U.S. Appl. No. 11/508,656, Dec. 9, 2009, Restriction Requirement.
U.S. Appl. No. 11/508,656, Mar. 25, 2010, Office Action.
U.S. Appl. No. 11/508,656, Aug. 30, 2010, Office Action.
U.S. Appl. No. 11/508,656, Feb. 10, 2014, Notice of Allowance.
U.S. Appl. No. 11/508,662, Dec. 28, 2009, Restriction Requirement.
U.S. Appl. No. 11/508,662, Apr. 14, 2010, Office Action
U.S. Appl. No. 11/508,662, Mar. 24, 2014, Office Action.
U.S. Appl. No. 11/508,715, Jan. 6, 2010, Restriction Requirement.
U.S. Appl. No. 11/508,715, Apr. 26, 2010, Office Action.
U.S. Appl. No. 11/508,715, Oct. 18, 2010, Office Action.
U.S. Appl. No. 11/508,715, Mar. 27, 2014, Office Action.
U.S. Appl. No. 12/365,397, Sep. 13, 2010, Restriction Requirement.
U.S. Appl. No. 12/365,397, Dec. 17, 2010, Office Action.
U.S. Appl. No. 12/365,397, Jun. 21, 2011, Notice of Allowance.
U.S. Appl. No. 12/559,377, Dec. 14, 2011, Restriction Requirement.
U.S. Appl. No. 12/559,377, Feb. 27, 2012, Office Action.
U.S. Appl. No. 12/559,377, Aug. 3, 2012, Office Action.
U.S. Appl. No. 13/111,403, Jun. 28, 2013, Restriction Requirement.
U.S. Appl. No. 13/111,403, Dec. 24, 2013, Office Action.
U.S. Appl. No. 14/532,537, filed Nov. 4, 2014, Sibbitt, Jr. et al.
U.S. Appl. No. 11/508,662, Jul. 25, 2014, Notice of Allowance.
U.S. Appl. No. 11/508,662, Dec. 10, 2014, Issue Notification.
U.S. Appl. No. 11/508,715, Aug. 15, 2014, Office Action.
U.S. Appl. No. 12/559,377, Jul. 30, 2014, Notice of Allowance.
U.S. Appl. No. 13/111,403, Nov. 20, 2014, Office Action.

* cited by examiner

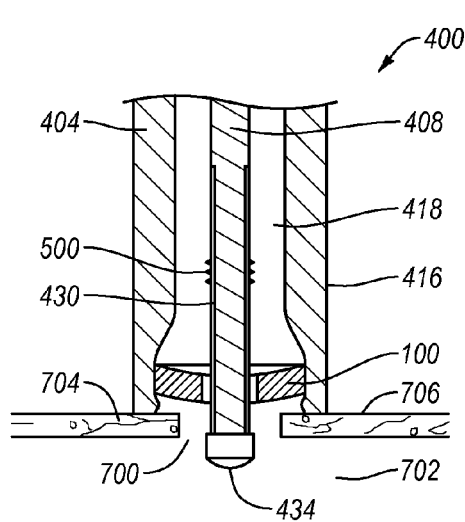
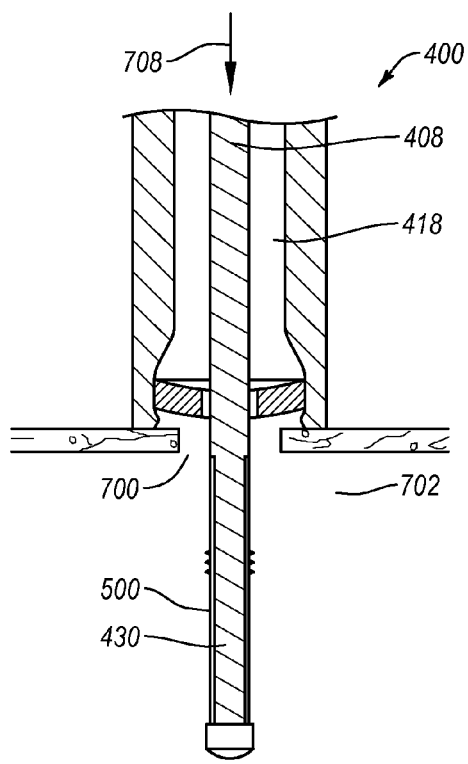
Fig. 7A  Fig. 7B
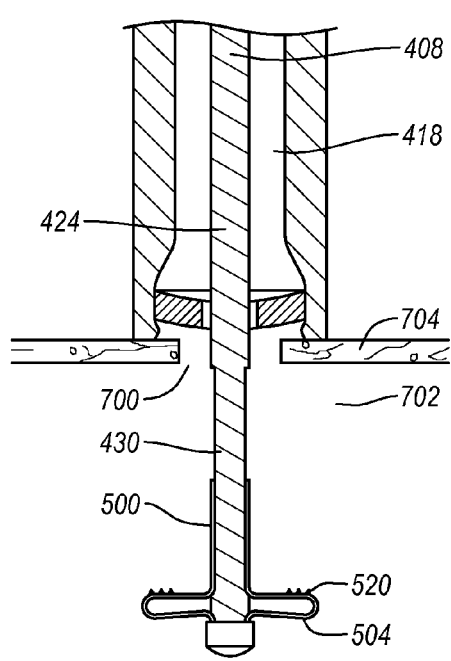
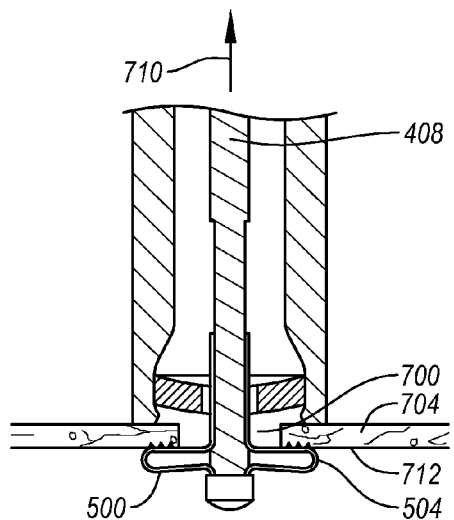
Fig. 7C  Fig. 7D

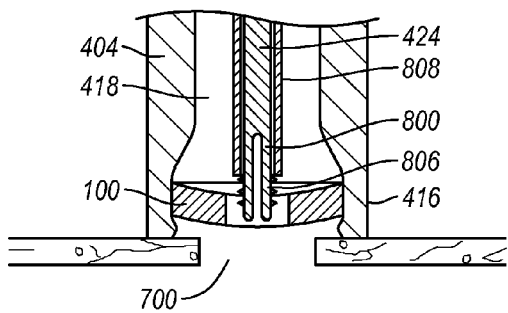
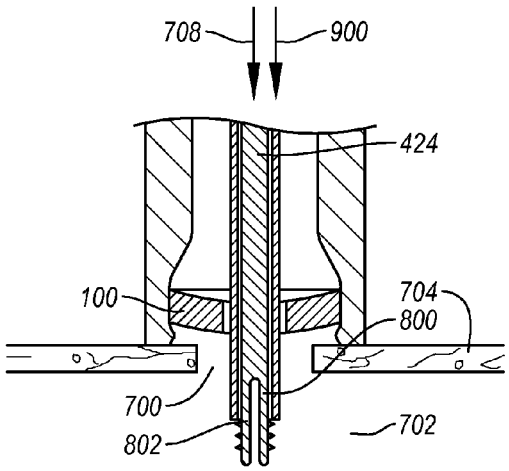
Fig. 9A
Fig. 9B
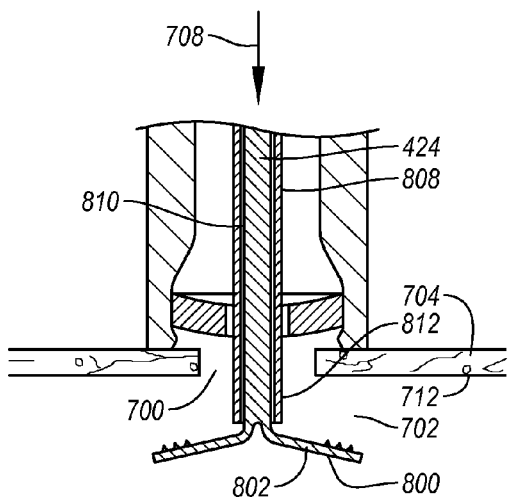
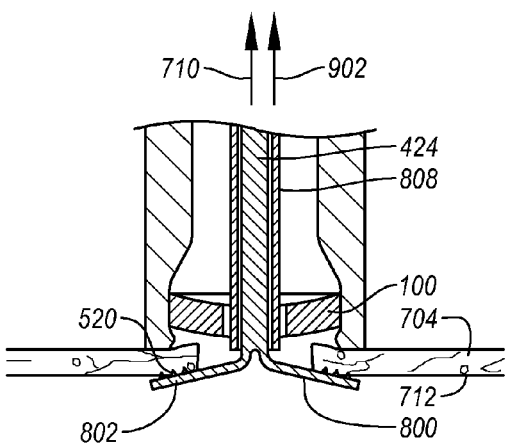
Fig. 9C
Fig. 9D

CLIP AND DEPLOYMENT APPARATUS FOR TISSUE CLOSURE

CROSS-REFERENCE TO RELATED APPLICATIONS

Not Applicable.

BACKGROUND OF THE INVENTION

1. The Field of the Invention

The present disclosure generally relates to tissue closure apparatuses and methods.

2. The Relevant Technology

During intravascular and other related medical procedures, catheters are typically inserted through an incision or puncture in the skin and underlying tissues to access an artery or vein, typically in the groin, neck, or subclavian areas of a patient. The catheter can be inserted through a puncture in the blood vessel and guided to the desired site to perform interventional procedures such as angiography, angioplasty, stent delivery, plaque removal, and infusion of a therapeutic substance.

After the procedure is completed and the catheter is removed from the patient, however, the access hole must be closed to prevent hemorrhage. This is typically achieved by applying pressure over the blood vessel manually and then by applying a pressure bandage or a compressive weight. With conventional methods, the risk of post-puncture hemorrhage is high, which can cause considerable complications. The risk of complications is exacerbated by the concomitant use of anticoagulant medications such as heparin or warfarin and by anti-platelet drugs, which are commonly used following a procedure in order to prevent clot formation and thrombus and/or to treat vascular disease.

It is generally recognized that many currently employed vascular sealing methods and devices and other tissue closure methods and devices incompletely seal holes or wounds in vascular or other tissue. Achieving complete wound closure is particularly important in sealing arterial punctures, which are relatively high pressure systems. For example, under normal blood pressure, the arterial system has a pressure of about 120/80 mmHg or more. Failure to completely close arterial holes can result in hematoma, exsanguination, and in extreme cases, may result in catastrophic consequences, such as limb amputation and death. Moreover, many currently employed vascular devices employ methods and materials that remain on the intravascular endothelial surface or otherwise in the sealed vessel. Materials that remain intravascularly can be a nidus for thrombus or intravascular mural hyperplasia with later spontaneous and catastrophic closure of the vessel.

To overcome these shortcomings, some currently employed vascular devices seal the vessel from the outside of the vessel. However, these vascular devices are typically made of stainless steel, titanium, nickel-titanium (Nitinol) or other non-bioabsorbable material. As such, these vascular devices will permanently remain within the body unless physically removed later by a physician. With a prevalence of reaccessing patients for multiple procedures, this can lead to various problems. For example, when a physician tries to reenter the blood vessel in the same location, the prior placed vascular device will prevent the physician from doing so, and could possibly cause damage to the insertion instrument being used. Furthermore, after each procedure, an additional vascular device will be attached to the blood vessel to be left permanently in the body.

BRIEF SUMMARY OF THE INVENTION

The present disclosure provides methods and apparatuses that are suitable for closure of vascular punctures or other openings in bodily tissues. The devices and methods described herein are configured for wound closure on the external surface of the wound, which allows wound healing with little endothelial disruption thereby reducing the chances of intravascular thrombosis or embolism or intimal hyperplasia. In some embodiments, the devices are bioabsorbable.

In one aspect of the invention there is provided a device for engaging tissue that includes a generally annular-shaped body disposed about a central axis. The body has a plurality of inwardly protruding members separated by corresponding intermember spaces. The body is movable between a first position where the body is substantially convex before engagement with the tissue and a second position where the body is substantially concave when the body is engaged with the tissue.

In another aspect of the invention there is provided a tissue closure device for closing an opening in a tissue having an interior surface and opposing exterior surface. The tissue closure device includes a deployment apparatus and a tissue engaging device. The deployment apparatus includes an sheath having a central longitudinal axis extending between a proximal end and a spaced apart distal end. A lumen extends between the proximal and distal ends of the sheath and is bounded by a lumen surface. The deployment apparatus also includes a tissue eversion apparatus configured to form an everted tissue region. The tissue eversion apparatus is positioned within the lumen of the sheath and deployable therefrom for engaging the interior surface of the vessel wall and everting edges of the tissue to be closed. The tissue engaging device is operatively coupled to the deployment apparatus and deliverable therefrom. The tissue engaging device includes a generally annular-shaped body disposed about a central axis. The body has an aperture extending therethrough for receiving the everted edges of the tissue and closing the opening in the tissue. The body is movable between a first position where the body is substantially convex before engagement with the tissue and a second position where the body is substantially concave when the body is engaged with the tissue.

In another aspect of the invention there is provided a method of closing an opening in a body tissue. The method includes the steps of positioning a tissue engaging device over the opening in the body tissue, the tissue engaging device being substantially convex with respect to the body tissue; forming an everted tissue region around the opening in the body tissue; and passing the everted tissue region through an aperture in the tissue engaging device, thereby causing the tissue engaging device to become substantially concave with respect to the body tissue to secure the everted tissue region within the aperture and close the opening.

In another aspect of the invention there is provided a method of closing an opening extending between an interior surface and an opposing exterior surface of a body tissue. The method includes the steps of positioning a deployment apparatus adjacent the exterior surface and over the opening in the body tissue, a tissue eversion apparatus being disposed within the deployment apparatus and a tissue engaging device being associated with the deployment apparatus and positioned over the opening of the body tissue, the tissue engaging device being substantially convex with respect to the body tissue; deploying the tissue eversion apparatus from the deployment apparatus through the opening of the body tissue so that the tissue eversion apparatus engages the interior surface of the body tissue; retracting the tissue eversion apparatus back into the deployment apparatus, the engagement of the tissue eversion apparatus with the interior surface of the body tissue causing an everted tissue region to be formed around the opening as the tissue eversion apparatus is refracted, the everted tissue region being passed through an aperture in the tissue engaging device as the tissue eversion apparatus is refracted, thereby causing the tissue engaging device to become substantially concave with respect to the body tissue to secure the everted tissue region within the aperture and close the opening; and disengaging the tissue eversion apparatus from the everted tissue region, the everted tissue region remaining secured within the tissue engaging device to close the opening and the tissue engaging device remaining substantially concave with respect to the body tissue.

These and other embodiments and features of the present invention will become more fully apparent from the following description and appended claims, or may be learned by the practice of the invention as set forth hereinafter.

Embodiments of the present invention may provide several advantages over conventional designs. For example, embodiments of a closure device according to the present invention may provide an improved, more complete closure of a vessel opening than prior designs. Furthermore, embodiments of a closure device according to the present invention may be made of a bioabsorbable material so as to become absorbed into the body after a certain amount of time. This may prevent problems of reaccessing patients for multiple procedures. Other advantages may also be provided by the present invention.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope. In the drawings, like numerals designate like elements.

FIGS. 7A-7H illustrate a method of closing an opening in a tissue wall using the deployment apparatus of FIG. 4, the tissue eversion apparatus of FIGS. 5A and 5B, and the tissue engaging device of FIG. 1;

FIGS. 9A-9F illustrate a method of closing an opening in a tissue wall using the tissue eversion apparatus of FIGS. 8A and 8B.

DETAILED DESCRIPTION OF THE PREFERRED EMBODIMENTS

As used in the specification and appended claims, directional terms, such as "top," "bottom," "up," "down," "upper," "lower," "proximal," "distal," and the like are used herein solely to indicate relative directions in viewing the drawings and are not intended to limit the scope of the claims in any way.

The present disclosure provides methods and apparatuses that are suitable for closure of vascular punctures or other openings in bodily tissues. The devices and methods described herein are configured for wound closure on the external surface of the wound, which allows wound healing with little endothelial disruption thereby reducing the chances of intravascular thrombosis or embolism or intimal hyperplasia. In some embodiments, the closure elements are bioabsorbable.

Generally, the apparatuses and methods described herein can be used with any type of body tissue that has sufficient strength to be held together by the tissue engaging devices described hereinafter. By way of example only, embodiments of the present invention can be used to close openings in tissues that have a wall or membrane function, e.g., pulmonary, intestinal, vascular, urethral, gastric, renal or other wall structures, or in membranes, e.g., amniotic or pericardial membranes. Openings in other types of tissues can also be closed using embodiments of the present invention. Although many types of body tissue can be closed by the methods and apparatuses disclosed herein, the description included herein refers to "vessels" for convenience.

Furthermore, the apparatuses and methods described herein can be used with large and small hole punctures or other openings in the body tissue. By way of example, the tissue engaging devices of the present invention can be sized to close holes from 5 French to 30 French or larger. It may also be possible to close holes of other sizes.

Figure 1:
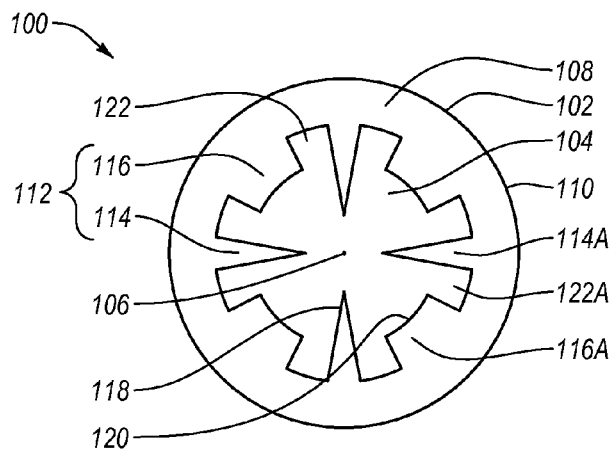
FIG. 1 is a top view of a first embodiment of a tissue engaging device, in accordance with the present invention.

Turning now to the drawings, FIG. 1 shows a first embodiment of a tissue engaging device or clip 100 for closing an incision, puncture, or other passage through tissue, such as, e.g., communicating with a blood vessel or other body lumen. Clip 100 includes a body 102, which may be generally annular in shape, bounding an aperture 104 and surrounding a central axis 106. As used herein, an "annular-shaped body" includes any hollow body, e.g., including one or more structures surrounding an aperture, whether the body is substantially flat or curved or has a significant thickness or depth. Thus, although an annular-shaped body may be circular, it may include other noncircular shapes as well, such as elliptical or other shapes that are asymmetrical about a central axis.

Body 102 includes an outer region 108 that encircles aperture 104 and has an outer circumferential edge 110. Body 102 may include a plurality of tissue engaging members 112 that extend from outer region 108 into aperture 104 and generally towards central axis 106. Tissue engaging members 112 can comprise any structure that is designed to engage the tissue once the tissue has been positioned within aperture 104. This can include structures designed to puncture or otherwise penetrate the tissue or to structures designed to press against the tissue without penetration therein. For example, in the depicted embodiment, tissue engaging members 112 comprise tines 114 and tabs 116 extending into aperture 104. With a substantially pointed tip 118, tines 114 may penetrate the tissue or press against the tissue without penetration. Tabs 116 are designed to generally press against the tissue without penetrating the tissue, although in some embodiments, tabs may also penetrate the tissue. Other types of tissue engaging members 112 may also be used.

Each tine 114 may extend from outer region 108 to spaced apart tip 118 and may be biased to extend generally inwardly, e.g., towards one another and/or generally towards central axis 106. Tines 114 may be provided in pairs opposite from one another or may be provided otherwise symmetrically or asymmetrically with respect to central axis 106.

Tines 114 may include a variety of pointed tips, such as, e.g., a bayonet tip, and/or may include barbs for penetrating or otherwise engaging tissue. For example, to increase the penetration ability of clip 100 and/or to lower the insertion force required to penetrate tissue, each tine 114 may include a tapered edge extending towards tip 118 along one side of tine. Alternatively, each tine 114 may be provided with a tapered edge on each side of the tine extending towards tip 118.

Each 116 tab may extend from outer region 108 to a spaced apart inner circumferential edge 120 and may be biased to extend generally inwardly, e.g., towards one another and/or generally towards central axis 106. Tabs 116 may be provided in pairs opposite from one another or may be provided otherwise symmetrically or asymmetrically with respect to central axis 106.

Tissue engaging members 112 are separated by intermember spaces 122, which are portions of aperture 104 which are positioned between adjacent tissue engaging members 112. For example, tine 114A and tab 116A are separated by intermember space 122A.

Tines and tabs 114, 116 can be combined in any order. For example, tines 114 and tabs 116 can alternate with each other, as in the depicted embodiment. Other combinations can also be used. In addition, clip 100 can employ the same number of tines and tabs 114, 116 or the number of one can be more than the other. In some embodiments, more tines 114 are present than tabs 116, while in other embodiments, more tabs 116 are present.

Clip 100 can be comprised of a biocompatible material. Examples of such materials include stainless steel, titanium, and nickel titanium alloys. In addition, clip 100 can be comprised of a bioabsorbable material. Examples of such materials include PGA and magnesium alloys. Other materials are also possible. By being comprised of a bioabsorbable material, clip 100 may dissolve and become absorbed into the body after the opening in the tissue has been closed. Because clip 100 may be absorbed into the body, the surgeon in future procedures will not be prevented from reaccessing a similar area of the tissue as is the case with many conventional clips.

Figure 2A:
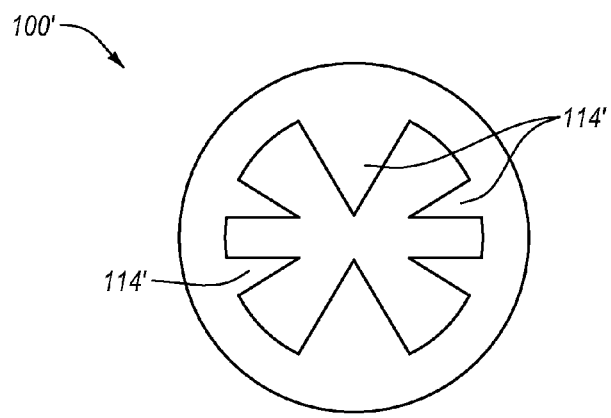
FIGS. 2A and 2B are top views of alternative embodiments of tissue engaging devices, in accordance with the present invention.
Figure 2B:
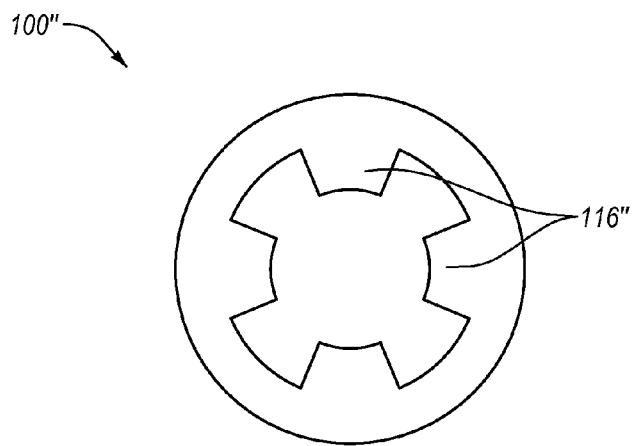

FIGS. 2A and 2B show alternative embodiments of clips 100' and 100" based on clip 100 of FIG. 1. While clip 100 incorporates a mixture of tines and tabs 114, 116, clip 100' of FIG. 2A includes only tines 114' with no tabs. Furthermore, while all of tines 114 of clip 100 are substantially the same length, tines 114' of clip 100' are of varying lengths. Conversely, clip 100" of FIG. 2B includes only tabs 116" with no tines, and the tabs can be of varying sizes, if so desired. Other combinations of sizes and numbers of tines and tabs can alternatively be used. Clips 100' and 100" as well as any derivatives thereof, can be comprised of the same types of materials as clip 100, discussed above.

Figure 3A:
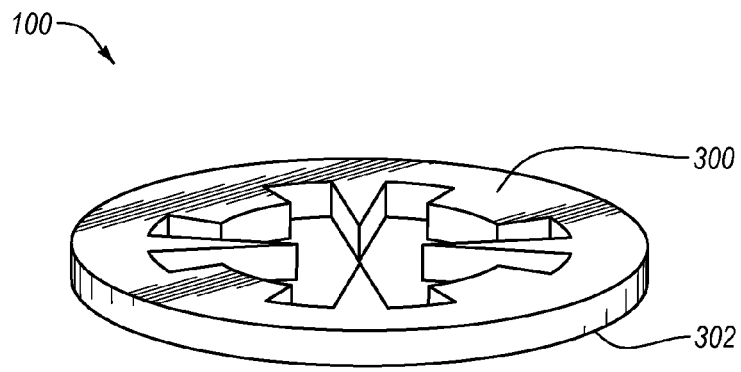
FIG. 3A is a perspective side view of a tissue engaging device having a substantially planar configuration.
Figure 3B:
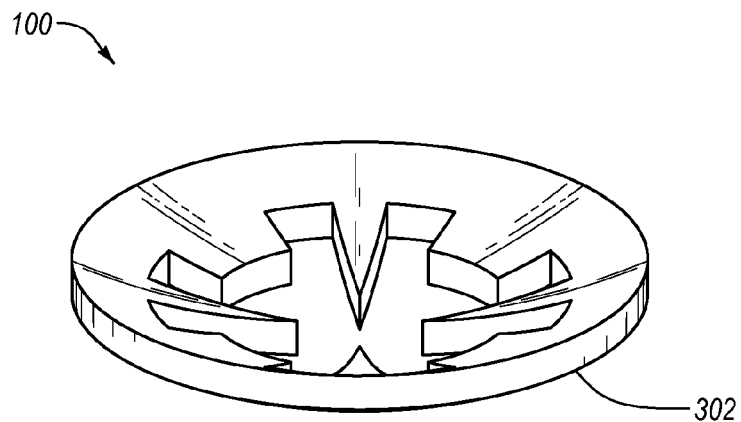
FIGS. 3B and 3C are perspective side views of a tissue engaging device having a curved configuration, respectively showing the tissue engaging device in a convex state and a concave state.
Figure 3C:
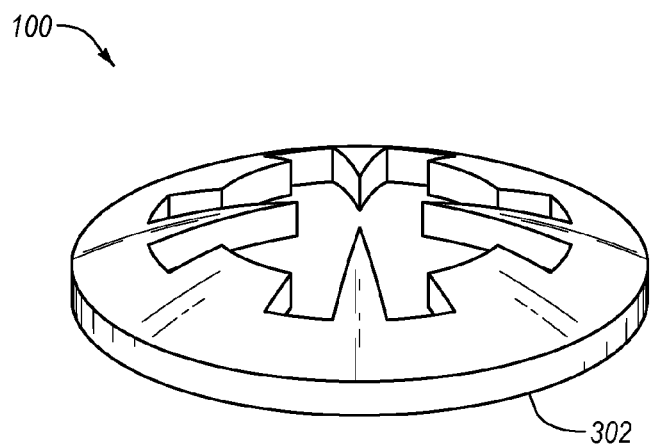

Any of the clips disclosed herein can be substantially planar or have a curvature associated therewith. For example, FIG. 3A shows clip 100 having a top surface 300 and an opposing bottom surface 302 in a substantially planar configuration. Alternatively, FIGS. 3B and 3C show clip 100 in a cup-shaped configuration, with clip 100 being in a convex state in FIG. 3B with respect to the bottom surface 302 that faces the tissue and a concave state in FIG. 3C. Clip 100 can be movable between the two states shown in FIGS. 3B and 3C, as discussed below. For example, in one embodiment, clip 100 is designed to bias towards the convex state shown in FIG. 3B and be moved to and remain in the concave state shown in FIG. 3C when the everted tissue is pulled up and through clip 100.

Figure 3D:
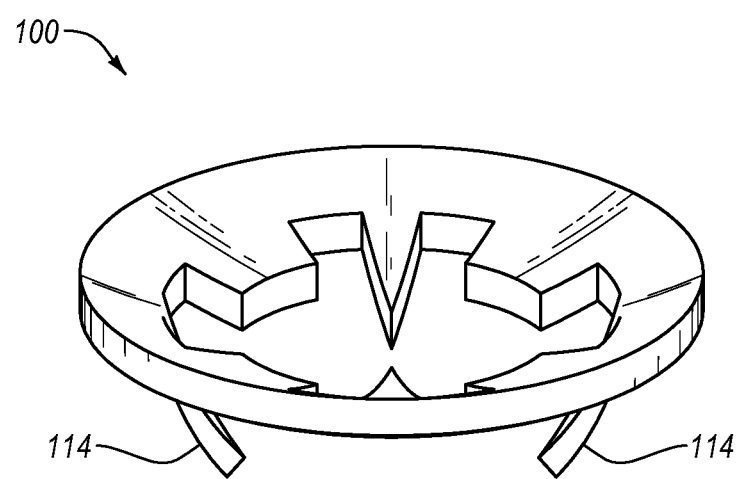
FIG. 3D is a perspective side view of an alternative tissue engaging device in a convex state.

As shown in FIGS. 3B and 3C, the tines and tabs can be configured to extend inward so as to align with the specific convex and/or concave shape of clip 100. Alternatively, one or more of the tines or tabs can be configured to extend in a different direction so as to not align with the specific convex or concave shape. For example, FIG. 3D shows an alternative embodiment of clip 100 in which an opposing pair of tines 114 extend outward and down from the rest of the clip and are thus not aligned with the convex shape of the clip. This can be advantageous in it can allow the capture of more tissue during the eversion process because the extended tine can contact the tissue earlier and further away from the body of the clip.

Figure 4A:
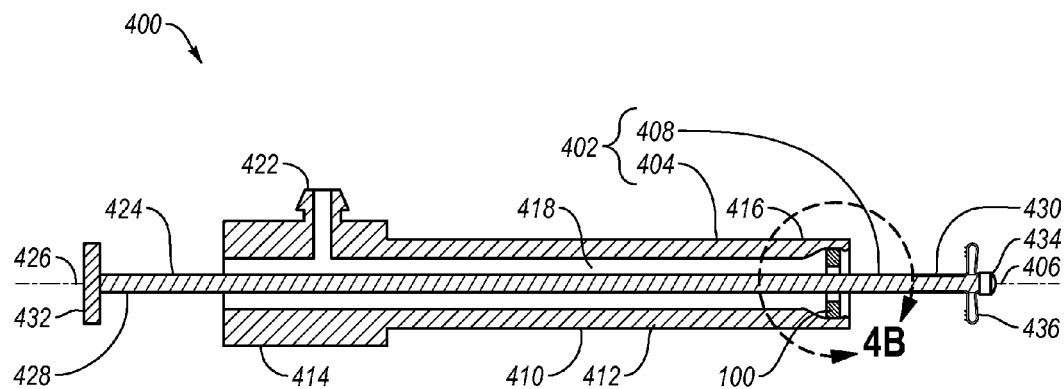
FIG. 4A is a cross sectional side view of a deployment apparatus having an sheath and a tissue eversion assembly, the deployment apparatus being suitable for delivering any of the tissue engaging devices shown in FIGS. 1 and 2.

The clips of the present invention may be delivered using various apparatuses and methods. Referring now to FIG. 4A, a tissue closure device 400 for closing an opening in a tissue according to one embodiment is depicted. Tissue closure device 400 includes a deployment apparatus 402 with clip 100 being releasably mounted thereon. Deployment apparatus 402 is used to deliver clip 100 to the tissue opening and manipulate the tissue so as to secure the tissue with the clip and thereby close the opening.

Generally, deployment apparatus 402 can include a sheath 404 having a longitudinal axis 406 and a tissue eversion assembly 408 slidably mounted therein. Sheath 404 can include a substantially rigid, semi-rigid, or substantially flexible tubular body 410 having a sidewall 412 extending longitudinally between a proximal end 414 and an opposing distal end 416. Sidewall 412 can bound a lumen 418 that extends along longitudinal axis 406 between the two ends 414, 416. Lumen 418 can have a size for inserting one or more devices therethrough, such as a catheter, guide wire, and the like (not shown). Sheath 404 may also include one or more seals (not shown), such as a hemostatic valve, within lumen 418 at or near proximal end 414 that provides a fluid-tight seal, yet accommodates inserting one or more devices into the lumen 418 without fluid passing proximally from sheath 404.

Figure 4B:
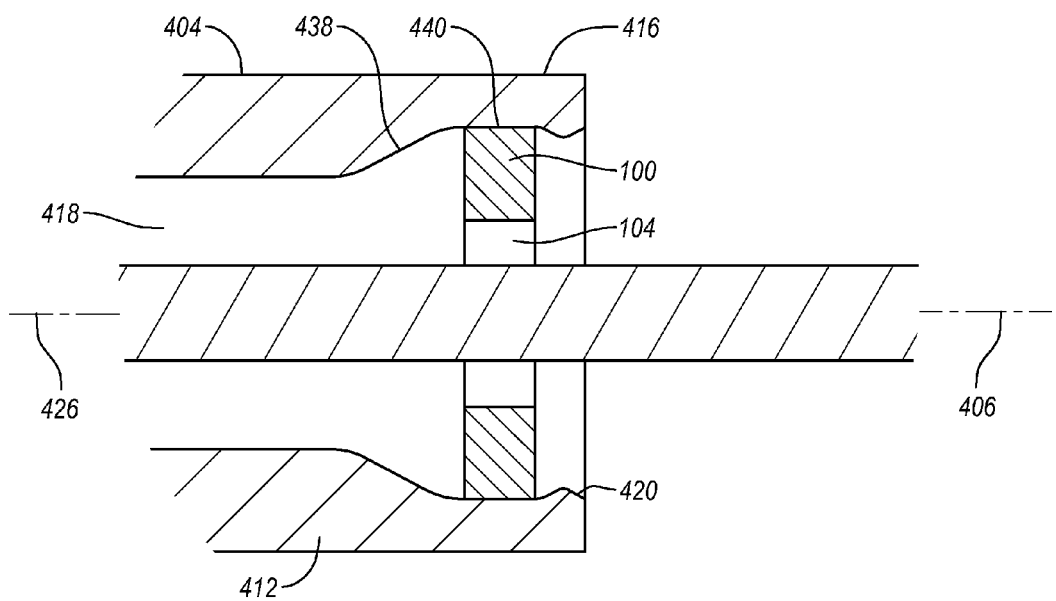
FIG. 4B is a close up view of a portion of FIG. 4A.

As particularly shown in FIG. 4B, at distal end 416 of sheath 404, lumen 418 is sized to receive clip 100 and to releasably retain clip 100 until the clip has been positioned over the opening and everted tissue has been received within the clip, as discussed below. When clip 100 is positioned within lumen 418, aperture 104 in the middle of clip 100 aligns with longitudinal axis 406 of lumen 418 so that everted tissue can be pulled up and into aperture 104, as discussed in more detail below.

As shown in the depicted embodiment, sidewall 412 narrows at distal end 416 so as to form an annular taper 438 thereat. As a result, an annular channel 440 is formed at distal end 416 of sheath 404 that has a larger diameter than the portion of lumen 418 proximal of taper 438. As a result, clip 100 can be positioned within channel 440, with taper 438 preventing clip 100 from moving proximally further into lumen 418.

An annular ridge 420 or similar retaining member can extend from sidewall 412 into lumen 418 to releasably retain clip 100 within the lumen. The retaining member 420 can be designed to retain clip 100 within lumen 418 until a distal force of a predetermined strength overcomes the retaining force and dislodges clip 100 from lumen 418. For example, as discussed below, a force caused by everted tissue that has been positioned within clip 100 by a tissue eversion apparatus can provide enough force to dislodge the clip. Other dislodging forces are also possible.

Figure 4C:
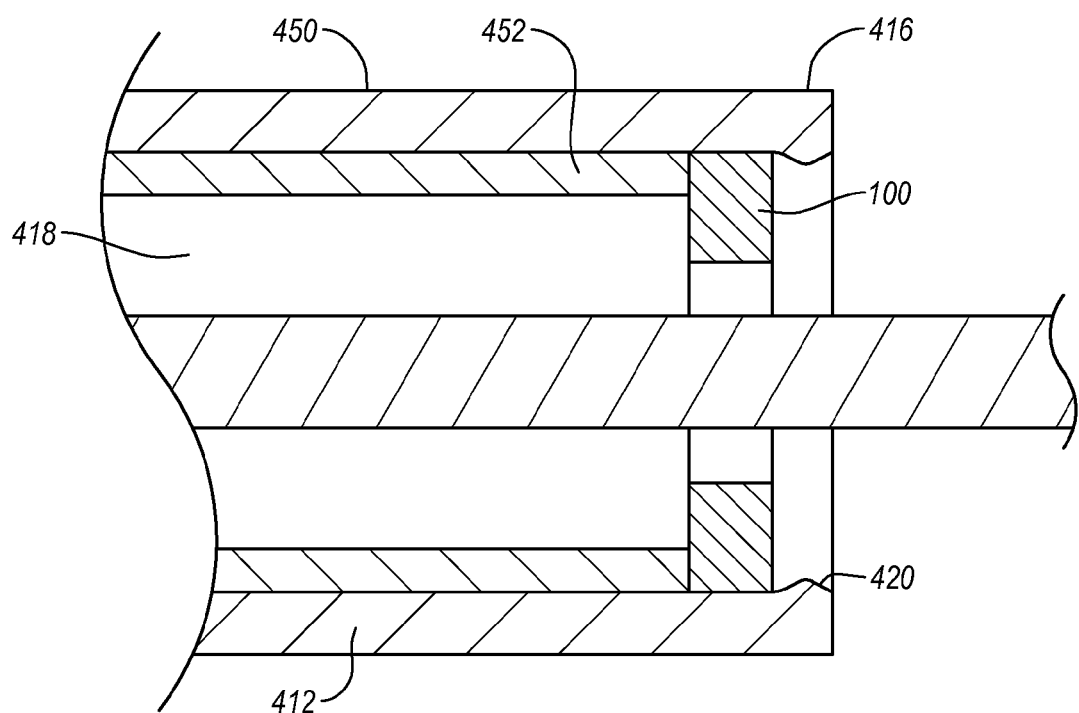
FIG. 4C is an close up view of an alternative sheath having an inner sheath positioned therein.

In an alternative embodiment, instead of having sheath 404 tapered at distal end 416 to form channel 440, an inner sheath can be used in conjunction with sheath 404 to prevent clip 100 from moving proximally into lumen 418. For example, FIG. 4C shows an alternative embodiment of a sheath 450 having an inner sheath 452 positioned within lumen 418. Sheath 450 is similar to sheath 404 except that sidewall 412 does not taper at distal end 416. Instead, inner sheath 452 is positioned at distal end 416 adjacent to the proximal side of clip 100. Inner sheath 452 prevents clip 100 from moving proximally further into lumen 418.

In some embodiments, inner sheath 452 can be slidable within lumen 418 so as to be removable therefrom. In these embodiments, unlike sheath 404, sheath 450 can allow clip 100 to be initially inserted into lumen 418 at the proximal end of sheath 450 and slid to its initial position at distal end 416. Inner sheath 452 can thereafter be slid into lumen 418 at the proximal end of sheath 450. A slidable inner sheath 452 can also be used to force clip 100 out of distal end 416 of lumen 418. After tissue has been everted into clip 100, inner sheath 452 can be pushed distally within lumen 418 against the proximal side of clip 100 with enough force to cause clip 100 to overcome the retaining force of retaining member 420 and dislodge clip 100 from lumen 418, thereby ejecting clip 100 from sheath 404.

Returning to FIG. 4A, sheath 404 may optionally include a side port 422 that communicates with lumen 418, for example, to deliver fluids into lumen 418. Alternatively, or in addition, side port 422 may be used to provide a "bleed back" indicator. An exemplary "bleed back" indicator and related methods of use are disclosed in application Ser. No. 09/680,837, filed Oct. 6, 2000 (now U.S. Pat. No. 6,626,918), entitled "Apparatus and Methods for Positioning a Vascular Sheath," which is assigned to the assignee of the present application. The disclosure of the '837 application and any other references cited therein are fully incorporated by reference herein.

Tissue eversion assembly 408 can include a rigid, semi-rigid, or flexible tubular body 424 (such as an elongate rail) with a longitudinal axis 426. Tubular body 424 can have a proximal end region 428 and a distal end region 430 and can include a predetermined length and a predetermined outer cross-section, both of which can be of any suitable dimension that will slidably fit within lumen 418 of sheath 404. When tissue eversion assembly 408 is positioned within lumen 418, longitudinal axis 426 of tissue tubular body 424 may align with longitudinal axis 406 of sheath 404.

Proximal end region 428 of tissue eversion assembly 408 can include a handle 432 or other actuation device to extend or retract distal end region 430 into or out of distal end 416 of sheath 404. Handle 432 can also include manipulator devices to manipulate a tissue eversion apparatus, as discussed below. Distal end region 430 of tissue eversion assembly 408 can include a substantially rounded, soft, and/or flexible distal end or tip 434 to facilitate advancement and/or retraction of distal end region 430 into a blood vessel or other opening in tissue. As desired, a pigtail or J-tip (not shown) may be provided on tip 434 to further aid atraumatic advancement of distal end region 430.

Tissue eversion assembly 408 can also include a tissue eversion apparatus to facilitate the formation of an everted tissue region by engaging the interior surface of the tissue. For example, in the depicted embodiment, a tissue eversion apparatus 436 is positioned at distal end region 430 of tissue eversion assembly 408.

Figure 5A:
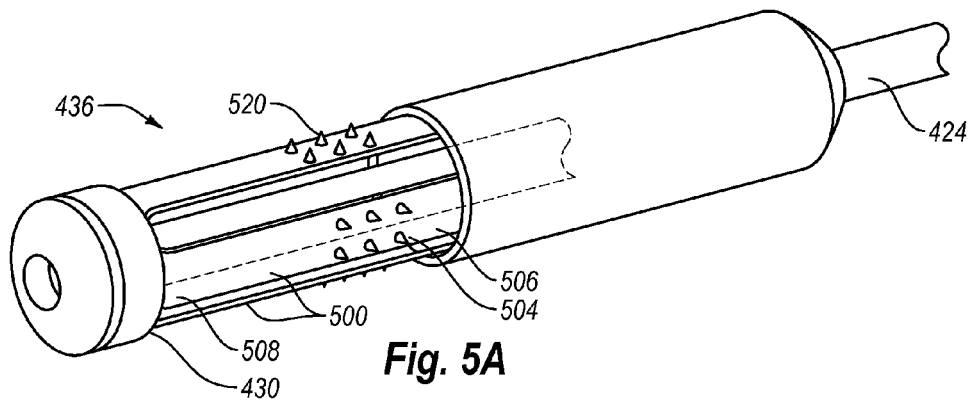
FIGS. 5A and 5B are close-up perspective views of a tissue eversion apparatus of the tissue eversion assembly shown in FIG. 4A, in unexpanded and expanded states, respectively.
Figure 5B:
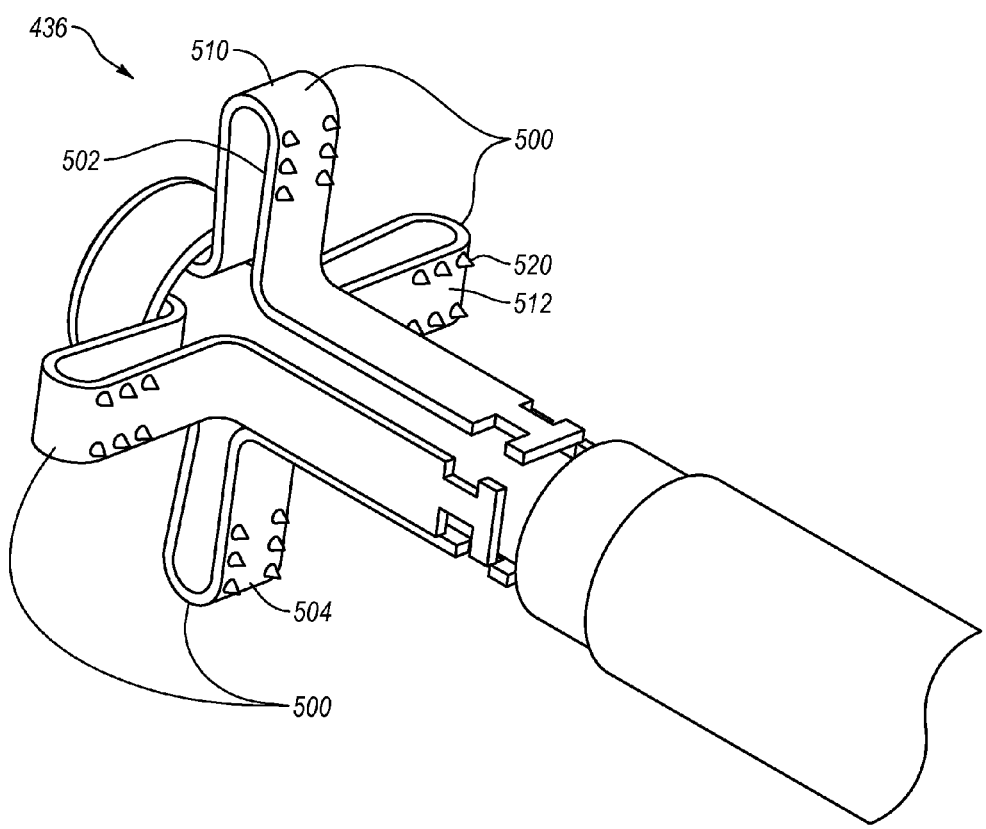

Turning to FIGS. 5A and 5B, tissue eversion apparatus 436 can comprise a plurality of substantially flexible members 500 selectably controllable between an unexpanded state, as shown in FIG. 5A, and an expanded state, as shown in FIG. 5B. Although four substantially flexible members 500 are depicted, it is appreciated that more or less substantially flexible members can be used.

Each substantially flexible member 500 has an inner surface 502 and an opposing outer surface 504 extending from a proximal end 506 to a spaced apart distal end 508. As shown in FIG. 5A, when tissue eversion apparatus 436 is in the unexpanded state, substantially flexible members 500 are substantially axially aligned with tubular body 424, with outer surfaces 504 facing outward from body 424. This helps to facilitate insertion of tissue eversion apparatus 436 through an opening through tissue, as discussed below.

Conversely, when tissue eversion apparatus 436 is in the expanded state, substantially flexible members 500 are flexed outward, as shown in FIG. 5B. In this expanded state, a portion of each substantially flexible member 500 forms a loop 510 with a portion 512 of the outer surface 504 of loop 510 facing proximally. In the expanded state, tissue eversion apparatus 436 is capable of engaging tissue positioned about an opening after tissue eversion apparatus 436 has been positioned through the opening, as discussed in detail below. Substantially flexible members 500 can be made of a material that allows substantially flexible members 500 to move easily between the unexpanded and expanded states. For example, substantially flexible members 500 can be made of stainless steel, nickel, titanium or the like. Other materials can also be used.

A control member (not shown), such as a rod, wire, or other elongate member, may be moveably disposed within a lumen (not shown) formed by tubular body 424 and extending substantially between proximal end region 428 and distal end region 430. The control member may extend from handle 432 (See FIG. 4A) to a distal end region of the control member coupled with distal end region 430 of body 424 and/or the movable end regions of substantially flexible members 500. By moving tubular body 424 axially relative to the control member, distal end region 430 and/or substantially flexible members 500, can be selectively transitioned between the unexpanded and expanded states. An exemplary control member and related methods of use are disclosed in copending U.S. application Ser. No. 12/135,858 filed on Jun. 9, 2008 and entitled "Antimicrobial Closure Element and Closure Element Applier," which is assigned to the assignee of the present application. The disclosures of the '858 application and any references cited therein are expressly incorporated herein by reference.

One or more tissue engaging members can be integrally formed with or otherwise attached to each substantially flexible member 500 so as to engage the tissue when tissue eversion apparatus 436 comes into contact with the tissue while in the expanded state, as discussed below. For example, in the depicted embodiment, the tissue engaging members comprise one or more barbs 520 extending from the outer surface 504 of each substantially flexible member 500. Barbs 520 can be positioned on the portion 512 of outer surface 504 that faces proximally in the expanded state, as shown in FIG. 5B. Barbs 520 can be made of metal, plastic, or other suitable rigid or semi-rigid material. Alternatively, barbs 520 can be integrally formed with flexible member 500 and thus made of the same material. Any desired number of barbs 520 can be included on each substantially flexible member 500. Other types of tissue engaging members can also be used, such as needles, hooks, anchors, temporary adhesives or the like.

Figure 6:
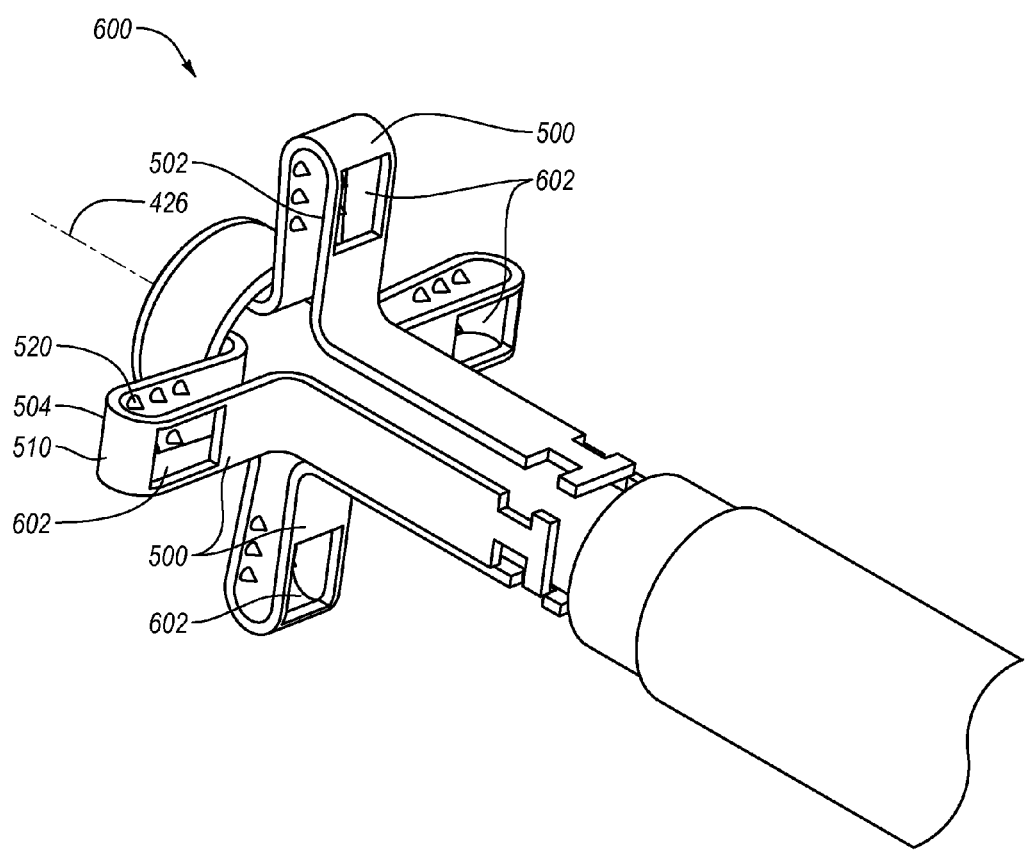
FIG. 6 is a close-up perspective view of an alternative embodiment of a tissue eversion apparatus in an expanded state.

FIG. 6 shows an alternative embodiment 600 of a tissue eversion apparatus. Tissue eversion apparatus 600 is similar to tissue eversion apparatus 436 except that instead of tissue engaging members 520 being positioned on outer surface 504 of loop 510 of each substantially flexible member 500, the tissue engaging members 520 of tissue eversion apparatus 600 extend from the inner surface 502 of loop 510. To facilitate tissue engaging members 500 engaging the tissue, a window 602 is formed in the substantially flexible member for the tissue engaging members to extend through.

As shown in FIG. 6, tissue engaging members 520 are formed with or otherwise attached to the proximal facing portion of inner surface 502 of each loop 510 formed on substantially flexible members 500 when the tissue eversion apparatus 600 is in the expanded state. Window 602 is formed on the portion of loop 510 opposing tissue engaging members 520 so that tissue engaging members 520 can project through window 602 when tissue eversion apparatus 600 is in the expanded state. To facilitate this, tissue engaging members 520 are typically longer than the width of substantially flexible member 500 so that tissue engaging members 520 can extend beyond window 602 and engage tissue.

Because tissue engaging members 500 are disposed on inner surface 502 of substantially flexible members 500, tissue engaging members 520 face inward (i.e., toward longitudinal axis 426) when substantially flexible member 500 is in the unexpanded state. This can help to prevent tissue engaging members 520 from inadvertently snagging or otherwise contacting the tissue while tissue eversion apparatus 600 is passed through an opening in the tissue while in the unexpanded state.

Turning to FIGS. 7A-7H, a method of sealing and/or closing a passage through tissue, such as an opening 700 communicating with a blood vessel or other body lumen 702 through a wall 704 thereof, using tissue closure device 400 will now be discussed. Applicant notes that all of the disclosed methods herein are exemplary only and that other methods of sealing and/or closing a passage through tissue using tissue closure device 400 can also be performed.

Initially, tissue closure device 400 is assembled. To do this, clip 100 is removably secured within lumen 418 at distal end 416 of sheath 404, as discussed above, so as to be positioned as shown in FIG. 7A. In the depicted embodiment, a cup-shaped clip is used, although a substantially planar clip, such as that shown in FIG. 3A, can alternatively be used. Clip 100 is positioned within lumen 418 to be convex with respect to the tissue in the biased position of the clip. In this position, ridge 420 (see FIG. 4B) secures clip 100 within lumen 418, as discussed above.

To complete the assembly of tissue closure device 400, distal end region 430 of tissue eversion assembly 408 is slidably received within lumen 418 of sheath 404 at proximal end 414 (see FIG. 4A). Tissue eversion assembly 408 is then slid toward distal end 416 of sheath 404 so as to be positioned within lumen 418 as shown in FIG. 7A. Substantially flexible members 500 are in the unexpanded state as tissue closure device is assembled. Tissue eversion assembly 408 can be positioned within lumen 418 before or after clip 100 has been positioned within lumen 418. When both tissue eversion assembly 408 and clip 100 have been positioned within lumen 418, distal end region 430 of tissue eversion assembly 408 (including tip 434, if used) is disposed adjacent clip 100 at distal end 416 of sheath 404, as shown in FIG. 7A.

Tissue closure device 400 is inserted into the body so that distal end 416 of sheath 404 abuts the outer surface 706 of vessel wall 704 and is positioned directly over opening 700 as shown in FIG. 7A. This can be done either before or after tissue eversion assembly 408 has been inserted into lumen 418. A guide wire can be used to aid in positioning tissue closure device, as is known in the art, either by receiving the guide wire within lumen 418 or a lumen formed in tissue eversion assembly 408. A bleed back lumen or other indicating method or apparatus known in the art can also be used to indicate when tissue closure device 400 is in position.

As shown in FIG. 7B, once tissue closure device 400 is in position above opening 700, an external deploying force, denoted by arrow 708, is then applied to tissue eversion assembly 408 by pushing distally on handle 432 (See FIG. 4A) or other actuating device. The deploying force 708 causes distal end region 430 of tissue eversion assembly 408 to extend through opening 700 and into vessel lumen 702.

Once distal end region 430 of tissue eversion assembly 408 has been extended into body lumen 702, the control member and/or tubular body 424 are axially moved relative to each other so as to cause substantially flexible members 500 to transition to the expanded state, as shown in FIG. 7C. Tissue engaging members 520 in the form of barbs are positioned on outer surface 504 of each substantially flexible member 500 so as to face proximally (i.e., toward vessel wall 704 adjacent to opening 700) when substantially flexible members 500 are in the expanded state.

An external retracting force, denoted by arrow 710 in FIG. 7D, is then applied to tissue eversion assembly 408 by pulling proximally on handle 432 (See FIG. 4A) or other actuating device. This causes the expanded substantially flexible members 500 to move proximally toward opening 700 in vessel wall 704. Substantially flexible members 500 continue moving proximally until outer surfaces 504 thereof contact the inner surface 712 of vessel wall 704 surrounding opening 700, as shown in FIG. 7D. As substantially flexible members 500 move toward vessel wall 704, barbs 520 engage inner surface 712 of vessel wall 704 and extend into the wall.

Figure 7E:
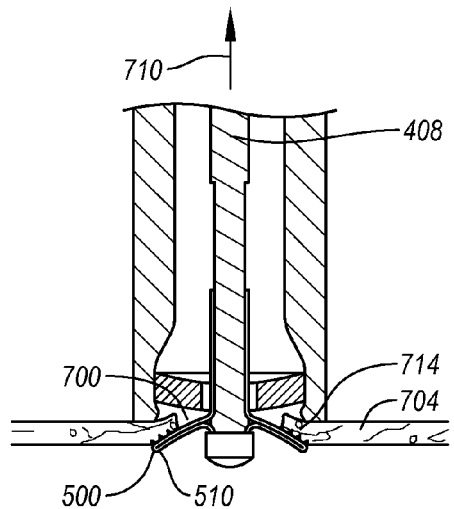

As external retracting force 710 is maintained on tissue eversion assembly 408, substantially flexible members 500 continue moving proximally. As they do so, vessel wall 704 surrounding opening 700 begin to evert and form an everted tissue region 714 as a result of the engagement with barbs 520, as shown in FIG. 7E. As a result, the engaged tissue may begin to exert a resistive force on substantially flexible members 500, causing substantially flexible members 500 to begin to bend distally. As a result, loops 510 begin to move inward, thereby causing the everted tissue region 714 to also be pulled inward, as shown in FIG. 7E.

Figure 7F:
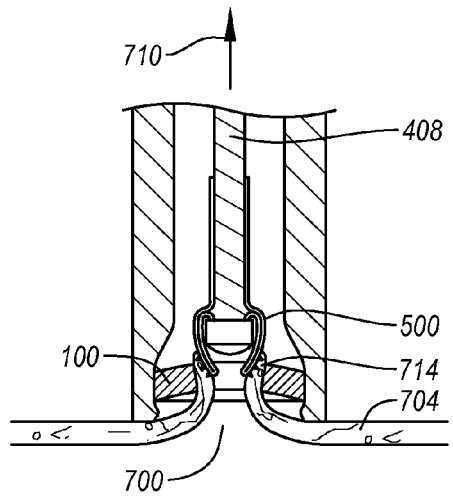

As external retracting force 710 continues, everted tissue region 714 is pulled proximally and inward into lumen 418 and through clip 100 by substantially flexible members 500, as shown in FIG. 7F. As everted tissue region 714 is pulled proximally through clip 100, the everted tissue begins to contact and exert a proximal force on tines 114 and/or tabs 116 (see FIG. 1) of clip 100. This proximal force causes clip 100 to transition or invert from the convex shape to a concave shape with respect to vessel wall 704, as shown in FIG. 7F. The tines and/or tabs also cause the edges of the everted tissue region 714 to constrict inward so as to begin to press tightly together.

Figure 7G:
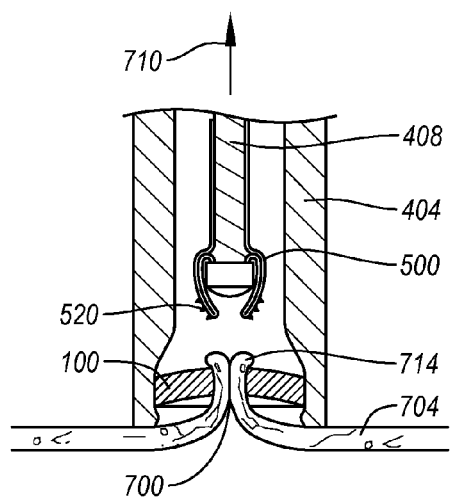

At some point, because of the retaining force of the clip the force exerted by clip 100 on the tissue eversion region 714 causes the tissue in the tissue eversion region 714 to pull away and disengage from barbs 520, as shown in FIG. 7G. Once this occurs, substantially flexible members 500 are pulled proximally away from everted tissue region 714. With substantially flexible members 500 no longer engaged to the inner surface of everted tissue region 714, the everted tissue presses tightly together due to the tines and/or tabs of clip 100, thereby completely closing opening 700. Everted tissue region 714 is now secured within clip 100, thereby keeping opening 700 closed. Furthermore, the constricted everted tissue region 714 disposed between the tines and/or tabs prevents clip 100 from reverting back to the original convex shape.

Figure 7H:
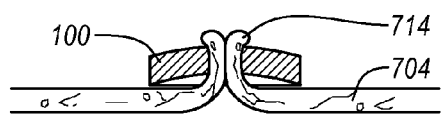

Once barbs 520 have disengaged from the everted tissue, tissue eversion assembly 408 and sheath 404 can be removed from the body. As sheath 404 is removed, a retaining force is exerted on clip 100 by its engagement with tissue eversion region 714. This force is larger than the retaining force caused by the ridge 420 (see FIG. 4B) within lumen. As such, as sheath 404 is removed from the body, clip 100 remains within the body, secured to vessel wall 704 as shown in FIG. 7H. Because clip 100 is biased toward the convex shape, the tines and/or tabs of clip 100 will continue to exert a distal force when clip 100 is in the concave shape to attempt to cause clip 100 to return to the convex shape. However, as noted above, as a result of the constricted everted tissue 714 disposed through clip 100, clip 100 will remain in the concave shape. Because of this, an added closing force is continuously exerted on everted tissue region 714 by the tines and/or tabs of clip 100 as the tines and/or tabs attempt to return clip 100 to the convex shape. This added force helps to maintain the secure nature of the closure of opening 700.

If clip 100 is made of a bioabsorbable material, clip 100 will dissolve and be absorbed into the body after the tissue has grown together over opening 700. This can aid the surgeon in future procedures by allowing the surgeon to reaccess a similar area of the tissue without having to remove or avoid the clip.

As noted above, a planar tissue engaging device can be used instead of an inverting curved tissue engaging device. If a planar tissue engaging device is used, such as clip 100 shown in FIG. 3A, the same method of sealing and/or closing a passage through tissue can be used as discussed above with reference to FIGS. 7A-7H. However, unlike the inverting clip, as the everted tissue region is pulled through the planar clip by the barbs, the clip will not invert from a convex shape to a concave shape. Instead, the planar clip may remain planar during the sealing/closing method. As a result, when the sheath has been removed, the tines and/or tabs of the planar clip may not impose an added closing force. Alternatively, the everted tissue region may cause the tines and/or tabs of the planar clip to rise above the plane of the clip due to the force of the everted tissue.

Figure 8A:
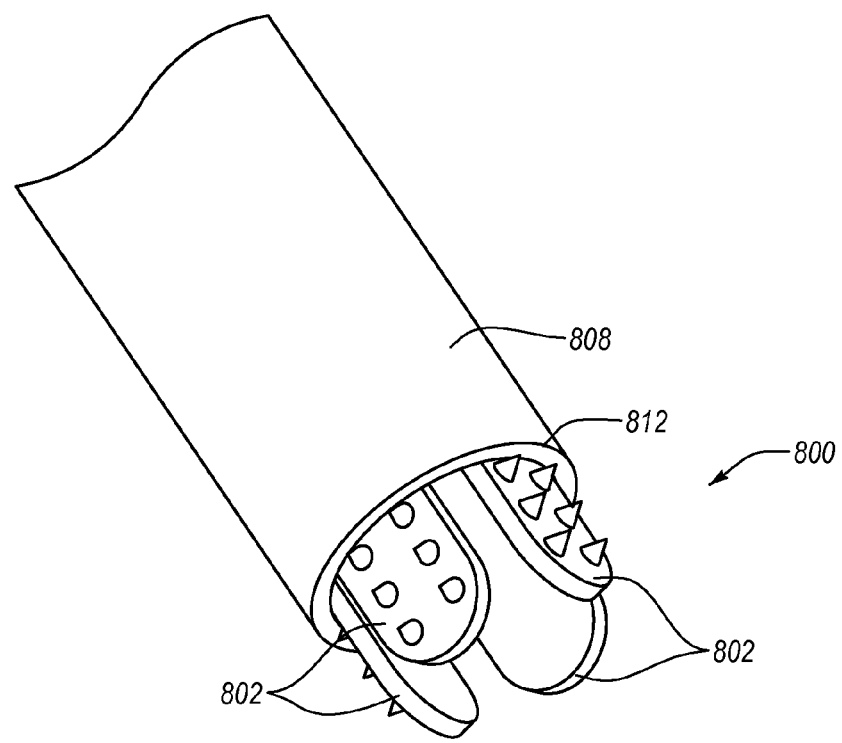
FIGS. 8A and 8B are close-up perspective views of an alternative embodiment of a tissue eversion apparatus comprising a plurality of resilient arms in unexpanded and expanded states, respectively.
Figure 8B:
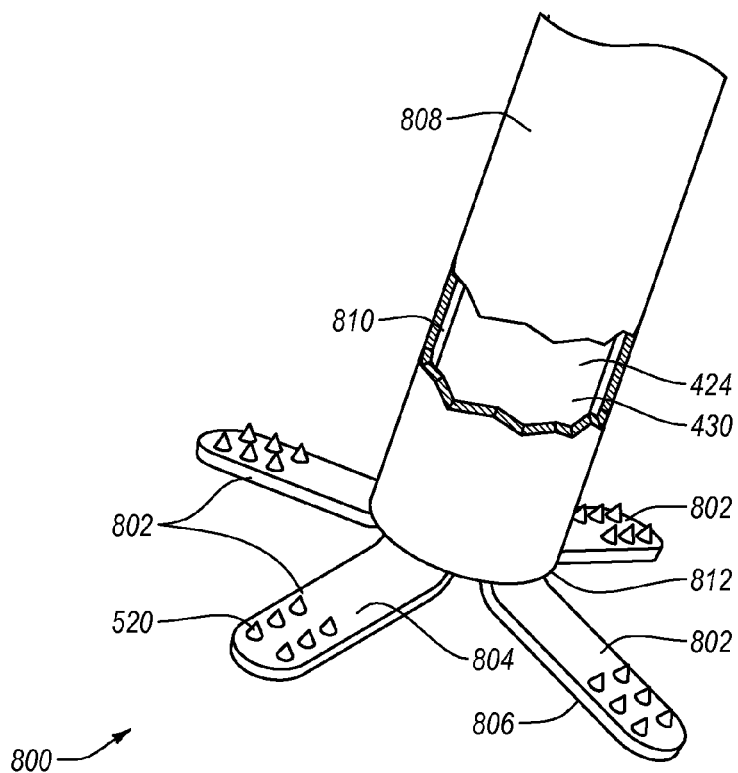

FIGS. 8A and 8B show an alternative embodiment 800 of a tissue eversion apparatus. Tissue eversion apparatus 800 comprises a plurality of resilient arms 802 that are movable between an unexpanded state, shown in FIG. 8A, and an expanded state, shown in FIG. 8B. Although four resilient arms 802 are depicted, it is appreciated that more or less resilient arms 802 can be used.

Each resilient arm 802 extends from a proximal end 804 that is attached to or otherwise formed at distal end region 430 of tubular body 424 to a distal end 806. One or more barbs 520 or other tissue engaging members similar to those discussed previously can be integrally formed with or otherwise attached to distal end 806 of each resilient arm 802 so as to engage tissue when tissue eversion apparatus 800 comes into contact with the tissue while in the expanded state. When tissue eversion apparatus 800 is in the unexpanded state, resilient arms 802 extend substantially longitudinally from tubular body 424 so as to abut each other in a retracted position as shown in FIG. 8A. Conversely, when tissue eversion apparatus 800 is in the expanded state, resilient arms 802 extend laterally from tubular body 424 so as to be spread apart from each other in a deployed position, as shown in FIG. 8B.

Resilient arms 802 can be designed to be biased toward the deployed position. That is, when resilient arms 802 are not in the deployed position, a resilient force can act on resilient arms 802 to force distal ends 806 of resilient arms 802 to spread apart and thereby move to the deployed position. This can be accomplished by using a shape-memory type of material for the resilient arms, such as a nickel-titanium alloy (e.g., Nitinol), or other known shape-memory type of material.

A control sheath 808 having a bore 810 can be used with tissue eversion apparatus 800 to control when resilient arms 802 move between the retracted and deployed positions. When proximal ends 804 of resilient arms 802 are positioned within bore 810, control sheath 808 keeps resilient arms 802 together in the retracted position as shown in FIG. 8A and prevents resilient arms 802 from moving to the deployed position. Conversely, when proximal ends 804 of resilient arms 802 extend out of distal end 812 of bore 810, the resilient force causes resilient arms 802 to remain in the deployed position, as shown in FIG. 8B. Accordingly, control sheath 808 can be used to cause resilient arms 802 to move between the two positions.

For example, when tissue eversion apparatus 800 is in the unexpanded state of FIG. 8A, resilient arms 802 are in the retracted position abutting each other. An external force can be used to move resilient arms 802 distally with respect to control sheath 808. This can be accomplished, e.g., by applying a distal force to tubular body 424 or a proximal force to control sheath 808. Resilient arms 802 can continue to move distally with respect to control sheath 808 until the proximal ends 804 of resilient arms 802 move out of distal end 812 of control sheath bore 810. Once outside of bore 810, resilient arms 802 can spring out to the deployed position by virtue of the resilient force, thereby causing tissue eversion apparatus 800 to be in the expanded state shown in FIG. 8B.

In a similar but opposite manner, when tissue eversion apparatus 800 is in the expanded state of FIG. 8B, resilient arms 802 can be moved proximally with respect to control sheath 808. This causes resilient arms 802 to retract back into the control sheath bore 810. As proximal ends 804 of resilient arms 802 move into bore 810, the bore wall at distal end 812 exerts an inward force on resilient arms 802, overcoming the resilient force and causing distal ends 806 of resilient arms 802 to move inward. As resilient arms 802 retreat further into bore 810, resilient arms 802 move inward until the arms abut each other in the retracted position, thereby causing tissue eversion apparatus 800 to be in the unexpanded state shown in FIG. 8A.

Figure 9E:
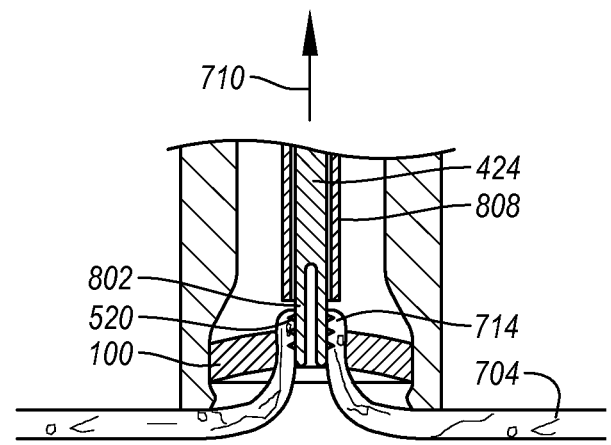

Turning to FIGS. 9A-9F, a method of sealing and/or closing a passage through tissue using tissue eversion apparatus 800 will now be discussed. The method of sealing and/or closing using tissue eversion apparatus 800 is similar to the method discussed above using tissue eversion apparatus 436 with some variations. For example, similar to the previously described method, tissue eversion apparatus 800 is positioned within lumen 418 of sheath 404. However, as shown in FIG. 9A, control sheath 808 is also received within lumen 418 and tissue eversion apparatus 800 is positioned within control sheath 808 so as to be in the unexpanded state, as discussed above. Tissue eversion apparatus 800 can be positioned within control sheath 808 either before or after control sheath 808 has been received within lumen 418. Furthermore, control sheath 808 can be positioned within lumen 418 before or after clip 100 has been positioned within lumen 418. When control sheath 808 and clip 100 have been positioned within lumen 418, distal end 806 of tissue eversion apparatus 800 is disposed adjacent clip 100 at distal end 416 of sheath 404, as shown in FIG. 9A.

Similar to the previously discussed method, once clip 100 has been positioned above opening 700, external deploying force 708 is applied to tubular body 424 which causes the distal end 806 of tissue eversion apparatus 800 to extend through opening 700 and into vessel lumen 702. The same or similar deploying force 900 is simultaneously applied to control sheath 808 so that control sheath 808 moves distally with tissue eversion apparatus 800 to also extend through opening 700 and into vessel lumen 702, as shown in FIG. 9B. Because resilient arms 802 remain within control sheath 808, tissue eversion apparatus 800 remains in the unexpanded state.

The external deploying force 708 continues to be applied to tubular body 424 while the deploying force 900 applied to the control sheath 808 is removed. As a result, tissue eversion apparatus 800 further extends into vessel lumen 702 while control sheath 808 does not. Consequently, resilient arms 802 move out of bore 810 at distal end 812 of control sheath 808. Once outside of bore 810, resilient arms 802 spring out to the deployed position as shown in FIG. 9C and as discussed above. The positioning of distal end 812 of control sheath 808 prevents resilient arms 802 from springing out to the deployed position too soon; without control sheath 808, resilient arms 802 could spring out too soon, causing barbs 520 to snag on the tissue surrounding vessel wall opening 700 instead of the inner surface 712 of the tissue wall 704.

As shown in FIG. 9D, once tissue eversion apparatus 800 is in the expanded state, external retracting force 710 is applied to tubular body 410 to cause tissue eversion apparatus 800 to move proximally and contact inner surface 712 of vessel wall 704, similar to the previously discussed method. The same or similar refracting force 902 is simultaneously applied to control sheath 808 so that control sheath 808 will also move proximally with resilient arms 802. As a result, resilient arms 802 remain in the deployed position and barbs 520 engage inner surface 712 of vessel wall 704.

Similar to the previously discussed method, retracting force 710 is maintained on tubular body 424 to pull everted tissue region 714 upward through clip 100, as shown in FIG. 9E. Retracting force 902 is also maintained so that control sheath 808 moves proximally with resilient arms 802. At a predefined point, retracting force 902 is removed from control sheath 808, so that retracting force 710 on tubular body 424 causes resilient arms 802 to retract into control sheath 808. As resilient arms 802 retract into control sheath 808, resilient arms 802 move inward to the retracted position as discussed above and shown in FIG. 9E. As a result, the everted tissue 714 comes together through clip 100.

Figure 9F:
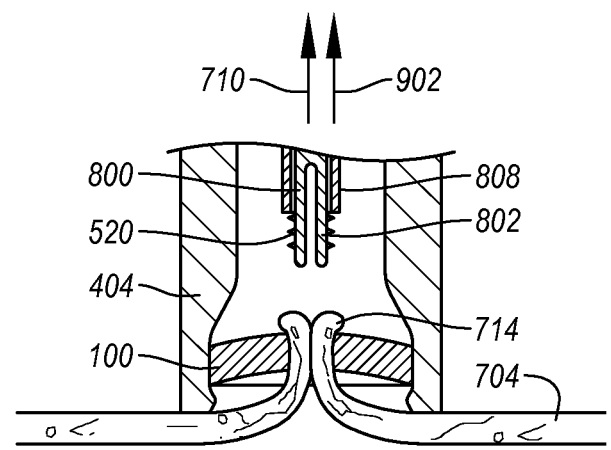

Similar to the previously discussed method, once a desired amount of everted tissue has been pulled proximally through clip 100, barbs 520 disengage from the everted tissue as shown in FIG. 9F. Tissue eversion apparatus 800, control sheath 808, and sheath 404 can then be removed from the body and clip 100 will remain secured to the vessel wall 704 in a similar manner as discussed previously.

Figure 10A:
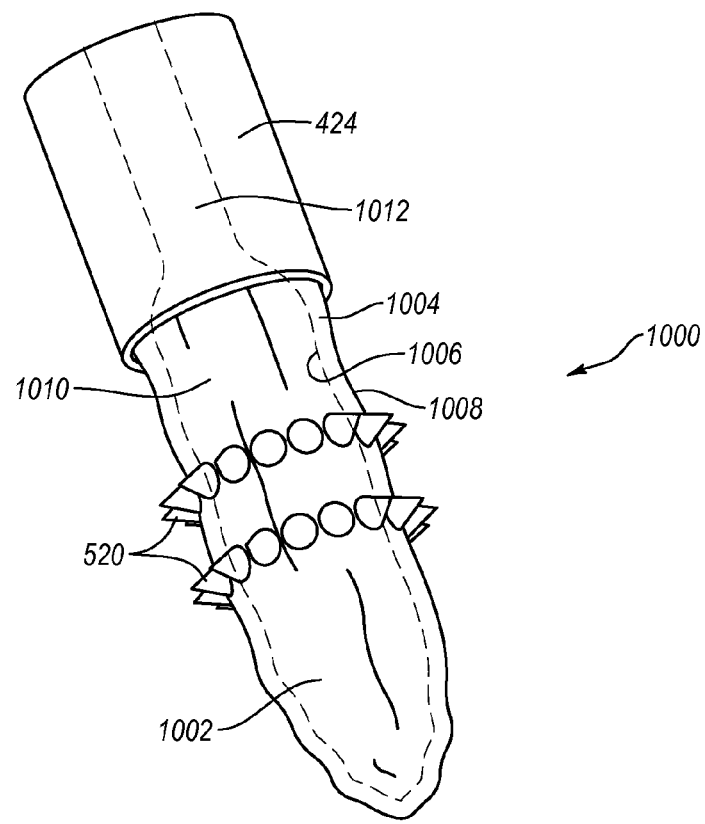
FIGS. 10A and 10B are close-up perspective views of an alternative embodiment of a tissue eversion apparatus comprising a barbed balloon in unexpanded and expanded states, respectively.
Figure 10B:
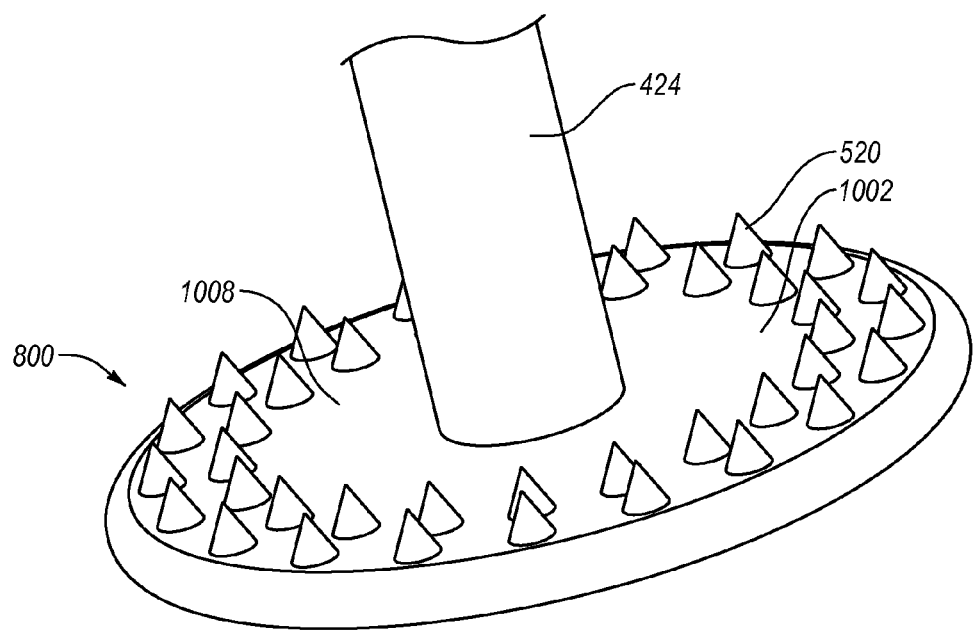

FIGS. 10A and 10B show another alternative embodiment 1000 of a tissue eversion apparatus. Tissue eversion apparatus 1000 comprises a balloon 1002 that is inflatable between an unexpanded state, shown in FIG. 10A, and an expanded state, shown in FIG. 10B.

Balloon 1002 extends distally from distal end region 430 of tubular body 424. Balloon 1002 comprises a thin wall 1004 having an inner surface 1006 and an opposing outer surface 1008. Inner surface 1006 bounds an inflatable chamber 1010. Balloon 1002 is made of an expandable material that is capable of being expanded with air or other type of gas or liquid. For example, balloon 1002 can be made of polyvinyl chloride, nylon, or pebax. Other materials can also be used.

A lumen 1012 can extend through body 424 so as to fluidly communicate with chamber 1010 of balloon 1002. When tissue eversion apparatus 1000 is in the unexpanded state, balloon 1002 is deflated such that the balloon extends longitudinally away from tubular body 424, as shown in FIG. 10A, Conversely, when tissue eversion apparatus 1000 is in the expanded state, balloon 1002 is inflated so as to extend laterally from tubular body 424, as shown in FIG. 10B.

One or more barbs 520 or other tissue engaging members similar to those discussed previously can be integrally formed with or otherwise attached to outer surface 1008 of balloon 1002 so as to engage the tissue when balloon 1002 comes into contact with the tissue while in the expanded state.

During use, the deflated balloon 1002 is inserted through the opening in the tissue similar to the other tissue eversion apparatuses previously discussed. Once inserted, balloon 1002 can be inflated by passing air or other inflating component through lumen 1012 within body 424 and into chamber 1010 of balloon 1003. Balloon 1002 is then retracted back through the opening, similar to previously discussed methods, such that barbs 520 contact and evert tissue around the opening. As balloon 1002 retracts back through clip 100, balloon 1002 can be controllably deflated by selectively releasing air from chamber 1010 and through lumen 1012 of body 424. Similar to previously discussed methods, this causes the everted tissue to come together through clip 100.

Similar to previously discussed methods, once a desired amount of everted tissue has been pulled proximally through clip 100, the barbs 520 disengage from the everted tissue and tissue eversion apparatus 1000 and sheath 404 can be removed from the body and clip 100 will remain secured to the vessel wall.

Although the present invention has been described in considerable detail with reference to certain embodiments, it is contemplated that one skilled in the art may make modifications to the device herein without departing from the scope of the invention. Therefore, the scope of the appended claims should not be considered limited to the embodiments described herein

What is claimed is:

1. A tissue closure device for closing an opening in a tissue having an interior surface and an opposing exterior surface, the tissue closure device comprising:
    a deployment apparatus comprising:
        a sheath having a central longitudinal axis extending between a proximal end and a spaced apart distal end, a lumen extending between the proximal end and the spaced apart distal end, the lumen being bounded by a lumen surface; and a tissue eversion apparatus configured to form an everted tissue region, the tissue eversion apparatus being positioned within the lumen of the sheath and deployable therefrom for engaging the interior surface of the tissue and everting edges of the tissue; and a tissue engaging device operatively coupled to the deployment apparatus and deliverable therefrom, the tissue engaging device comprising an annular-shaped body disposed about a central axis, the annular-shaped body having an aperture extending therethrough for receiving everted edges of the tissue and closing the opening in the tissue, the annular-shaped body being movable between a first position where the annular-shaped body is convex before engagement with the tissue, and a second position where the annular-shaped body is concave when the annular-shaped body is engaged with the tissue, wherein the tissue eversion apparatus includes a plurality of substantially flexible members, each of the plurality of substantially flexible members having a proximal end, a distal end, and a plurality of barbs for everting the tissue and drawing the tissue upward through the aperture of the tissue engaging device such that the everted edges of the tissue extend upward through the aperture when closing the opening in the tissue, the plurality of barbs including a first barb located proximally from the distal end of each of the plurality of substantially flexible members and a second barb located proximally from the first barb, each barb being oriented perpendicular to the plurality of substantially flexible members, and wherein a distal end of the lumen of the sheath of the deployment apparatus includes a retaining member disposed at the distal end of the lumen of the sheath, the retaining member being configured to retain the tissue engaging device in the lumen of the sheath until the tissue is drawn upward through the aperture, wherein a portion of the plurality of substantially flexible members containing the plurality of barbs is planar and perpendicular to the central longitudinal axis of the sheath in a deployed configuration.

2. The tissue closure device according to claim 1, wherein the plurality of barbs are aligned relative to one another on each of the plurality of substantially flexible members.

3. The tissue closure device according to claim 2, wherein the plurality of barbs form a first array and a second array, and wherein the first array of barbs and the second array of barbs are laterally offset from one another and are parallel to each other.

4. The tissue closure device according to claim 1, wherein the portion of the plurality of substantially flexible members containing the plurality of barbs is flat.

5. The tissue closure device according to claim 1, wherein the tissue engaging device is bioabsorbable.

6. The tissue closure device according to claim 1, wherein the tissue eversion apparatus is configured to position the everted edges of the tissue within the tissue engaging device.

7. The tissue closure device according to claim 1, wherein the tissue eversion apparatus also includes an adhesive coating for everting the tissue.

8. The tissue closure device according to claim 1, wherein the aperture of the body of the tissue engaging device is aligned with the lumen of the deployment apparatus so that the tissue eversion apparatus passes through the aperture when deployed from the lumen.

9. The tissue closure device according to claim 1, wherein the tissue eversion apparatus is movable between an unexpanded state in which the tissue eversion apparatus is configured to not contact the tissue, and an expanded state in which the tissue eversion apparatus is configured to contact and evert the tissue.

10. The tissue closure device according to claim 9, wherein the tissue eversion apparatus is configured such that the barbs contact and evert the tissue when the tissue eversion apparatus is in the expanded state.

11. The tissue closure device according to claim 10, wherein each of the plurality of substantially flexible members has an outer surface and wherein the barbs extend outwardly from the outer surface.

12. A tissue closure device for closing an opening in a tissue having an interior surface and an opposing exterior surface, the tissue closure device comprising:

a deployment apparatus comprising:
a sheath having a central longitudinal axis extending between a proximal end and a spaced apart distal end, a lumen extending between the proximal end and the spaced apart distal end, the lumen being bounded by a lumen surface; and a tissue eversion apparatus configured to form an everted tissue region, the tissue eversion apparatus being positioned within the lumen of the sheath and deployable therefrom for engaging the interior surface of the tissue and everting edges of the tissue; and a tissue engaging device operatively coupled to the deployment apparatus and deliverable therefrom, the tissue engaging device comprising an annular-shaped body disposed about a central axis, the annular-shaped body having an aperture extending therethrough for receiving everted edges of the tissue and closing the opening in the tissue, the annular-shaped body having a plurality protruding members extending into the aperture and separated by corresponding intermember spaces, wherein at least one of the plurality protruding members comprises a tine and wherein at least one of the plurality protruding members comprises a tab;

the tissue eversion apparatus including a plurality of substantially flexible members, each of the plurality of substantially flexible members having a proximal end, a distal end, and a plurality of barbs for everting the tissue and drawing the tissue upward through the aperture of the tissue engaging device such that everted edges of the tissue extend upward through the aperture when closing the opening in the tissue, the plurality of barbs including a first barb located proximally from the distal end of each of the plurality of substantially flexible members and a second barb located proximally from the first barb, each barb being oriented perpendicular to the plurality of substantially flexible members, wherein the annular-shaped body of the tissue engaging device is movable between a first position where the annular-shaped body is convex before engagement with the tissue, and a second position where the annular-shaped body is concave when the annular-shaped body is engaged with the tissue so as to draw additional tissue upward through the aperture of the tissue engaging device when closing the opening in the tissue, and wherein a distal end of the lumen of the sheath of the deployment apparatus includes a retaining member disposed at the distal end of the lumen of the sheath, the retaining member being configured to retain the tissue engaging device in the lumen of the sheath until the tissue is drawn upward through the aperture, and wherein a portion of the plurality of substantially flexible members containing the plurality of barbs is planar and perpendicular to the central longitudinal axis of the sheath in a deployed configuration.

13. The tissue closure device according to claim 12, wherein the tissue engaging device is bioabsorbable.

14. The tissue closure device according to claim 12, wherein the aperture of the annular-shaped body of the tissue engaging device is aligned with the lumen of the deployment apparatus so that the tissue eversion apparatus passes through the aperture when deployed from the lumen.

15. The tissue closure device according to claim 12, wherein the tissue eversion apparatus is movable between an unexpanded state in which the tissue eversion apparatus is configured to not contact the tissue, and an expanded state in which the tissue eversion apparatus is configured to contact and evert the tissue.

16. The tissue closure device according to claim 15, wherein the tissue eversion apparatus is configured such that the barbs contact and evert the tissue when the tissue eversion apparatus is in the expanded state.

17. The tissue closure device according to claim 10, wherein each of the plurality of substantially flexible members has an outer surface and wherein the barbs extend outwardly from the outer surface.

18. A method of closing an opening in a body tissue, the method comprising:
providing a tissue closure device for closing the opening in the body tissue having an interior surface and an opposing exterior surface, the tissue closure device comprising:
a deployment apparatus comprising:
a sheath having a central longitudinal axis extending between a proximal end and a spaced apart distal end, a lumen extending between the proximal end and the spaced apart distal end, the lumen being bounded by a lumen surface; and
a tissue eversion apparatus configured to form an everted tissue region, the tissue eversion apparatus being positioned within the lumen of the sheath and deployable therefrom for engaging the interior surface of the body tissue and everting edges of the body tissue; and
a tissue engaging device operatively coupled to the deployment apparatus and deliverable therefrom, the tissue engaging device comprising an annular-shaped body disposed about a central axis, the annular-shaped body having an aperture extending therethrough for receiving everted edges of the body tissue and closing the opening in the body tissue, the annular-shaped body being movable between a first position where the annular-shaped body is convex before engagement with the body tissue and a second position where the annular-shaped body is concave when the annular-shaped body is engaged with the body tissue,
wherein the tissue eversion apparatus includes a plurality of substantially flexible members, each substantially flexible member having a proximal end, a distal end, and a plurality of barbs for everting the body tissue and drawing the body tissue upward through the aperture of the tissue engaging device such that the everted edges of the body tissue extend upward through the aperture when closing the opening in the body tissue, the plurality of barbs including a first barb located proximally from the distal end of each of the plurality of substantially flexible members and a second barb located proximally from the first barb, each barb being oriented perpendicular to the plurality of substantially flexible members, and
wherein a distal end of the lumen of the sheath of the deployment apparatus includes a retaining member disposed at the distal end of the lumen of the sheath, the retaining member being configured to retain the tissue engaging device in the lumen of the sheath until the body tissue is drawn upward through the aperture, wherein a portion of the plurality of substantially flexible members containing the plurality of barbs is planar and perpendicular to the central longitudinal axis of the sheath in a deployed configuration;
positioning the tissue engaging device over the opening in the body tissue;
forming an everted tissue region around the opening in the body tissue; and
passing the everted tissue region through the aperture in the tissue engaging device, thereby causing the tissue engaging device to become substantially concave with respect to the body tissue to secure the everted tissue region within the aperture and close the opening.

19. A method of closing an opening extending between an interior surface and an opposing exterior surface of a body tissue, the method comprising:
positioning a deployment apparatus adjacent the opposing exterior surface and over the opening in the body tissue, the deployment apparatus comprising:
a sheath having a central longitudinal axis extending between a proximal end and a spaced apart distal end, a lumen extending between the proximal end and the spaced apart distal end, the lumen being bounded by a lumen surface; and
a tissue eversion apparatus configured to form an everted tissue region, the tissue eversion apparatus being positioned within the lumen of the sheath and deployable therefrom for engaging the interior surface of the body tissue and everting edges of the body tissue; and
a tissue engaging device operatively coupled to the deployment apparatus and deliverable therefrom, the tissue engaging device comprising an annular-shaped body disposed about a central axis, the annular-shaped body having an aperture extending therethrough for receiving everted edges of the body tissue and closing the opening in the body tissue, the annular-shaped body being movable between a first position where the annular-shaped body is convex before engagement with the body tissue and a second position where the annular-shaped body is concave when the annular-shaped body is engaged with the body tissue,
wherein the tissue eversion apparatus includes a plurality of substantially flexible members, each substantially flexible member having a proximal end, a distal end, and a plurality of barbs for everting the body tissue and drawing the body tissue upward through the aperture of the tissue engaging device such that the everted edges of the body tissue extend upward through the aperture when closing the opening in the body tissue, the plurality of barbs including a first barb located proximally from the distal end of each of the plurality of substantially flexible members and a second barb located proximally from the first barb, each barb being oriented perpendicular to the plurality of substantially flexible members, and
wherein a distal end of the lumen of the sheath of the deployment apparatus includes a retaining member disposed at the distal end of the lumen of the sheath, the retaining member being configured to retain the tissue engaging device in the lumen of the sheath until the body tissue is drawn upward through the aperture, wherein a portion of the plurality of substantially flexible members containing the plurality of barbs is planar and perpendicular to the central longitudinal axis of the sheath in a deployed configuration;

deploying the tissue eversion apparatus from the sheath through the opening of the body tissue so that the tissue eversion apparatus engages the interior surface of the body tissue;

retracting the tissue eversion apparatus back into the sheath, the engagement of the tissue eversion apparatus with the interior surface of the body tissue causing an everted tissue region to be formed around the opening as the tissue eversion apparatus is retracted, the everted tissue region being passed through the aperture in the tissue engaging device as the tissue eversion apparatus is retracted, thereby causing the tissue engaging device to become substantially concave with respect to the body tissue to secure the everted tissue region within the aperture and close the opening; and disengaging the tissue eversion apparatus from the everted tissue region, the everted tissue region remaining secured within the tissue engaging device to close the opening, and the tissue engaging device remaining substantially concave with respect to the body tissue.

20. The method according to claim 19, wherein deploying the tissue eversion apparatus comprises extending the plurality of substantially flexible members such that the barbs disposed on an outer surface of the plurality of substantially flexible members extend through the opening of the body tissue in an unexpanded state and expanding the substantially flexible members such that the tissue engaging members engage the interior surface of the body tissue.

* * * * *